United States Patent [19]
Jewitt

[11] Patent Number: 4,914,038
[45] Date of Patent: Apr. 3, 1990

[54] APPARATUS AND METHOD FOR AVOIDING CIRCUMVENTION OF AN IDENTITY CONFIRMING BREATH TESTER

[75] Inventor: Jeffrey C. Jewitt, Etobicoke, Canada

[73] Assignee: Guardian Technologies, Inc., Cincinnati, Ohio

[21] Appl. No.: 231,887

[22] Filed: Aug. 12, 1988

Related U.S. Application Data

[63] Continuation of Ser. No. 209,091, Jun. 17, 1988.

[51] Int. Cl.$^4$ ............................................. G01N 33/00
[52] U.S. Cl. .................................... 436/132; 180/272; 307/10.6; 340/576; 422/84; 436/900
[58] Field of Search .................. 436/132, 900; 422/84; 180/272; 307/10.6; 340/576

[56] References Cited

U.S. PATENT DOCUMENTS

| | | |
|---|---|---|
| 3,764,270 | 10/1973 | Collier et al. |
| 3,824,537 | 7/1974 | Albertson |
| 3,824,538 | 7/1974 | Slemp ................................ 180/272 |
| 3,830,630 | 8/1974 | Kiefer et al. |
| 3,831,707 | 8/1974 | Takeuchi |
| 4,093,945 | 6/1978 | Collier et al. |
| 4,300,385 | 11/1981 | Albarda ................................ 73/23 |
| 4,314,564 | 2/1982 | Albarda |
| 4,592,443 | 6/1986 | Simon |
| 4,678,057 | 7/1987 | Elfman |
| 4,707,336 | 11/1987 | Jones |
| 4,738,333 | 4/1988 | Collier et al. |

FOREIGN PATENT DOCUMENTS 2184245 6/1987 United Kingdom .
2211009 6/1989 United Kingdom .

OTHER PUBLICATIONS

"Potential for Application of Ignition Interlock Devices to Prohibit Operation of Motor Vehicles By Intoxicated Individuals", A Report to Congress, U.S. Dept. of Transportation, National Highway Traffic Safety Administration, May 1988, pp. 1–39.

Primary Examiner—Barry S. Richman
Assistant Examiner—Timothy M. McMahan
Attorney, Agent, or Firm—Wood, Herron & Evans

[57] ABSTRACT

A breath sobriety test system deters circumvention of a test having an alcohol measuring phase and an identification phase. In an alcohol measuring phase, the alcohol content of a breath sample delivered by an operator/test subject is measured in the conventional manner according to the electrical output signal of an alcohol sensor. In the identification phase, the operator/test subject confirms his or her identity as a designated individual by performing an identity-confirming act recognizable by the system. The identity-confirming act includes delivering breath to the system. The response of the alcohol sensor to the breath delivered in the identification phase is compared with the reading taken during the alcohol measuring phase. If the two readings differ by more than a predetermined amount and in particular if the identification phase reading exceeds the alcohol measurement phase reading by more than said amount, the test is not passed regardless of whether the alcohol measurement is otherwise acceptable and regardless of whether the identity-confirming act is performed correctly.

17 Claims, 33 Drawing Sheets

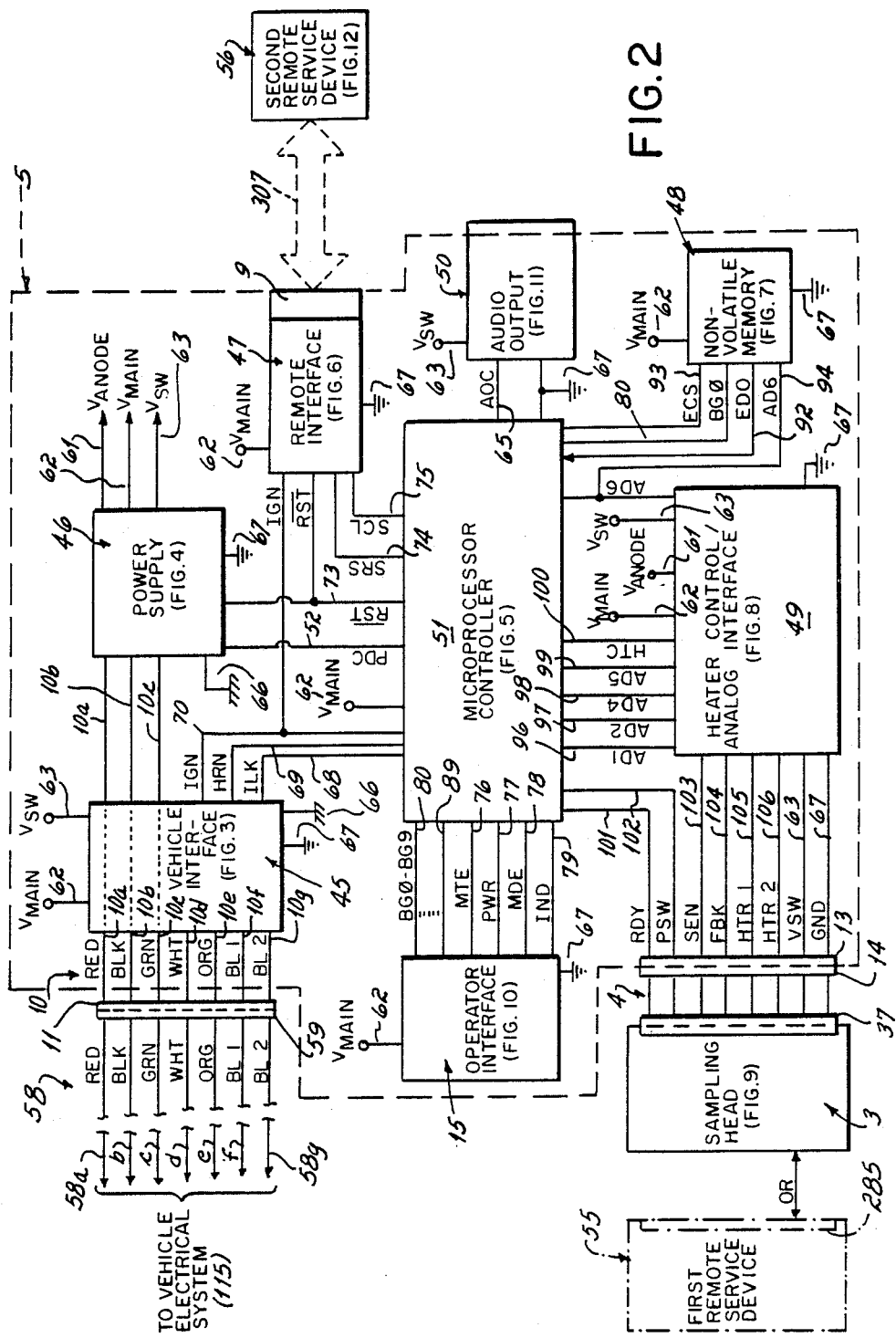

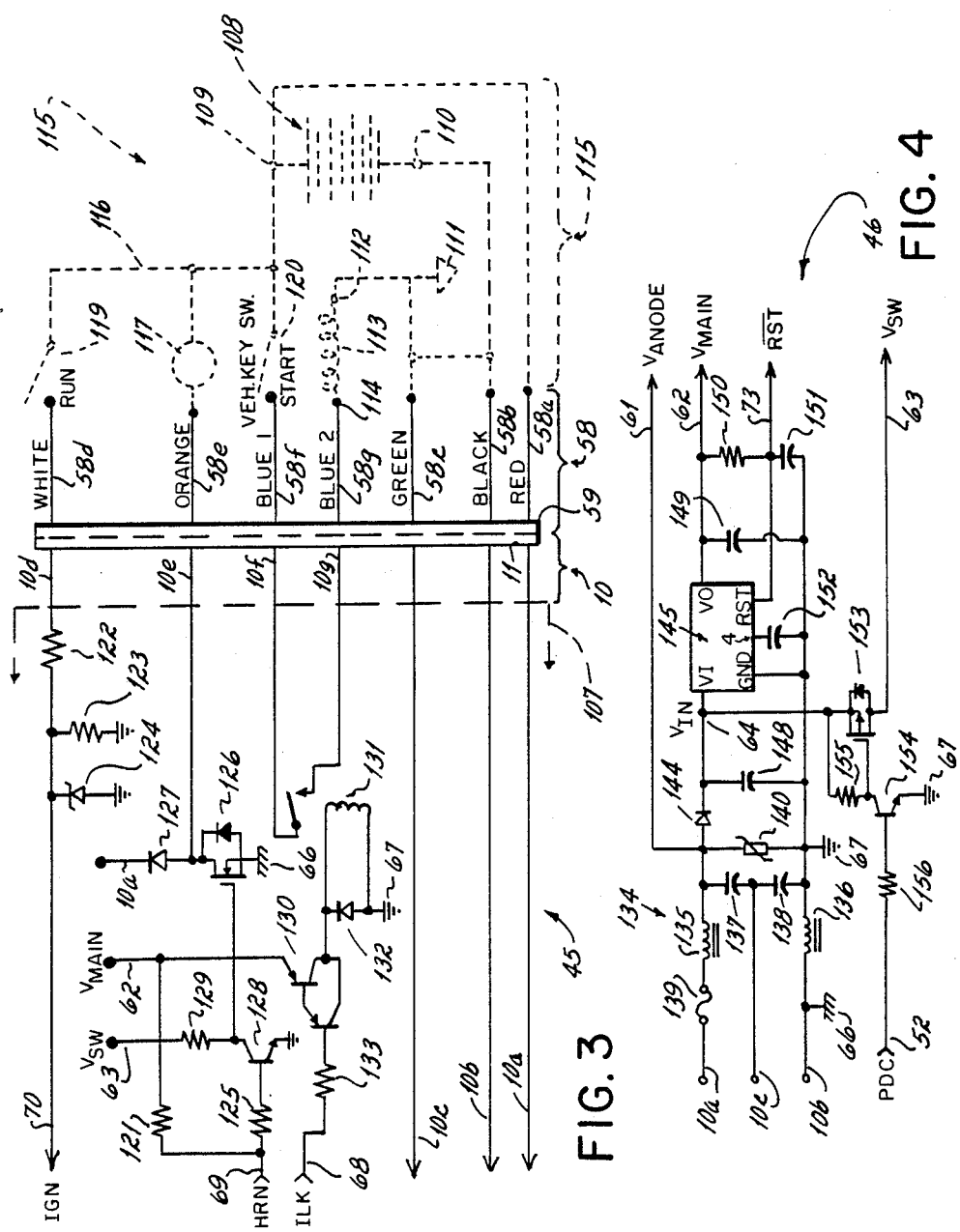

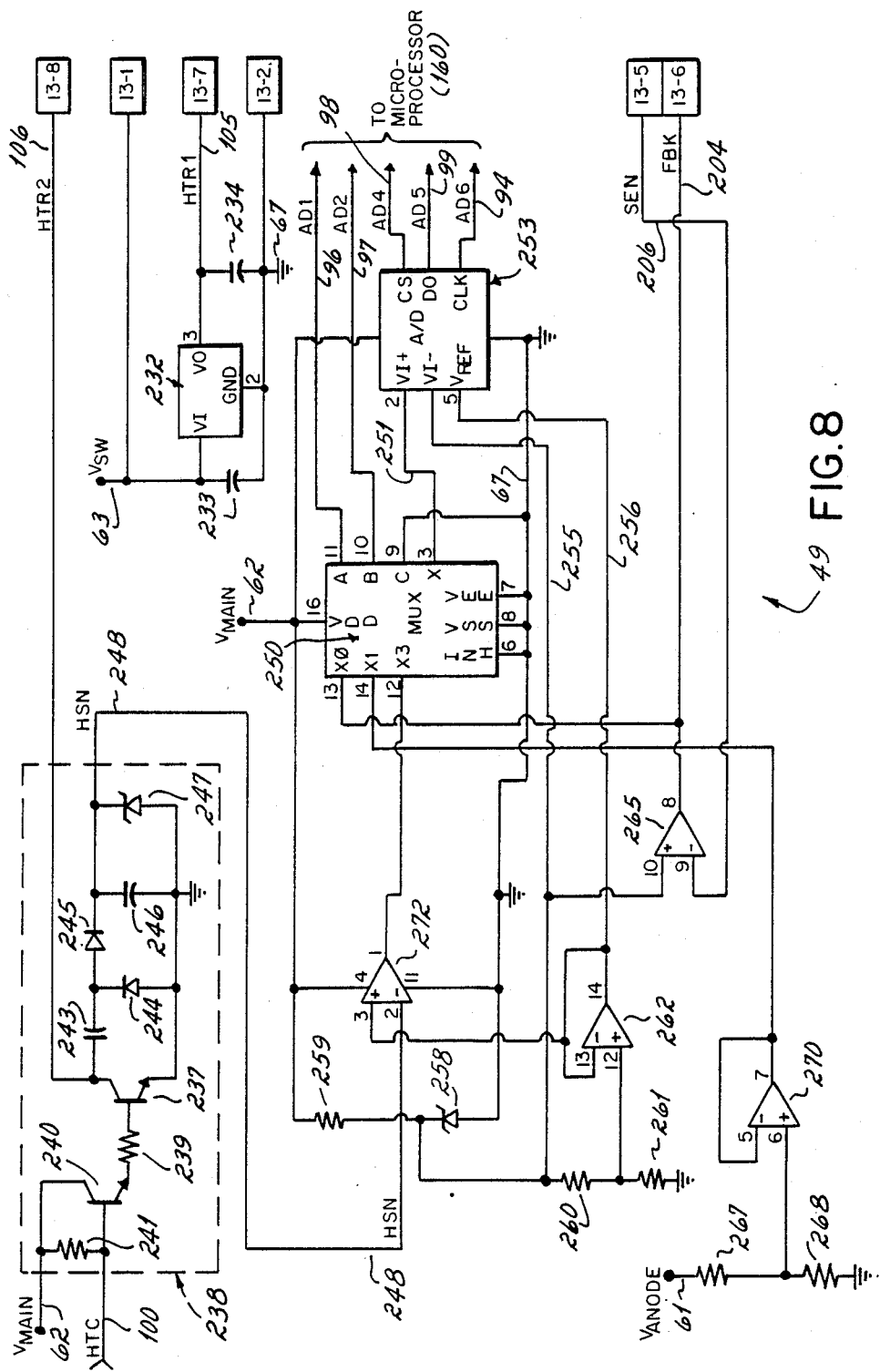

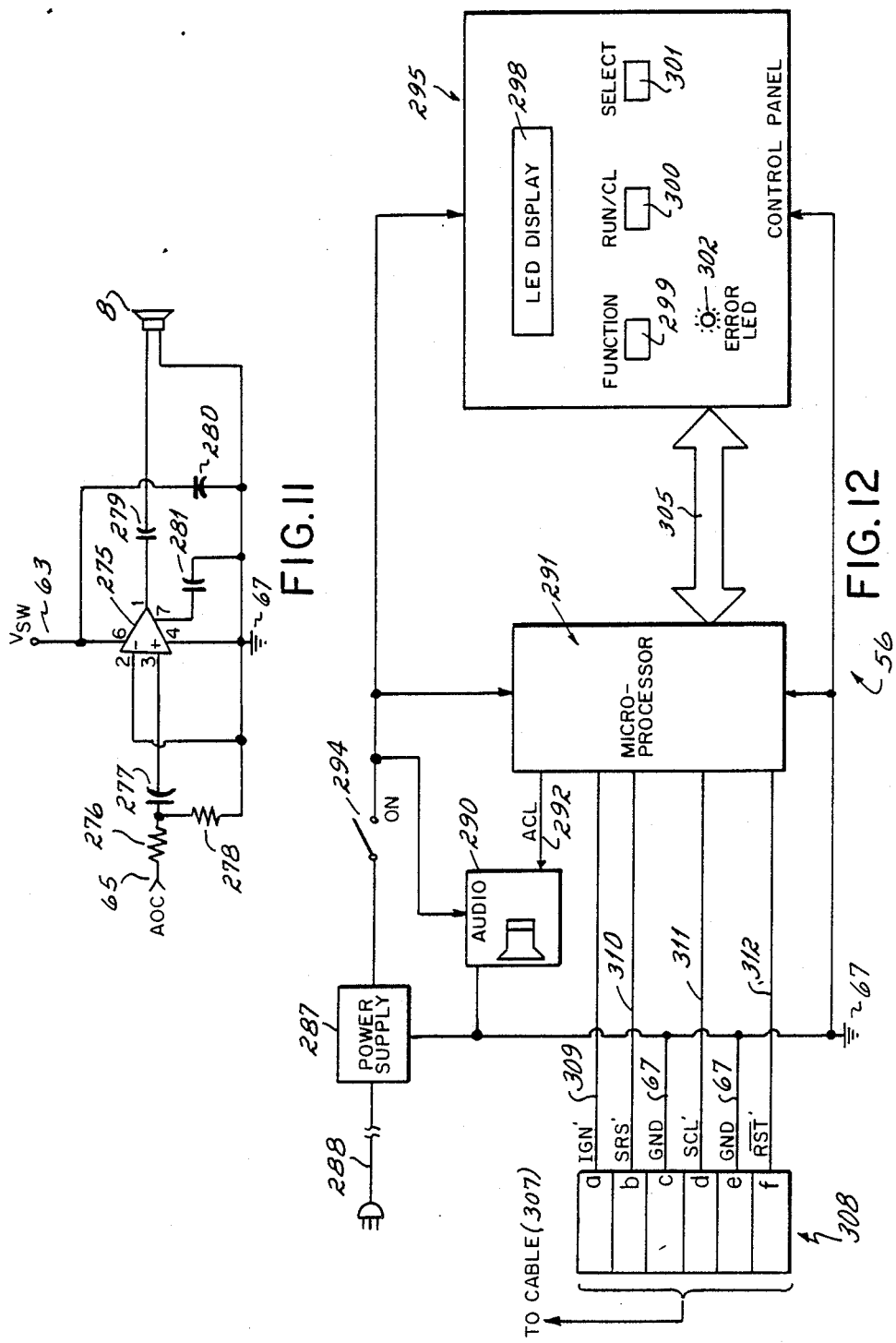

APPARATUS AND METHOD FOR AVOIDING CIRCUMVENTION OF AN IDENTITY CONFIRMING BREATH TESTER

CROSS REFERENCE TO RELATED APPLICATIONS

This application is a continuation of co-pending commonly assigned U.S. patent application Ser. No. 209,091 entitled "Sobriety Interlock With Bypass Detection" filed June 17, 1988.

FIELD OF THE INVENTION

The present invention relates to breath sobriety testing. More particularly, the invention relates to an apparatus and method for avoiding circumvention of a breath sobriety tester such as the type which can be used in a breath sobriety interlock system connectable to a vehicle or other machine and normally operating to disable the vehicle from starting unless a breath sobriety test is passed by a person whose identity is confirmed by the system.

BACKGROUND OF THE INVENTION

The operation of vehicles by persons under the influence of alcohol is a major safety problem in the United States and many other countries. Despite growing public awareness and government concern, statistics continue to show that a high percentage of automobile accidents causing serious injury or death involve drivers who have been drinking alcoholic beverages in excess. Injuries in the workplace are also often found to be related to the operation of heavy equipment or other machinery by persons impaired by the effects of alcohol.

To address this problem, various attempts have been made to develop devices intended to prevent automobiles and the like from being operated by inebriated individuals. Such devices, which are commonly referred to as "sobriety interlocks" are often based on the well known principle that the gas present in the alveoli of the lungs has an alcohol content directly proportional to that of the bloodstream. Blood alcohol content (BAC) thus can be accurately determined by breath testing A sobriety interlock is connected to the vehicle and normally operates to prevent the vehicle from being started unless one or more prerequisite conditions imposed by the interlock are satisfied. Foremost among such conditions is that any alcohol detected be present in a sufficiently low concentration although, the interlock may normally require any number of further conditions to be met before starting of the vehicle is enabled.

For example, it is generally acknowledged that to accurately determine BAC from a breath sample, an interlock must be designed to require delivery of a "deep lung" breath sample. As used herein and in the claims, that term refers to a breath sample consisting of a proportion of alveolar gas sufficient to permit an accurate determination of blood alcohol concentration. Since breath expired from upper portions of the respiratory tract does not necessarily have an alcohol level proportional to that of the bloodstream, a deep lung sample is essential if an interlock is not to be defeated by shallow exhalations of a series of short puffs of breath expelled from upper portions of the respiratory tract.

This problem is addressed effectively in U.S. Pat. Nos. 4,093,945 and 3,764,270 issued to Collier et al. The Collier et al. patents disclose means, such as a pressure switch and timer system, to ensure delivery of an essentially continuous and uninterrupted flow of breath sufficient to yield a deep lung sample. The sampling interval determined by the timer and the flow rate (as measured by the pressure sensor or other flow sensing means) are selected together to ensure a deep lung sample will be given. Unless breath is delivered at at least a minimum predetermined flow rate without interruption for the entire sampling interval, a required condition is not deemed satisfied and the vehicle cannot be started.

Unlike breath analyzer tests which are usually administered under the supervision of police or other trained persons, sobriety interlocks are routinely used outside the presence of persons other than the vehicle operator/test subject whose use of the interlock may be less than completely voluntary. One example of such a situation is where an employer seeks liability protection by installing interlocks on vehicles operated by employees. A higher degree of compulsion may be involved in some cases of court-supervised rehabilitation of offenders found to have been driving while under the influence of alcohol (DUI). As a mandatory condition for permitting a DUI offender to drive in order to maintain employment and/or obtain counselling, some courts may require a sobriety interlock to be installed in the offender's car. In such cases there is an increased likelihood that attempts to defeat the interlock will be made. Accordingly, the prior art has proposed various self-supervisory techniques directed toward avoiding circumvention of interlocks by various forms of subterfuge. These techniques typically share a common characteristic in that they require one or more additional conditions, usually unrelated to alcohol to be satisfied as prerequisites to starting the vehicle.

For example, techniques to discriminate between a contemporaneous breath sample and bogus gasses such air from a bicycle pump, filling station air hose or breath from a previously inflated balloon are discussed in U.S. Pat. Nos. 4,592,443; 3,831,707; and 3,824,537. Each of these patents proposes requiring one or more additional conditions be satisfied before permitting the vehicle to start. U.S. Pat. No. 4,592,443 requires the temperature of the gas delivered for a test to fall within a range expected for breath. Breath being moist, U.S. Pat. No. 3,831,707 requires the gas to contain appropriate humidity to avoid circumventing an interlock with a bogus gas that is drier than breath. U.S. Pat. No. 3,824,537 teaches requiring the operator to place one hand on a button which must be activated during a test period while the other hand is used to hold a breath sampling tube located some distance away from the button. Since both hands of the operator are placed apart, deceptive manipulation of a bellows or the like is discouraged. While all of these techniques have some merit, they are of little overall benefit if a sobriety interlock can be circumvented regardless of them by the simple artifice of enlisting the aid of a sober accomplice to take the test. This vexing problem is dealt with in U.S. Pat. No. 4,738,333 to Collier et al.

The technique proposed in the above '333 patent is to require the operator/test subject to identify himself or herself by correctly performing what is termed an "identity-confirming act" which the interlock is capable of recognizing. Unless this act is correctly performed within a limited number of attempts, the interlock will not permit the vehicle to be started regardless of the result of any alcohol breath test. Unlike a personal identification number (PIN) code which can be readily entered by another person who is merely given knowledge of the code, correct performance of the identity-confirming act requires a degree of skill which cannot ordinarily be acquired by most persons without attempting the act at least some minimum number of times. The limited number of attempts the interlock allows the act to be tried is selected to be lower than the minimum number of attempts ordinarily required to learn the act. In this way, the interlock can effectively discriminate between a trained designated person and a previously unskilled accomplice. Where a sobriety interlock includes such identification means, both the alcohol measuring phase and the identification phases of the test must be passed as prerequisites to enable starting of a vehicle or other equipment connected to the interlock.

One embodiment of the invention which is specifically described in the above-referenced '333 patent requires placing the mouth or lips over the breath sample delivery port of the system in order to deliver breath thereinto in a predefined manner to perform the identity-confirming act. By requiring use of the same physical location as that which is employed to deliver a breath sample for breath alcohol analysis to perform the identity-confirming act, increased assurance that these two acts will not be performed by different persons is provided. Further, the system can require either a very short time delay or no delay at all between breath sample delivery and the identity confirming act thus making it highly unlikely that two different persons could act quickly enough to deliver the breath sample and perform the identity confirming act. Even with such precautions it is desirable to even more positively ensure that the identity confirming act is performed by the same individual who delivers the breath sample.

Additionally, there are other forms of breath test apparatus in which users identity is determined from an act performed by the user by breathing or speaking into the mouthpiece of the breath tester, such as in the use of sobriety breath test apparatus employed with remote confinement or "home arrest" systems, such as are described in co-pending and commonly assigned U.S. patent application Ser. No. 4,843,377.

Accordingly, there exists a need to increase the assurance that a breath sample has not been delivered by artificial means or by one other than the identified operator of a sobriety interlock, particularly interlock systems of the type disclosed in U.S. Pat. No. 4,738,333.

SUMMARY OF THE INVENTION

It is a primary objective of the present invention to satisfy the above described needs by providing an apparatus and method effective to reduce the likelihood that a substitute person or other source will furnish a bogus gas sample in a breath sobriety test system in which the identity of an operator/test subject is confirmed based on the ability of that person to perform an act which includes breathing into the test apparatus.

According to the present invention, an operator/test subject delivers an initial breath sample to the test apparatus. The alcohol content of that breath sample is measured in the normal manner according to the electrical output signal developed by an alcohol sensor. At a different time, which is preferably after the initial breath sample has been delivered, the operator/test subject is required to perform an identity-confirming act in order to confirm that he or she is a designated individual. The identity-confirming act includes the delivery of breath to the test apparatus. The present invention contemplates reading the output of the alcohol sensor induced by the latter mentioned breath and comparing it to the initial reading. If the second reading differs from the initial reading by more than a predetermined amount and in particular, if the second reading exceeds the initial reading by more than said amount, the test is not passed regardless of whether the initial breath alcohol measurement was otherwise acceptable and regardless of whether the identity-confirming act was correctly performed. The invention thus serves to thwart attempts to circumvent the test by using different gas sources for the alcohol measuring and identification phases of a test.

These and other objectives and advantages of the present invention will be more readily apparent from the following detailed description of the drawings in which:

BRIEF DESCRIPTION OF THE DRAWINGS

FIG. 2 is an electrical block diagram showing the sobriety interlock of FIG. 1 together with a wiring harness for connecting the interlock to a vehicle electrical system and illustrating the connection of the interlock to first and second remote service devices.

FIG. 3 is an electrical diagram showing further details of the vehicle interface depicted in block form in FIG. 2 and illustrating its connection to a portion of a vehicle electrical system.

FIG. 4 is an electrical diagram showing further details of the power supply depicted in block form in FIG. 2.

FIG. 8 is an electrical diagram showing further details of the heater control/analog interface depicted in block form in FIG. 2.

FIG. 11 is an electrical diagram showing further details of the audio output depicted in block form in FIG. 2.

FIG. 12 is an electrical block diagram showing further details of the second remote service device shown in FIG. 2.

FIGS. 13A-13F are a series of flowcharts illustrating the operation of the second remote interface device of FIG. 12 wherein:

FIG. 13A illustrates the BOOT UP state;
FIG. 13B illustrates the READTIME state;
FIG. 13C illustrates the SETTIME state;
FIG. 13D illustrates the READBYP state;
FIG. 13E illustrates the RESETT state; and FIG. 13F illustrates the CONERR, COMMERR and RSTERR error subroutines.

DETAILED DESCRIPTION OF THE PREFERRED EMBODIMENT

Sobriety Interlock Hardware

Figure 1:
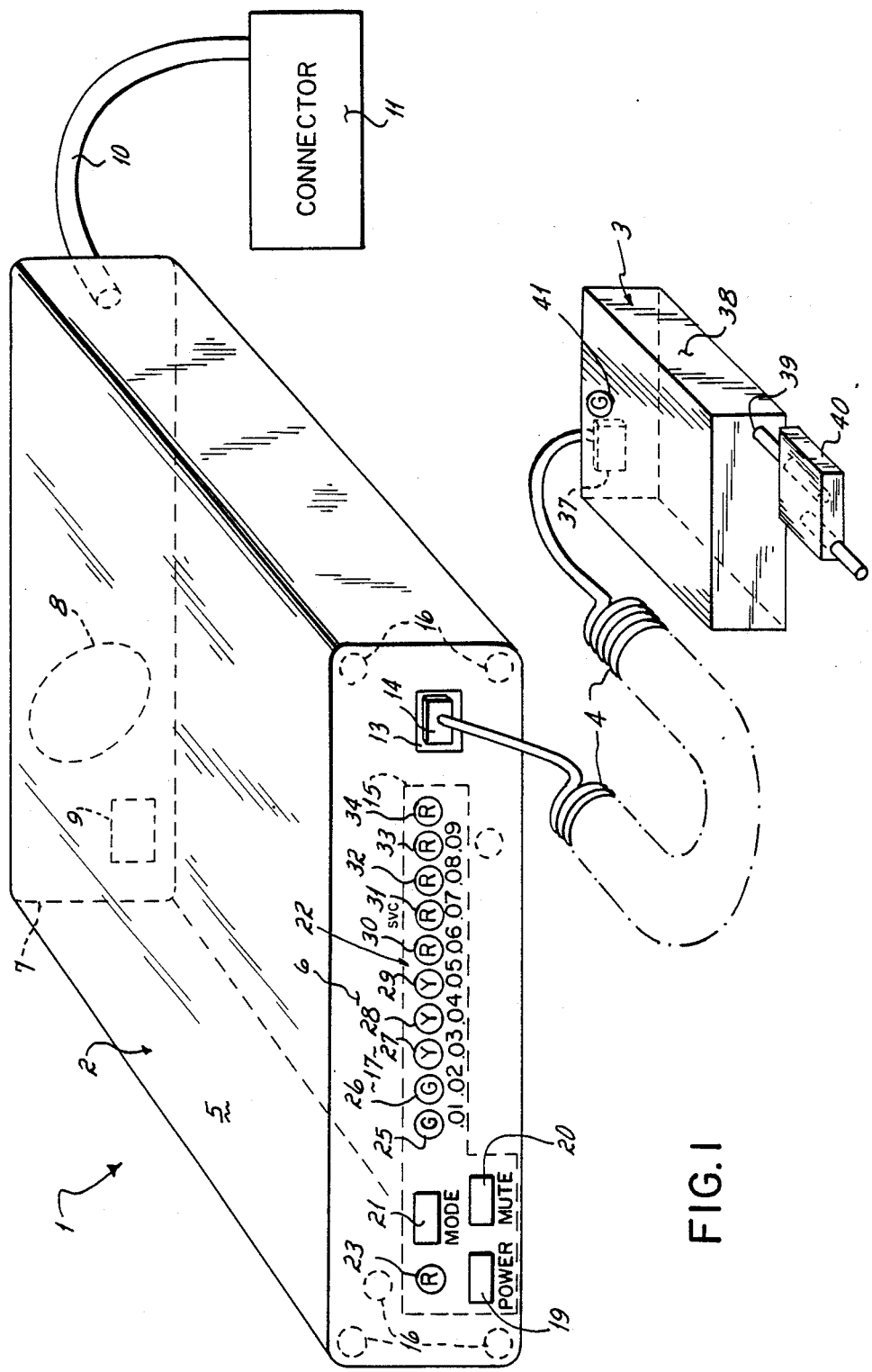
FIG. 1 is a pictorial view of one preferred embodiment of a sobriety interlock embodying the present invention.

Referring initially to FIG. 1, a sobriety interlock 1 embodying the present invention includes a control module 2 and a remote sampling head 3 connected thereto by way of a coilably retractable cable 4. Control module 2 is contained within a housing 5 having mutually opposed front and rear panels, 6 and 7, respectively. Rear panel 7 carries an audio beeper 8 and a miniature, six pin, female receptacle 9. A multiple conductor wiring pigtail 10 terminated with half of a locking male-female connector 11 exits rear panel 7 to facilitate connection of control module 2 to a vehicle electrical system in a manner to be more fully explained with reference to FIGS. 2 and 3.

The front panel 6 of control module 2 carries an eight pin, miniature female receptacle 13 which mates with a detachable male plug 14, one of which is affixed to each end of cable 4. Front panel 6 also carries the externally accessible portions of an operator interface 15. The internal components of control module 2 are secured within housing 5 by a plurality of fasteners 16 the heads of which are concealed beneath an overlay 17. Overlay 17 is imprinted with appropriate indicia as shown and, for security purposes, is of a material such as a thin sheet of polycarbonate backed with a strong, pressure sensitive adhesive so that overlay 17 shows visible signs of tampering if removal of it or fasteners 16 is attempted. A similar overlay (not shown) is provided on the surface of rear panel 7 covering fasteners there (also not shown).

That portion of operator interface 15 accessible by way of front panel 6 includes three push buttons 19, 20 and 21 designated POWER, MUTE and MODE respectively, as well as a bar graph style LED display 22 and a red indicator LED 23. Bar graph display 22 includes a series of ten colored LEDs numbered consecutively from 25 through 34 as viewed from left to right in FIG. 1. These consist respectively of; first and second GREEN LEDs (25, 26), first, second and third YELLOW LEDs (27, 28, 29) and first, second, third, fourth and fifth RED LEDs (30, 31, 32, 33, 34).

Sampling head 3 is detachably connected to cable 4 by way of a second, eight pin miniature female receptacle 37 which receives one of the male plugs 14 terminating cable 4. The structure and operation of sampling head 3 are described in further detail herein with reference to FIGS. 1 and 9 as well as in copending, commonly assigned U.S. patent application Ser. No. 07/152,470, filed Feb. 5, 1988 the disclosure of which is expressly incorporated herein by reference in its entirety. For the present, it is sufficient to note that sampling head 3 includes a housing 38 having a breath inlet port 39 into which a breath sample can be delivered by way of a disposable mouthpiece 40. A green colored READY LED 41 is visible externally of housing 38. When interlock 1 is prepared to receive a breath sample, READY LED 41 flashes. While a breath sample is in the process of being delivered at a sufficient flow rate, READY LED 41 stops flashing and remains lighted.

Referring now to FIG. 2 there is shown an electrical block diagram wherein the confines of the housing 5 enveloping control module 2 are indicated in broken lines. It can be seen from FIG. 2 that control module 2 includes a vehicle interface 45, a power supply 46, a remote interface 47, a non-volatile memory 48, an analog interface and heater control 49, operator interface 15 (a portion of which has already been described) as well as an audio output 50; each of which is connected via one or more lines to a microprocessor controller 51.

Control module 2 also includes provisions for a number of external connections. These include connections to sampling head 3 as well as the vehicle electrical system. As previously noted, sampling head 3 is connected to control module 2 via cable 4 and the male plugs 14, 37 which terminate it. The connections between the vehicle and vehicle interface 45 are made by way of pigtail 10 and a wiring harness 58 which includes a connector 59 that mates with the connector 11 terminating pigtail 10. As shown, pigtail 10 includes separate red, black, green, white and orange wires labelled respectively as 10a–10e as well as a pair of blue wires labelled 10f and 10g. Wiring harness 58 includes a set of correspondingly colored wires 58a–58g the connections of which to the vehicle will be described later with reference to FIG. 3. Also, in place of sampling head 3, the female receptacle 13 mounted on the front panel 6 of control module 2 can be connected to a first remote service device 55 while remote interface 47 is adpted to communicate via receptacle 9 with a second remote service device 56. Remote service devices 55 and 56 will also be explained in further detail later.

With continuing reference to FIG. 2 the principal internal connections of control module 2 will now be summarized. Vehicle interface 45 conducts lines 10a, 10b and 10c directly to power supply 46 to supply it with electrical power from the vehicle. As will be explained further in connection with FIG. 4, power supply 46 defines three power supplies designated $V_{ANODE}$ 61, $V_{MAIN}$ 62 and $V_{SW}$ 63. $V_{ANODE}$ 61 is monitored by controller 51 by way of analog interface 49 while $V_{MAIN}$ 62 powers at least a portion of each of circuits 15, 45, 47, 48, 49 and 51. $V_{SW}$ 63 is a power supply that is switched under the control of a PDC line 52 from controller 51 in order to allow interlock 1 to operate in a low power drain or "standby" state to conserve the battery of the vehicle especially during prolonged periods of non-use. For that reason, $V_{SW}$ 63 supplies power to audio output 50, sampling head 3 (via heater control/analog interface 49) and to a portion of vehicle interface 45. Power supply 46 also includes an interlock chassis connection 66 and ground 67. The ground 67 is connected to each of the circuits 15, 45, 47, 48, 49, 50 and 51. To minimize noise, the ground 67 associated with the analog circuits should be run separately from those associated with digital components. The operation of beeper 8 is controlled by way of a line AOC 65 connected between controller 51 and audio output circuit 50 as will later be explained in further detail with reference to FIG. 11.

Vehicle interface 45 is connected to controller 51 by way of lines designated ILK 68, HRN 69 and IGN 70. ILK line 68 is controlled by controller 51 in order to selectively enable and disable starting of the vehicle. The HRN line 69 is used to allow controller 51 to sound the horn of the vehicle while IGN line 70 is used for two purposes. In the first instance, it allows controller 51 to sense whether the vehicle ignition switch is off or in its RUN position. When interlock 1 is not in operation and is being serviced, line IGN 70 is used as a communication line between second remote service device 56 and controller 51 via remote interface 47. As will later be elaborated upon, such communications are further facilitated by three lines; RST 73, SRS 74 and SCL 75 which are connected between controller 51 and remote interface 47. RST line 73 is also connected to power supply 46 to permit resetting of controller 51 in the event a low voltage condition occurs.

As will be explained further with reference to FIG. 10, operator interface 15 is connected to controller 51 by way of lines designated MTE 76, PWR 77 and MDE 78 emanating, respectively, from push buttons 20, 19 and 21 while a line designated IND 79 connects controller 51 with LED indicator 23 and a series of lines BG∅ through BG9 80 through 89 (FIG. 5), respectively connect controller 51 with each respective LED 25 through 34 making up bar graph display 22. It will be noted that line BG∅ 80 is also used by controller 51 to transfer data to non-volatile memory 48 (i.e., write to memory) while a line EDO 92 is used to transfer data in the reverse direction from memory 48 to controller 51 (i.e., read from memory). These functions are assisted by lines ECS 93 and AD6 94 which are used respectively as chip select and clock lines for memory 48. Line AD6 94 is also used as a clock line for the analog interface portion of circuit 49. Heater control/analog interface circuit 49 also includes a number of other connections to controller 51. These include lines AD1 96, AD2 97, AD4 98, AD5 99 and HTC 100.

Sampling head 3 is connected to controller 51 by way of cable 4 which includes lines RDY 101 and PSW 102 and is connected to heater control/analog interface 49 by way of lines; SEN 103, FBK 104, HTR1 105 and HTR2 106 as well as connections to power supply $V_{SW}$ 63 and ground 67. These lines will be discussed in further detail with particular reference to FIGS. 5, 8 and 9.

Vehicle Interface

Referring additionally now to FIG. 3, vehicle interface 45 and its connections to portions of a vehicle electrical system 115 are illustrated in further detail with components of vehicle electrical system 115 being shown in broken lines. Wiring pigtail 10, which carries connector 11 on one end, terminates at its opposite end on a printed circuit board 107 upon which each of: vehicle interface 45, power supply 46, remote interface 47, audio output 50, non-volatile memory 48, controller 51 and heater control/analog interface 49 are all at least partially carried. Connector 11 mates with connector 59 of wiring harness 58 which is wired to components of vehicle electrical system 115 in the manner shown. In particular, electrical system 115 includes a battery 108 whose positive terminal 109 is wired to line 58a and whose negative terminal 110 is wired to line 58b as well as wire 58c which is connected to both the chassis 111 of the vehicle the ground side 112 of the vehicle starter solenoid 113. The opposite side 114 of solenoid 113 is connected to wire 58g. The positive terminal 109 of battery 108 is also connected to the line side 116 of the vehicle horn relay coil 117 as well as two pairs of contacts 119, 120 associated the vehicle ignition switch. Contacts 119 comprise a set of normally open contacts that are maintained closed when the vehicle ignition switch is in a RUN position. Contacts 120 are normally open contacts that are momentarily closed while the vehicle ignition switch is held in a START position as it is when attempting to start the vehicle. As can be seen, the load side of contacts 119 are wired to line 58d. IGN line 70 is formed by connection of line 10d to a voltage divider made up of resistors 122 and 123 the output of the voltage divider being clipped by a Zener diode 124 to limit the maximum voltage appearing on line IGN 70 in accordance with the rating of diode 124. Thus, the voltage appearing on line IGN 70 can be sensed directly by controller 51 to determine whether or not the vehicle ignition switch contacts are in their RUN position.

To control the horn (not shown) of the vehicle, line 10e, which is connected to horn relay coil 117 through wire 58e, is selectively pulled low by transistor 126 the drain of which is connected to line 10e and also ultimately to the positive terminal 109 of battery 108 by way of line 10a through a transient suppressing diode 127. Transistor 126 is itself controlled by controller 51 according to the signal appearing on HRN line 69 which is applied to the base of a bipolar NPN driving transistor 128 through a series resistor 125. The collector of transistor 128 is connected to the gate of transistor 126 such that when controller 51 pulls HRN line 69 low, transistor 128 is cut off and its collector is pulled up by a resistor 129 which connects the collector of transistor 128 to supply $V_{SW}$ 63. This causes transistor 126 to conduct thereby completing the circuit from coil 117 to ground in order to cause the horn to sound. It is noted that transistor 128 is supplied from switched power supply $V_{SW}$ 63. Thus, sounding of the vehicle horn is disabled whenever controller 51 causes power supply $V_{SW}$ 63 to be turned off in order to conserve battery 108. To ensure that the vehicle horn does not sound during power up of interlock 1, a pullup resistor 121 is connected between HRN line 69 and the $V_{MAIN}$ power supply 62. It should be noted that the vehicle horn can still be operated manually by way of the vehicle horn button (not shown) for signaling by the operator. However, HRN line 69 can override the vehicle horn button so that the horn can be sounded under the control of controller 51 regardless of whether the horn button is pressed by the operator. As will be seen, this capability is used in the event an operator fails to take a timely retest in the event one is required.

Starting of the vehicle is selectively enabled and disabled under the control of controller 51 by way of line ILK 68 which is connected by way of a resistor 133 to the base of a Darlington transistor 130 whose collector is coupled to the coil of an ignition interlock relay 131 that is shunted with a protective diode 132. Relay 131 has a normally open contact connected in series with vehicle ignition switch contacts 120 by way of wires 58f and 10f as well as with the non-grounded side 114 of ignition solenoid 113. Thus, starting of the vehicle is enabled when ILK line 68 is pulled low by controller 51 thereby causing transistor 130 to conduct which energizes relay 131 causing its contact to close so that the vehicle operator can start the vehicle by applying power from battery 108 to solenoid 113 through ignition switch contacts 120.

Power Supply

With additional reference now to FIG. 4 power supply 46 will now be described in further detail. The positive and negative terminals 109, 110 of battery 108 are connected by way of lines 10a and 10b to a filter network 134 which includes series inductors 135 and 136 and parallel capacitors 137 and 138 which are connected together at a node linked to line 10c as shown. The line side of inductor 136 is connected to the chassis ground point 66 of control module 2 while its load side defines ground 67. Overcurrent protection is provided by a fuse F1 139 connected in series with line 10a while overvoltage protection is provided by a varistor 140 connected across the lines 10a, 10b spanned by capacitors 137 and 138. A reverse current blocking diode 144 is connected in series with the output side of filter network 134 to prevent damage to the circuitry of control module 2 in the event the polarities lines 58a and 58b (FIG. 3) are reversed. The anode of diode 144 defines a filtered but unregulated power supply $V_{ANODE}$ 61 while its cathode defines node $V_{IN}$ 64. A five volt voltage regulator 145 has its input connected to node $V_{IN}$ 64 which is spanned by a capacitor 148. The output of regulator 145 defines regulated +5 volt power supply $V_{MAIN}$ 62 which is spanned by a capacitor 149. Voltage regulator 145 is preferably a type such as an LM2925 manufactured by National Semiconductor which includes a reset pin which can be connected to controller 51 by way of RST line 73 as indicated. In the event regulator 145 cannot maintain its nominal output voltage, regulator 145 pulls line RST 73 low in order to effect a hardware reset of the microprocessor associated with controller 51. A resistor 150 and capacitor 151 are connected to RST line 73 as shown in order to dampen any oscillations which might otherwise occur thereon. A 0.1 microfarad capacitor 152 is connected between pin 4 of regulator 145 and ground in order to determine the duration of the reset signal.

Switched 12 volt power supply $V_{SW}$ 63 is developed by connecting node $V_{In}$ 64 to the source of a field-effect transistor (FET) 153 the drain of which defines supply $V_{SW}$ 63 and the gate of which is connected to the collector of a driving transistor 154 that is connected to $V_{IN}$ 64 by way of a resistor 155. The emitter of transistor 154 is connected to ground 67. The base of transistor 154 is connected to PDC line 52 through a resistor 156. Thus $V_{SW}$ 63 is turned off whenever controller 51 pulls PDC line 52 low. This cuts off transistor 154 so that resistor 155 pulls its collector high thereby cutting off transistor 153 to deenergize supply $V_{SW}$ 63. Conversely, when PDC line 52 is high, supply $V_{SW}$ 63 is turned on.

Microprocessor Controller and Operator Interface

Figure 5:
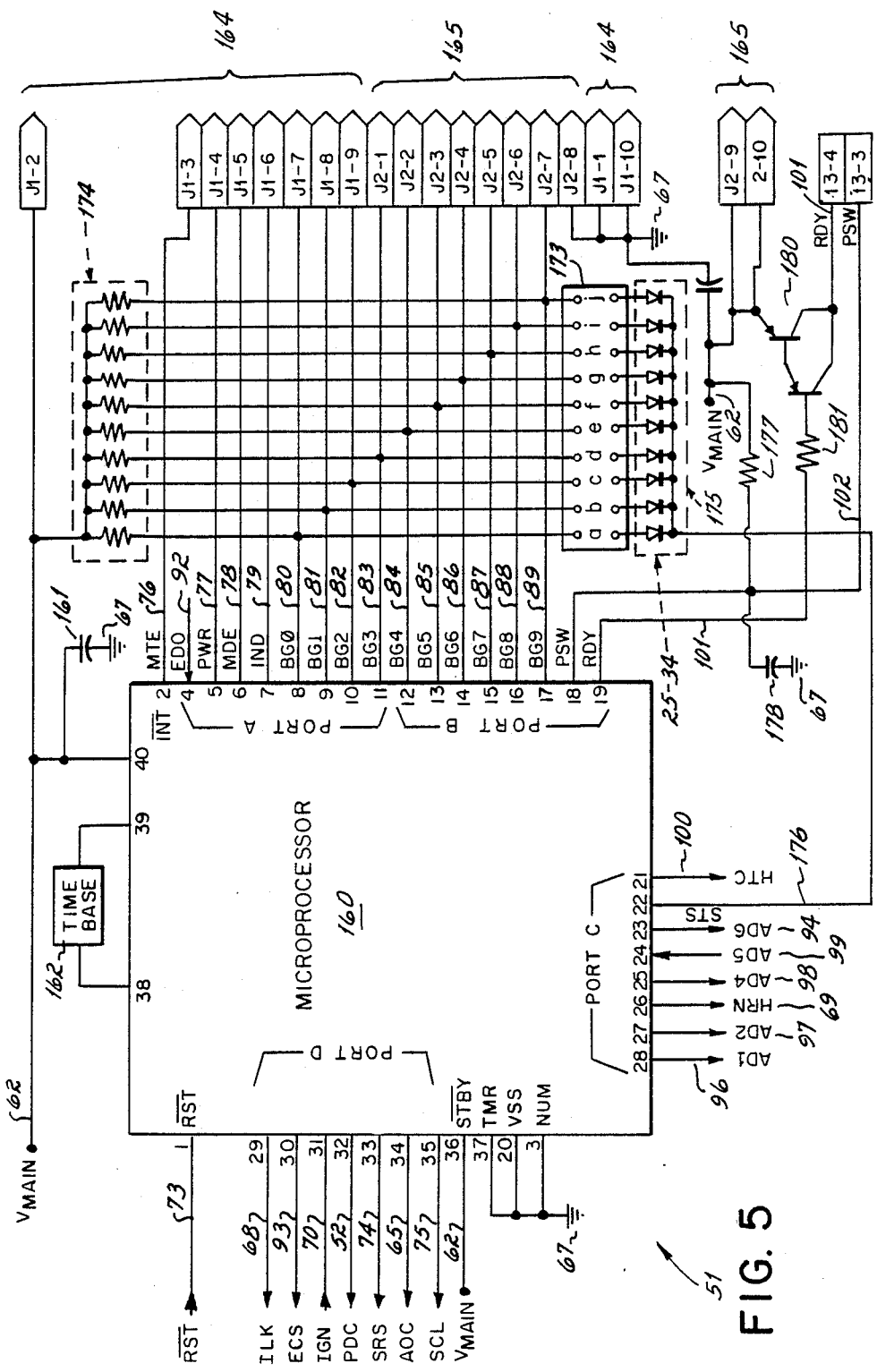
FIG. 5 is an electrical diagram showing further details of the microprocessor controller depicted in block form in FIG. 2.
Figure 10:
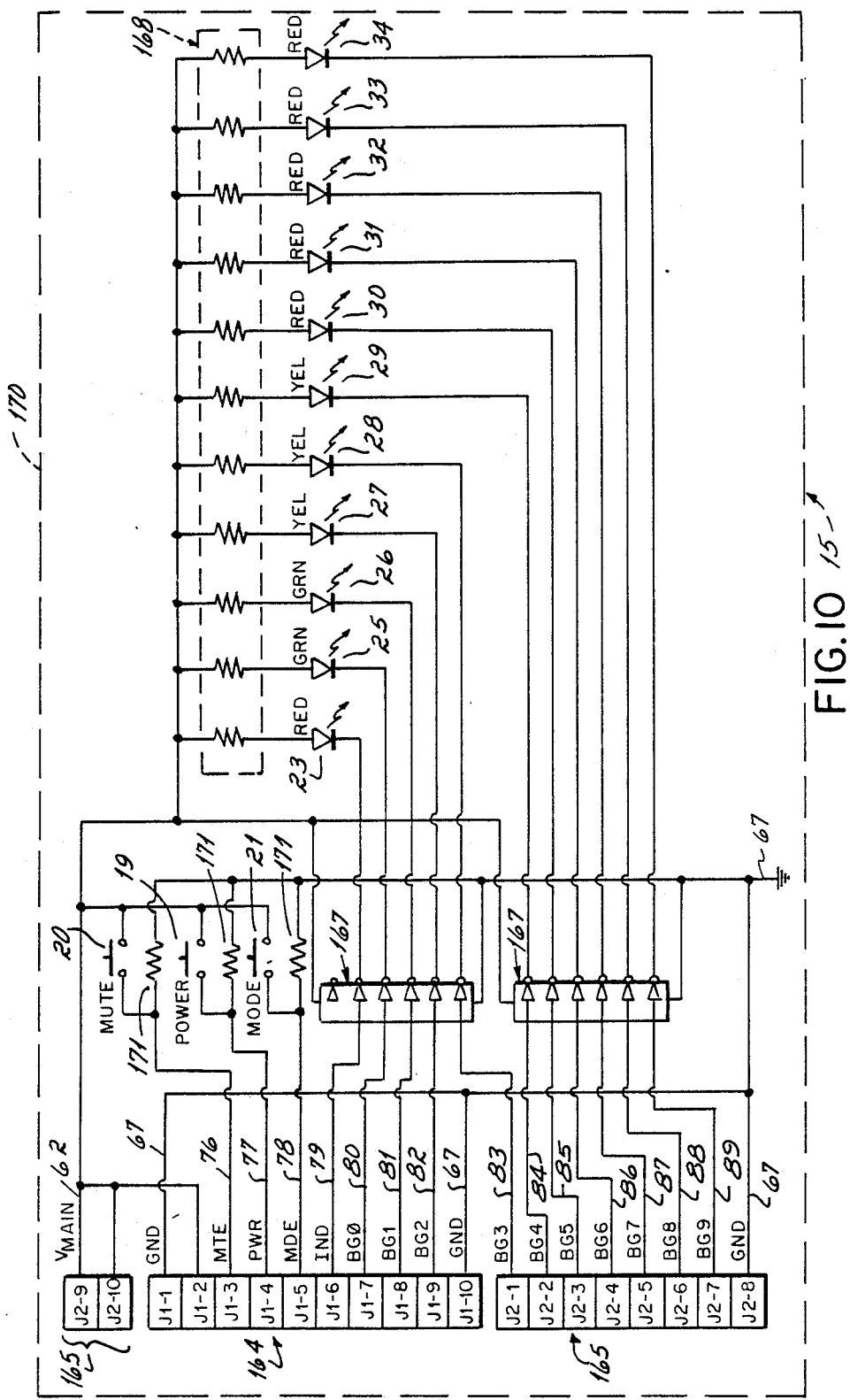
FIG. 10 is an electrical diagram showing further details of the operator interface depicted in block form in FIG. 2.

With reference to FIGS. 5 and 10 controller 51 and operator interface 15 will now be explained in further detail. Controller 51 includes a programmable microprocessor 160 which may suitably comprise a type such as a part number HD637B05VOP manufactured by Hitachi America, Ltd. which is configured as a single integrated circuit having pins numbered consecutively from pin 1 to pin 40. As shown in FIG. 5, microprocessor 160 is supplied power from $V_{MAIN}$ 62 by way of pin #40, which is shunted to ground 67 by way of a capacitor 161, as well as by way of pin #3 which is tied directly to ground 67 as are pin #37 and pin #20. A conventional 4.000 MHz time base 162 is connected across pin #38 and pin #39. To effect a hardware reset of microprocessor 160 by voltage regulator 145 RST line 73 is connected to pin #1. Consecutive pin numbers 29 through 35 of microprocessor 160 define I/O port D and are connected respectively to lines: ILK 68, ECS 93, IGN 70, PDC 52, SRS 74, AOC 65 and SCL 75. These are configured as microprocessor inputs or outputs as indicated by arrows in FIG. 5. The functions of lines ILK 68, IGN 70 and PDC 52 have already been explained. The functions of lines SRS 74 and SCL 75 will be explained more clearly with reference to FIGS. 6, 12 and 13 while those of lines ECS 93 and AOC 65 will be clarified in connection with the descriptions of FIGS. 7 and 11 respectively. Pin #36, which is tied to $V_{MAIN}$ 62, is not used.

Each LED, 25 through 34 making up bar graph display 22 is individually controlled by microprocessor 160 by way of lines BGØ 80 through BG9 89. Those lines are connected to microprocessor 160 by way of microprocessor pin numbers 8 through 17 respectively. Connection of lines BGØ 80 through BG9 89 to corresponding LEDs 25–34 are made by way of male and female connectors J1 164 and J2 165 each having pins numbered 1 through 10. The male pins of connectors J1, 164, and J2, 165 are shown in FIG. 5 while the correspondingly numbered female pins are depicted in FIG. 10. (Note that FIG. 5 also shows pins 3 and 4 of eight pin receptacle 13 the remaining pins of which are shown in FIG. 8). As can be seen from FIG. 10, each of lines BGØ 80 through BG9 89 is connected to the cathode of each respective LED 25 through 34 by way of one of a series of buffers 167. One of the same buffers 167 similarly connects the cathode of indicator LED 23 to pin 7 of microprocessor 160 by way of line IND 79. The anode of LED 23 as well as those of LEDs 25–34 is connected to power supply $V_{MAIN}$ 62 through one of a series of resistors 168.

Operator interface 15 is mounted on a separate printed circuit board 170 from the printed circuit board 107 carrying the remainder of the electronics within control module 2. Circuit board 170 receives its power from supply $V_{MAIN}$ 62 by way of pins 9 and 10 of connector J2 165 as well as pin 2 of connector J1 164. Circuit board 170 receives ground 67 by way of pins 1 and 10 of connector J1 164 as well as pin 8 of connector J2 165.

Figure 7:
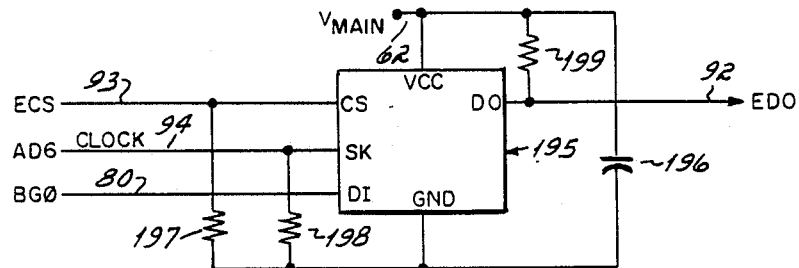
FIG. 7 is an electrical diagram showing further details of the non-volatile memory depicted in block form in FIG. 2.

The push buttons on front panel 6 designated POWER 19, MUTE 20, and MODE 21 are each normally open, momentary, single pole, single throw types and has its line side connected to supply $V_{MAIN}$ 62 and load side connected to lines PWR 77, MTE 76 and MDE 78 respectively. Those lines are carried to circuit board 170 from circuit board 107 through connector J1 164 by way of pins 4, 3 and 5 respectively as shown in FIG. 7. For noise immunity, the load side of each push button 19, 20, 21 is connected to ground 67 by way of a pull down resistor 171. As can be seen from FIG. 5, lines MTE 76, PWR 77 and MDE 78 are connected, respectively to pins 2, 5 and 6 of microprocessor 160. Those pins are configured as inputs whereby microprocessor 160 can sense the pressing of each push button 19, 20 and 21 by a person.

In addition to being used as outputs for selectively lighting the LEDs 25–34 making up bar graph display 22, lines BG∅ 80 through BG9 89 are also momentarily used as inputs to microprocessor 160. As will be noted in connection with the description of the "BOOT UP" state in the software description which appears later, these lines are also used to read the status of a series of pairs of jumper posts (a through j) which appear in FIG. 5 on a common header 173. Each line BG∅ 80 through BG9 89 is connected to one side of each respective pair of posts (a through j) as well as to power supply $V_{MAIN}$ 62 by way of one of a series of pull up resistors 174. The opposite side of each pair of posts a through j on header 173 are connected, through one of a series of diodes 175 to pin 22 of microprocessor 160 by way of a strap select line STS 176. To read which, if any, of the pairs posts a through j may be shorted with jumper straps, microprocessor 160 momentarily pulls STS line 176 low and reads the logical state of each of lines BG∅ 80 through BG9 89. If any of those lines reads low, it indicates that the corresponding pair of posts is jumpered. The presence or absence of a jumper strap across each pair of jumper posts a through j on header 173 indicates to the microprocessor whether any of several selectable features are to be implemented.

Among these features are the ability of interlock 1 to require a prospective operator to identify himself as being a particular individual. This is preferably accomplished by requiring the operator/test subject to perform what shall be referred to as an "identity-confirming act" which a designated operator has previously been trained to perform correctly and which microprocessor 160 is programmed to recognize. Unless this act is correctly performed within a limited number of attempts in a given time, interlock 1 will not permit the vehicle to be started for some period of time regardless of the result of any alcohol breath test. The limited number of attempts allowed is selected in accordance with the degree of skill required to learn to perform the act correctly such that a person cannot ordinarily learn to perform the act in fewer than that number of attempts. Thus, a previously untrained accomplice will not likely be able to perform the act instead of the designated trained operator in order to evade the test. This technique has been described in detail in commonly assigned U.S. Pat. No. 4,738,333 issued Apr. 19, 1988 and will be assumed to be incorporated in the sobriety interlock 1 being described. As will be explained further with reference to FIG. 19, one preferred embodiment of the identity-confirming act consists of blowing a series of puffs or "bursts" of breath interspaced with pauses into the mouthpiece 40 of sampling head 3 beginning just after the BAC measurement phase of the test is completed. The puffs of breaths and pauses must conform to predetermined timing requirements in order to pass this "ID phase" of the test.

In addition to selecting whether sobriety interlock 1 requires performing an identity-confirming act as a precondition to starting the vehicle, strapable header 173 can also be used advantageously to select other options such as alternate BAC levels at which interlock 1 will provide a WARN indication and/or enable vehicle starting and whether interlock 1 is to require periodic retesting after the vehicle is started regardless of the results of previous breath tests.

Returning now to consideration of the structure and basic operation of controller 51, pin #18 of microprocessor 160 is connected to PSW line 102 which extends to sampling head 3 by way of receptacle 13. PSW line 102 is tied to supply $V_{MAIN}$ 62 by way of a pull up resistor 177 and is shunted to ground 67 through a capacitor 178. As will be further explained in connection with FIG. 9, PSW line 102 is connected to means for sensing whether breath is being delivered to sampling head 3 at at least a predetermined minimum flow rate. Accordingly, pin 18 of microprocessor 160 is configured as an input.

Ready LED 41 which is visible exteriorly of sampling head 3 is selectively lighted under the control of microprocessor 160 by way of pin #19 thereof which is connected to RDY line 101. RDY line 101 is driven by a transistor 180 that is controlled through a resistor 181 and supplies current to READY LED 41 from supply $V_{MAIN}$ as shown through pin 4 of connector 13.

The horn of the vehicle is controlled by line HRN 69 in the manner previously described. That line is connected to pin #26 of microprocessor 160 whereas lines AD1 96, AD2 97, AD4 98, AD5 99 and AD6 94 are connected to microprocessor 160 at pin #28, pin #27, pin #25, pin #24 and pin #23 respectively as shown in FIG. 5. Those lines will be discussed further somewhat later in relation to FIG. 8. Each of the aforementioned pins is configured as an output except for pin #24 which serves as an input to microprocessor 160.

Remote Interface

Figure 6:
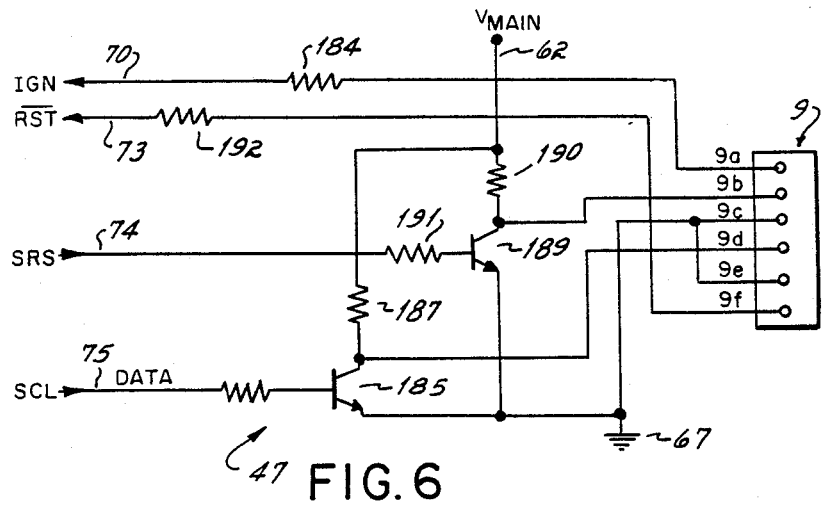
FIG. 6 is an electrical diagram showing further details of the remote interface depicted in block form in FIG. 2.

With additional reference now to FIG. 6, the structure and basic operation of remote interface 47 will now be described. Remote interface 47 provides means for effecting two way communications between interlock 1 and a second remote service device 56. For this purpose, remote service device 56 is connectable to remote interface 47 by way of the female receptacle 9 mounted in the rear panel 7 of control module 2. Receptacle 9 includes six pins which are designated as 9a through 9f as shown.

Communications from remote service device 56 to the microprocessor 160 of interlock 1 are carried by way of pin 9a through a resistor 184 to IGN line 70 which is connected to microprocessor 160 at pin #31 thereof. It should be noted here that remote service device 56 is to be used only by trained, authorized personnel during initial installation or servicing of interlock 1 and at times when the vehicle to which interlock 1 is connected is not running so that IGN line 70 can carry serial digital communications signals. As can be appreciated from the description of vehicle interface 45 provided earlier, IGN line 70 could not be used for communications when the vehicle is running since IGN line 70 is always at a logical high level when vehicle key switch contacts 119 are in their RUN position.

Communication in the opposite direction, that is, from microprocessor 160 to the second remote service device 56 take place by way of line SCL 75 which drives pin 9d of receptacle 9 by means of a transistor 185 whose base is connected to SCL line 75 through a resistor 186. The collector of transistor 185 is connected directly to pin 9d of receptacle 9 and is also connected to power supply $V_{MAIN}$ 62 through a resistor 187. The emitter of transistor 186 is connected to ground 67 which is carried to second remote service device 56 by means of pins 9c and 9e of receptacle 9.

So that proper connection between second remote service device 56 and microprocessor 160 can be assured, microprocessor 160 generates a coded interlock signature signal on line SRS 74. That line is connected to pin 9b of receptacle 9 by way of a driving transistor 189 whose collector is connected directly to pin 9b as well as to supply $V_{MAIN}$ 62 through a pull up resistor 190. The base of transistor 189 is driven by line SRS 74 through a resistor 191. In order to permit second remote service device 56 to perform a hardware reset of microprocessor 160, pin 9f of receptacle 9 is connected through a resistor 192 to RST line 73.

Non-Volatile Memory

With additional reference now to FIG. 7, non-volatile memory 48 will now be described in further detail. Memory 48 includes a non-volatile data storage device such as an electrically erasable, programmable read-only memory (EEPROM) 195 which may suitably comprise a part number HY93C46 manufactured by Hyundai which is a serial device with a 64×16 bit capacity. Memory 195 is supplied power by way of $V_{MAIN}$ 62 and ground 67 with $V_{MAIN}$ 62 being connected to ground 67 by way of a capacitor 196. Line ECS 93 emanating from microprocessor 160 at pin #30 is used as a chip select and is connected appropriately to the CS (chip select) pin of memory 195 as well as to ground 67 by way of a pull down resistor 197. Microprocessor 160 drives ECS line 93 high whenever data is to be either written into or read from memory 195. Memory 195 is clocked by microprocessor 160 by way of line AD6 94 at a pin designated SK which is also linked to ground 67 by way of a pull down resistor 198. Data to be written from microprocessor 160 into memory 195 is received serially at pin D1 (data in) thereof by way of line BG0 80. Similarly, data to be read from memory 195 to microprocessor 160 is carried by way of line EDO 92 which is connected to pin DO (data out) of memory 195. When inactive, line EDO (92) is pulled up to supply $V_{MAIN}$ 62 by way of a resistor R6 199 connected therebetween.

Sampling Head

With additional reference now to FIG. 9, sampling head 3 will now be described in further detail. Sampling head 3 is substantially enveloped within a housing 38 through which READY LED 41 is visible. Housing 38 captures female receptacle 37 the pins of which are designated 37-1 through 37-8 consecutively. Pins 37-1 through 37-8 are connected to eight correspondingly numbered pins 13-1 through 13-8 associated with the female receptacle 13 on the front panel 6 of control module 2. These connections are made by way of cable 4 each end of which carries a male connector 14.

Sampling head 3 includes an alcohol sensor 200 which may suitably comprise one of any number of devices capable of providing an electrical signal that varies predictably with the amount of alcohol to which it is exposed. One suitable type of alcohol sensor is the semiconductor type whose electrical resistance decreases predictably with the amount of alcohol adsorbed onto its surface. Such a sensor 200 is incorporated, along with a heater 202, in a sensor assembly 201. A suitable sensor assembly 201 is made by Figaro Engineering, Inc. of Osaka, Japan and is available commercially in the United States as model TGS-813P from Figaro U.S.A., Inc. of Wilmette, Ill. The structure, operation and mounting of sensor assembly 201 are discussed in further detail in commonly assigned U.S. patent application Ser. No. 07/152,470 incorporated by reference earlier. For present purposes it is sufficient to note that sensor 200 lies in gaseous communication with breath delivered into the inlet port 39 of sampling head 3 by way of mouthpiece 40.

Alcohol sensor 200 has one leg connected to ground 67 and a second leg connected to pin 37-6 by way of a line FBK 104 which includes a calibration potentiometer 205. The node between potentiometer 205 and sensor 200 corresponds to the output of sensor 200 and is carried to pin 37-5 over SEN line 103. Heater 202 has its leads connected to pins 37-7 and 37-8 by way of lines designated HTR1 105 and HTR2 106 as shown.

Sampling head 3 also includes means for sensing breath flow. Pressure switch 208 includes a set of normally open contacts one side of which is connected to ground 67 the other side of which is connected to microprocessor 160 by way of line PSW 102 and connected to pin 37-3 of receptacle 37 (see also FIG. 5). Although other devices including solid state pressure switches or various forms of flow sensors could be used for this purpose a pressure switch 208 has been found suitable. One suitable pressure switch 208 is an electromechanical type such as model PSF-100A04.0 manufactured by World Magnetics of Traverse City, Mich. The structure, mounting and operation of pressure switch 208 are also discussed further in the above-referenced application Ser. No. 07/152,470. For present purposes, it is sufficient to note that the contacts of pressure switch 208 are closed only when the flow of breath delivered to sampling head 3 by an operator through mouthpiece 40 meets or exceeds a desired minimum flow rate. Pressure switch 208 closes to signal microprocessor 160 when the flow of breath delivered into inlet port 39 is at least equal to a predetermined minimum flow. That flow is selected to be sufficient to ensure that a "deep lung" breath sample is delivered to sensor 200 provided such flow or a larger flow is maintained continuously without interruption for at least a predetermined minimum time such as 4.5 seconds. As used herein, the term "deep lung" refers to a breath sample consisting of a proportion of alveolar air sufficient to permit a suitably accurate determination of blood alcohol content (BAC) from such a sample. Pressure switch 208 also conveniently serves as a means for sensing the flow of breath during the various phases of the identity-confirming act described earlier.

Ready LED 41 is wired with its cathode connected to ground 67 while its anode is connected to RDY line 101 at pin 37-4 by way of a resistor 210. Microprocessor 160 controls RDY line 101 such that READY LED 41 flashes when interlock 1 is ready to receive a breath sample. When sample delivery commences as indicated by the closure of pressure switch 208, READY LED 41 stops flashing and remains steadily lighted until a deep lung breath sample has been received whereupon it is extinguished.

An auxiliary heater element 212 and a thermistor 213 are included in sampling head 3 in thermal communication with the flow path through which breath passes. When thermistor 213 senses a sufficiently cold temperature, element 212 is energized as necessary to maintain a sufficient temperature to prevent freezing of moisture in the breath sample. At the same time element 212 tends to maintain the regions adjacent sensor assembly 201 at a relatively stable temperature of about 21° C. in order to avoid an excessively cold operating environment for sensor 200.

Figure 9:
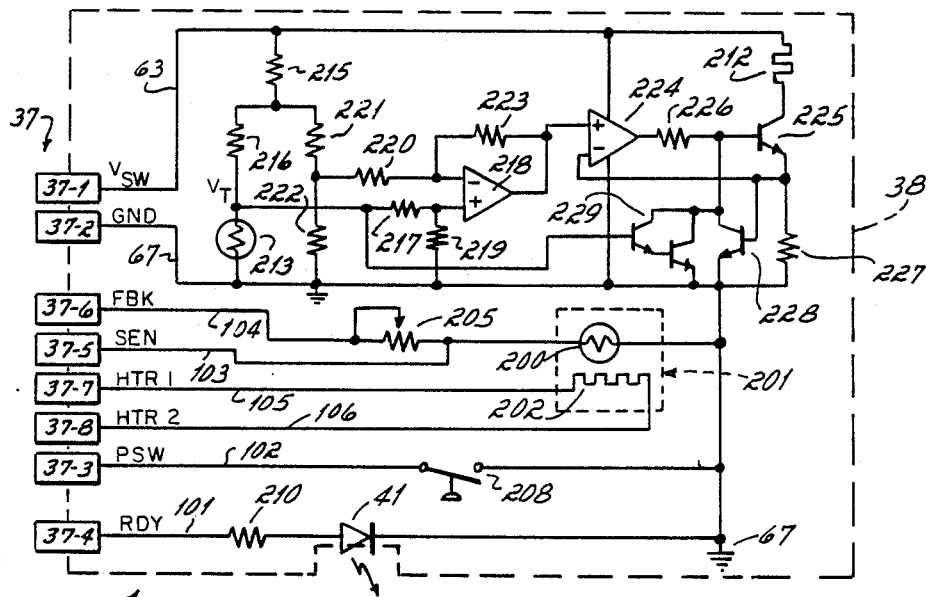
FIG. 9 is an electrical diagram showing further details of the sampling head depicted in block form in FIG. 2.

As shown in FIG. 9, thermistor 213 is connected in series with 150K resistor 215 and 8.2K ohm resistor 216 across supply $V_{SW}$ 63 and ground 67 which are carried from control module 2 by way of pins 37-1 and 37-2 respectively of receptacle 37 to form a voltage divider at node $V_T$. Thermistor 213 is a negative thermal coefficient type such as part number GB41M2 made by Fenwal Electronics Div. of Kidde, Inc. of Framingham, Mass. Node $V_T$ is connected by way of a series 4.7K ohm resistor 217 to the noninverting input of a first amplifier 218 which itself is connected to ground by way of a 220K ohm resistor 219. The inverting input of amplifier 218 is connected by way of a series connected 4.7K resistor 220 to a voltage divider formed by the series combination of resistor 215 together with an 8.2K ohm resistor 221 and an 12K ohm resistor 222 as shown. A 220K ohm feedback resistor 223 connects the inverting input of amp 218 with its output. Thus, amp 218 is configured as a conventional balanced differential amp which amplifies the voltage difference appearing between node $V_T$ and a reference voltage node defined by the junction between resistors 221 and 222. That voltage difference increases as the temperature sensed by thermistor 213 decreases. The base of a transistor 225 is connected to the output of amp 224 by way of a 3.3K ohm resistor 226 while the collector of transistor 225 is connected to one end of element 212 whose other side is connected to supply $V_{SW}$ 63. A 1.5 ohm, 2 watt resistor 227 connects the emitter of transistor 225 to ground 67. The noninverting input of amp 224 is connected to the output of amp 218 while the inverting input of amp 224 is connected across resistor 227 to the emitter of 225 as a means of limiting the current through element 212. A second transistor 228 such as an NPN type 2N3904 has its base connected to the emitter of transistor 225, its collector to the base of transistor 225 and its emitter to ground 67. A Darlington transistor, 229 such as a type MPSA14, in turn has its base connected to node $V_T$, its emitter grounded and its collector connected to the base transistor 225. Normal operation of the circuit controlling element 212 is as follows.

The voltage at node $V_T$ rises as the temperature sensed by thermistor 213 drops and is amplified by amp 218 and upper end limited by amp 224 energizing element 212 with the amount of power required to maintain the thermistor 213 at the temperature determined by resistor 215, 221 and 222. In the event thermistor 213 should open circuit, $V_T$ is pulled up to a voltage that is sufficiently high to turn transistor 229 on thereby pulling the base of transistor 225 to ground 67. This prevents element 212 from being powered. In the event element 212 shorts out, the abnormally high current passing through the collector of transistor 225 would develop a sufficient voltage across resistor 227 to bring transistor 225 into a conducting state, clamping the base of transistor 225 low and thereby limiting the power to element 212. Energization of element 212 is thus independent of microprocessor 160 except to the extent that element 212 can be deenergized by microprocessor 160 by causing $V_{SW}$ 63 to be turned off in the manner described earlier. This occurs when microprocessor 160 operates in a state known as STANDBY in order to conserve vehicle battery 108.

Heater Control/Analog Interface

With additional reference now to FIG. 8 as well as FIG. 9 the circuitry for controlling the heater control/analog interface circuit 49 will now be described.

We turn initially to that portion of circuit 49 which relates to the control of the heater 202 associated with alcohol sensor assembly 201. Heater 202 is supplied power from an 8 volt regulator 232 which may suitably comprise a National Semiconductor part number LM2930 having an input, VI connected to supply $V_{SW}$ 63 across a capacitor 233 an output, VO connected across a capacitor 234 as well as a ground pin connected to ground 67. As previously noted, control module 2 is connected to sampling head 3 by way of correspondingly numbered pins of connectors 13 and 37 which are spanned by cable 13. Power supply $V_{SW}$ 63 is carried on pins 13-1 and 37-1 while ground 67 is carried on pins 13-2 and 37-2. The regulated output of regulator 232 is carried to one side of heater 202 by way of pins 13-7 and 37-7, each of which is connected to line HTR1 105. The opposite side of heater 202 is connected by way of line HTR2 106 and pins 37-8 and 13-8 to the collector of a transistor 237 disposed in a heater control and sensing circuit 238.

Control of the average power applied to heater 202 is effected by applying a variable duty cycle signal to the base of transistor 237 by way of a resistor 239. When transistor 237 is driven into conduction line HTR2 106 is pulled low causing current to flow through heater 202 whereas when 237 is substantially cut off, heater 202 is deenergized. The duty cycle of the signal appearing at the base of transistor 237 is determined by microprocessor 160 which applies an appropriate variable duty cycle signal to HTC line 100. HTC line 100 drives the base of buffer transistor 240 which in turn drives transistor 237. A pullup resistor 241 is connected between the base of transistor 240 and supply $V_{MAIN}$ 62 the latter also being connected to the collector of transistor 240. It can be appreciated that as the duty cycle of the signal generated on HTC line 100 by microprocessor 160 varies so too does the average power applied to heater 202. It should be noted that whenever heater 202 is referred to herein as being "on" or "energized" the voltage waveform applied to heater 202 is a pulse train as opposed to a continuous D.C. signal.

During alcohol sensing, microprocessor energizes heater 202 with a signal having a duty cycle selected to maintain sensor 200 within a desired temperature range of about 390° C. to about 460° C. and preferably closer to 420° C. to 440° C. for best accuracy. If sensor 200 is not substantially within at least the larger of the above temperature ranges, inaccurate measurements can result. Prior to a measurement, sensor 200 is purged to restore its electrical output signal to its equilibrium level, i.e., a level substantially corresponding to zero percent alcohol concentration. This is accomplished under program control by microprocessor 160 which energizes heater 202 with a pulsed signal as required to raise sensor 200 to a temperature which is significantly higher than 460° C. for a time sufficient to cause any alcohol or other impurities adsorbed on the surface of sensor 200 to be oxidized and desorbed therefrom. This process is referred to as "purging" sensor 200.

Provision for determining the continuity of heater 202 and its connections to control module 2 are also provided by circuit 49. It can be appreciated that because line HTR2 106 is switched by transistor 237 that a signal having an A.C. component will be present across line HTR2 106 and ground 67. At circuit 238, that signal is applied to a series capacitor 243 to block any D.C. component thereof and any negative-going portion of the waveform is clipped off by a parallel diode 244 and half-wave rectifier 245. The anode of rectifier 245 is connected to one side of a D.C. storage capacitor 246 the other side of which is connected to ground 67. The voltage across capacitor 246 is limited to about 4.7 volts by a Zener diode 247 and is applied to a heater sensing line HSN 248.

It can be appreciated from the foregoing that when heater 202 is continuous (i.e., not open circuited) and is being continuously pulsed by way of line HTR2 106, that a D.C. voltage will normally appear across capacitor 246 and on line HSN 248. In the event heater 202 burns out or becomes disconnected, or if transistor 237 shorts or becomes open circuited, the D.C. voltage appearing across capacitor 246 will drop. This voltage drop can be sensed by microprocessor 160 by way of the analog interface portion of circuit 49 which will be described below.

The analog interface portion of circuit 49 provides three multiplexed channels for converting analog information to digital form and communicating it to microprocessor 160. For this purpose an eight into one multiplexer (MUX) 250 having three active inputs designated X$\emptyset$, X1 and X3 and a single output designated X is provided. MUX 250 may suitably comprise a device such as part number CD4$\emptyset$93BCN manufactured by National Semiconductor. Microprocessor 160 selects a given one of channels X$\emptyset$-X3 by way of lines AD1 96 and AD2 97 which are connected to MUX 250 at its channel select inputs A and B respectively. A third channel select input (C) of MUX 250 is tied to ground 67. Depending on which of channels X$\emptyset$-X3 is selected by microprocessor 160, the corresponding analog signal appears at the output, X of MUX 250 on a line 251 that is connected to the VI+ input of a serial analog to digital converter (A/D) 253. A/D 253 converts the analog signal to serial digital form which is carried to microprocessor 160 by way of line AD5 99. A/D 253 may suitably comprise a device such as part number ADC$\emptyset$831CCN also made by National Semiconductor.

Lines AD4 98 and AD6 94 emanating from microprocessor 160 are connected to A/D 253 and serve as chip select and clock lines respectively. A 2.5 volt reference signal is applied to a VI- input of A/D 253 by way of a line 255 while a 1.5 volt reference signal is applied to a reference input, $V_{REF}$ of A/D 253 by way of a line 256. The 2.5 volt reference on line 255 is developed at the anode of a Zener diode 258 which is connected to supply $V_{MAIN}$ 62 by way of a resistor 259. The 1.5 volt reference on line 256 is developed by way of a voltage divider defined by precision resistors 260 and 261. The 1.5 V reference is applied to a buffer 262 whose output is connected to line 256 as shown.

Channel X$\emptyset$ of MUX 250 is used to carry the output signal of alcohol sensor 200 which appears at the output of a feedback amplifier 265 whose noninverting input is tied to the 2.5 volt reference appearing on line 255 and whose inverting input is tied to pin 13-5 of connector 13 by way of sensor line 206. As can be seen clearly in FIG. 9, sensor line 206 carries the output of alcohol sensor 200. By further inspection of FIGS. 8 and 9 it can be appreciated that calibration potentiometer 205 is connected by way of FBK line 204 in a feedback path between the output of amplifier 265 and its inverting input. The analog voltage appearing at channel X$\emptyset$ on line FBK 104 is approximated by the expression:

$$V_{SENSOR} = 2.5 + KC$$

where K represents a constant and C represents the concentration of alcohol. The 2.5 term is cancelled by A/D 253 owing to the connection of line 255 to the 2.5 volt reference. In order to set the constant K to unity, calibration potentiometer is adjusted until the digital output of A/D 253 corresponds to a value of 100 when sensor 200 is exposed to a gas source having a known concentration of ethanol corresponding to 0.1 gram percent BAC (0.1 grams of alcohol per 100 milliliters of blood).

Channel X1 of MUX 250 is used to monitor the voltage appearing at $V_{ANODE}$ 61. This is accomplished by tying supply $V_{ANODE}$ 61 to a voltage divider comprising precision resistor 267 (36.5K ohm plus or minus 1%) and resistor 268 (12.1K ohm plus or minus 1%). The junction of resistors 267 and 268 are applied to a buffer 270 whose output is tied directly to the X1 channel input of MUX 250. Thus, whenever channel X1 of MUX 250 is selected by microprocessor 160, the digital value output to microprocessor 160 by way of line AD5 99 will correspond to the voltage appearing at supply $V_{ANODE}$ 61. Channel X1 of MUX 250 is used to sense the voltage appearing at supply $V_{ANODE}$ 61 for five purposes.

First, when interlock 1 is initially installed in a vehicle the vehicle is started and $V_{ANODE}$ 61 is read by microprocessor 160 and a threshold voltage value, RUNVLT which is slightly lower than the value read at $V_{ANODE}$ 61 is stored in memory. During subsequent normal operation of interlock 1, RUNVLT is periodically compared with the present sensed voltage at $V_{ANODE}$ 61. If the sensed voltage at $V_{ANODE}$ 61 is greater than the stored RUNVLT value and IGN 70 is high, microprocessor 160 decides that the vehicle is running. Otherwise, the vehicle is assumed to be not running. $V_{ANODE}$ 61 is also sensed by microprocessor 160 for a third purpose. When the vehicle is not running and a predetermined voltage drop appears at $V_{ANODE}$ 61, microprocessor 160 powers up interlock 1 just as though POWER push button 19 had been pressed. The sensed voltage drop is caused by the automatic turning on of the vehicle dome light or other vehicle accessories upon opening the vehicle's door. By powering up immediately upon opening the vehicle door rather than waiting for the operator to push POWER push button 19, the wait for interlock 1 to prepare itself for a test is reduced for the convenience of the operator/test subject. A fourth purpose for sensing $V_{ANODE}$ 61 is to ensure that adequate voltage is present during the BOOT UP state to permit accurate reading of any jumper straps present on header 173. This will become more clear in light of the description of the BOOT UP state illustrated in FIG. 15. $V_{ANODE}$ 61 is also sensed to determine whether the supply voltage remains within acceptable limits. This function is described in further detail later in connection with FIG. 31.

To monitor heater 202, line HSN 248 is applied to the inverting input of a comparator 272 whose other input is tied to the 1.5 volt reference appearing at the output of buffer 262. The output of comparator 272 is tied directly to the channel X3 input of MUX 250. In the event that heater 202 burns out or becomes open circuited or transistor 237 shorts out or becomes open circuited, the voltage appearing on line HSN 248 will fall below 1.5 volts. This will cause the output of comparator 272 to assume a logical high value which can be sensed by microprocessor 160 by way of MUX 250 and A/D 253 when channel X3 of MUX 250 is selected. It should be noted that comparator 272, amp 265 and buffers 262 and 270 all are formed using a single quad op amp IC. The connection of that IC to power supply $V_{MAIN}$ 62 should be bypassed to ground 67 by way of a small capacitor (not shown) located physically adjacent the device for the purpose of improving noise immunity. Similar small grounded capacitors (also not shown) should be added adjacent MUX 250 and A/D 253 at their respective connections to power supply $V_{MAIN}$ 62.

Audio Output

With additional reference now to FIG. 11 audio output 50 will now be described in further detail. Quite simply, audio output 50 includes an audio amplifier 275 having a pair of inputs. The inverting input is connected directly to ground 67 and the noninverting input is connected to microprocessor 160 by way of AOC line 65. AOC line 65 feeds a voltage divider comprising resistors 276 and 278. This voltage divider is in turn connected to the non-grounded input of audio amplifier 275 through an A.C. coupling capacitor 277. Amplifier 275 may suitably comprise an integrated circuit audio amplifier such as part No. LM386N manufactured by National Semiconductor. Amplifier has its output connected by way of a capacitor 279 to beeper 8 which may suitably comprise a small 8 ohm speaker. Pin 6 of amplifier 275 is connected to power supply $V_{SW}$ 63 which is shunted to ground by way of a capacitor 280 while pin 7 of amplifier 275 is connected to ground 67 by way of a capacitor 281 and pin 4 is connected directly to ground 67. As can be appreciated from the foregoing description, the sound generated by beeper 8 is determined by the manner in which microprocessor 160 pulses AOC line 65. Thus, microprocessor 160 can cause beeper 8 to produce a variety of audibly distinctive tones or tone sequences to provide audible signals to a user of interlock 1.

This concludes the description of the hardware and basic electrical operation of sobriety interlock 1. Before proceeding to consider the software and further details of the operation of interlock 1 in detail it is appropriate now to consider remote service devices 55 and 56.

REMOTE SERVICE DEVICES

To facilitate installation and periodic service of interlock 1 it is convenient to provide one or more remote service devices capable of communicating with interlock 1 in order to perform a number of functions including:

(a) setting a service reminder timer (the current value of which is hereinafter specified according to the parameter TIME);

(b) reading the service reminder timer, TIME;

(c) reading and/or storing the run voltage threshold value, RUNVLT which, as previously noted is periodically compared with a representation of the current voltage at $V_{ANODE}$ 61 as part of the procedure for determining whether the vehicle is actually running;

(d) reading out a stored record indicating events when the vehicle was started by bypassing interlock 1; and (e) clearing recorded bypass events.

According to the preferred embodiment described herein, the service reminder timer, TIME is a timer implemented in software which measures real time upon being decremented at one day intervals. TIME is initially set or is reset to equal a desired number of days measured from the present day when servicing of sobriety interlock 1 is due. If an optional grace period for obtaining service is to be provided, the length of the grace period in days is added to the aforementioned number of days. The operation of sobriety interlock 1 as TIME decrements to various predetermined values will be described in further detail hereinafter particularly with reference to FIGS. 14, 17 and 28.

As noted earlier, the term "bypass event" refers to any occurrence whereupon the vehicle or other machine to which a sobriety interlock is connected is started without satisfying one or more preconditions the interlock normally requires to be satisfied before it will permit the vehicle to be started. For example, a bypass event occurs if the vehicle is initially started without at least a substantially contemporaneous breath sobriety test being passed. A bypass event is also deemed to occur where, after running for some time, the vehicle stalls or is turned off and is subsequently restarted without a retest after at least one predetermined time limit has expired. Where, as in the case of the preferred embodiment described herein, the sobriety interlock imposes one or more additional preconditions to starting the vehicle, such as requiring the operator/test subject to identify himself or herself as a designated individual, a bypass event optionally can be and preferably is recorded when the vehicle is started without such additional preconditions also being satisfied.

The record of bypass events, at a minimum, indicates that a bypass event has occurred. Preferably, the record includes additional useful information such as the total number of bypass events occurring since a specified time (such as when interlock 1 was last installed or serviced). That parameter is hereinafter referred to as TOTBYP. It is also desirable for the record to indicate the day(s) during which at least one bypass event occurred. Such days are conveniently specified in terms of a parameter, DAY, the value of which equals the value of the service reminder timer, TIME that was current as of when the bypass event was detected. The record also preferably specifies the number (designated hereinafter by the parameter NUMBER) of separate bypass events detected during each recorded DAY. Each NUMBER value is preferably stored and read in association with its corresponding DAY value in the form of a DAY/NUMBER couplet.

In addition to together serving the functions listed above either or both remote service devices 55, 56 can be endowed with the ability to perform diagnostics or other ancillary functions not related to the present invention. Since it is undesirable to permit persons other than trained authorized service personnel to tamper with the above functions, possession of remote service devices should be limited to authorized personnel.

First Remote Service Device

As indicated in FIG. 2, first remote service device 55 is connectable to the female receptacle 13 in the front panel 6 of control module 2 when sampling head 3 is disconnected therefrom. Remote service device 1 includes a female receptacle 285 identical to the receptacle 37 associated with sampling head 3 so that first remote service device 55 can be connected to control module 2 using cable 4. First remote service device 55 consists of a code generator that generates a code on line PSW 102 identifiable by microprocessor 160. Because it is characteristic of remote service device 55, this code shall be referred to as the "RSD 55 signature". When microprocessor 160 recognizes the RSD 55 signature appearing on line PSW 102 and MODE push button 21 is pressed, microprocessor 160 enters a restricted access state which shall be referred to as "S1". In the S1 state, the MODE, POWER and MUTE push buttons 19, 20 and 21 together with display 22 can be used to reset the service reminder timer to one of several available settings such as 97, 67 or 37 days (depending on when the next service is desired) as well as to cause microprocessor 160 to read and store a run voltage checking threshold, RUNVLT. During subsequent operation of interlock 1, the vehicle will be assumed to be running whenever IGN line 70 is high and the voltage appearing at $V_{ANODE}$ 61 is greater than the stored run voltage threshold RUNVLT. Operation of interlock 1 in the S1 state will be described in further detail in connection with the interlock software and operational description which follows somewhat later.

Second Remote Service Device

With additional reference now to FIG. 12 as well as FIGS. 2, 5 and 6, second remote service device 56 will now be described in further detail. Second remote service device 56 includes a power supply 287 which may be either fully self-contained or adapted for connection to an A.C. source by way of a grounded line cord 288. Power supply 287 produces a regulated +5 Volt output that is connected to an audio output section 290 that is constructed and operates in a fashion analogous to audio output 50 previously described in connection with FIG. 11. Control of audio output 290 is effected by a microprocessor 291 by way of an audio control line ACL 292. Microprocessor 291, which may suitably comprise a Hitachi part number HD637B05VOP, is connected to power supply 287 by way of a power switch 294 as is a control panel 295 and audio output section 290. Control panel 295 includes an alphanumeric liquid crystal display 298, a FUNCTION push button 299, a RUN/CL push button 300, a SELECT push button 301, and an error indicator LED 302.

Communication between control panel 295 and microprocessor 291 are effected by way of a communication bus 305 whereas communication between second remote interface device 56 and interlock 1 are effected by way of a cable 307 (FIG. 2) which connects the female receptacle 9 of remote interface 47 with an identical female receptacle 308. It will be recalled that receptacle 9 includes 6 pins designated 9a through 9f. In a like manner, connector 308 includes 6 corresponding pins designated 308-a through 308-f. Pins 308-c and 308-e carry ground 67 to which each of power supply 287, audio output 290, microprocessor 291, and control panel 295 are all referenced. Microprocessor 291 is connected to pins 308-a, 308-b, 308-d, and 308-f by way of lines designated IGN' 309, SRS' 310, SCL' 311 and RST' 312 respectively. Those lines are connected by way of cable 307 and remote interface 47 to lines IGN 70, line SRS 74, line SCL 75 and line RST 73. Line IGN' 309 is used to carry communications from microprocessor 291 to microprocessor 160 while communications from microprocessor 160 to microprocessor 291 are carried by way of line SCL' 311. Line RST' 312 is used by microprocessor 291 to effect a hardware reset of microprocessor 160 while line SRS' 310 carries the unique, encoded interlock signature signal which, as mentioned earlier, identifies interlock 1.

Having described the hardware associated with second remote service device 56, its software and further details of its operation will now be described with reference to FIGS. 13A through 13F.

Second Remote Service Device Software and Operational Description

Figure 13A:
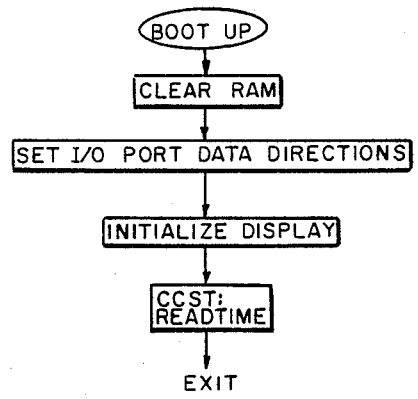

Referring initially to FIG. 13A, microprocessor 291 enters a BOOT UP state upon closure of power switch 294. In BOOT UP, microprocessor 291 clears all necessary random access memory (RAM) and sets the data directions of the I/O lines associated with bus 305 as well as lines 309 through 312 and ACL line 292. Display 298 is then initialized and the current software state, i.e., BOOT UP, is changed to the READTIME stage to be described below with reference to FIG. 13B. In the flowcharts, the abbreviation "CCST" is used to indicate "change current state to:". For instance, the last block of FIG. 13A indicates that the BOOT UP state changes to the READTIME state at that point.

Figure 13F:
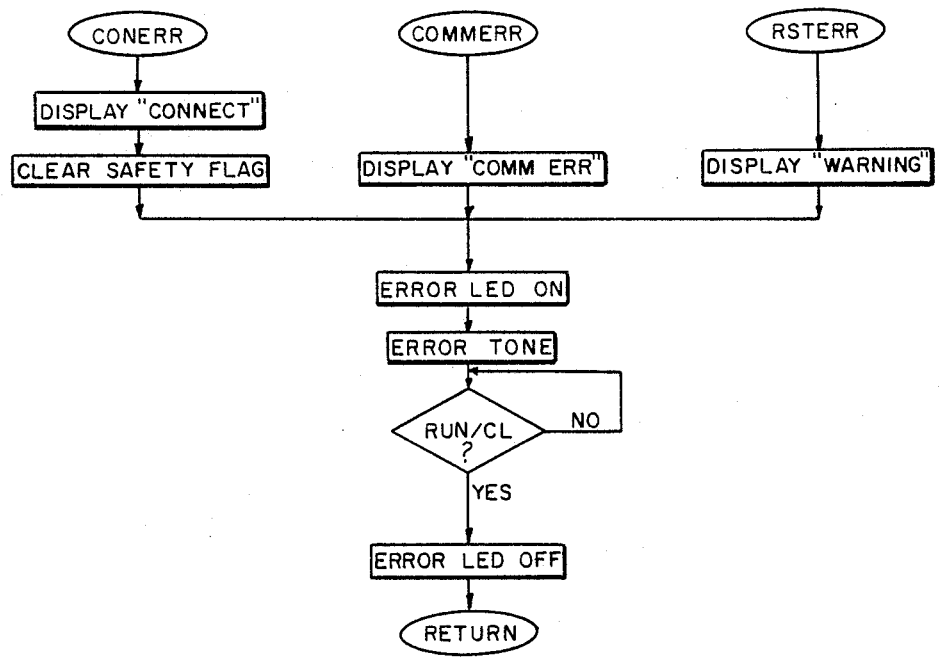
Figure 13B:
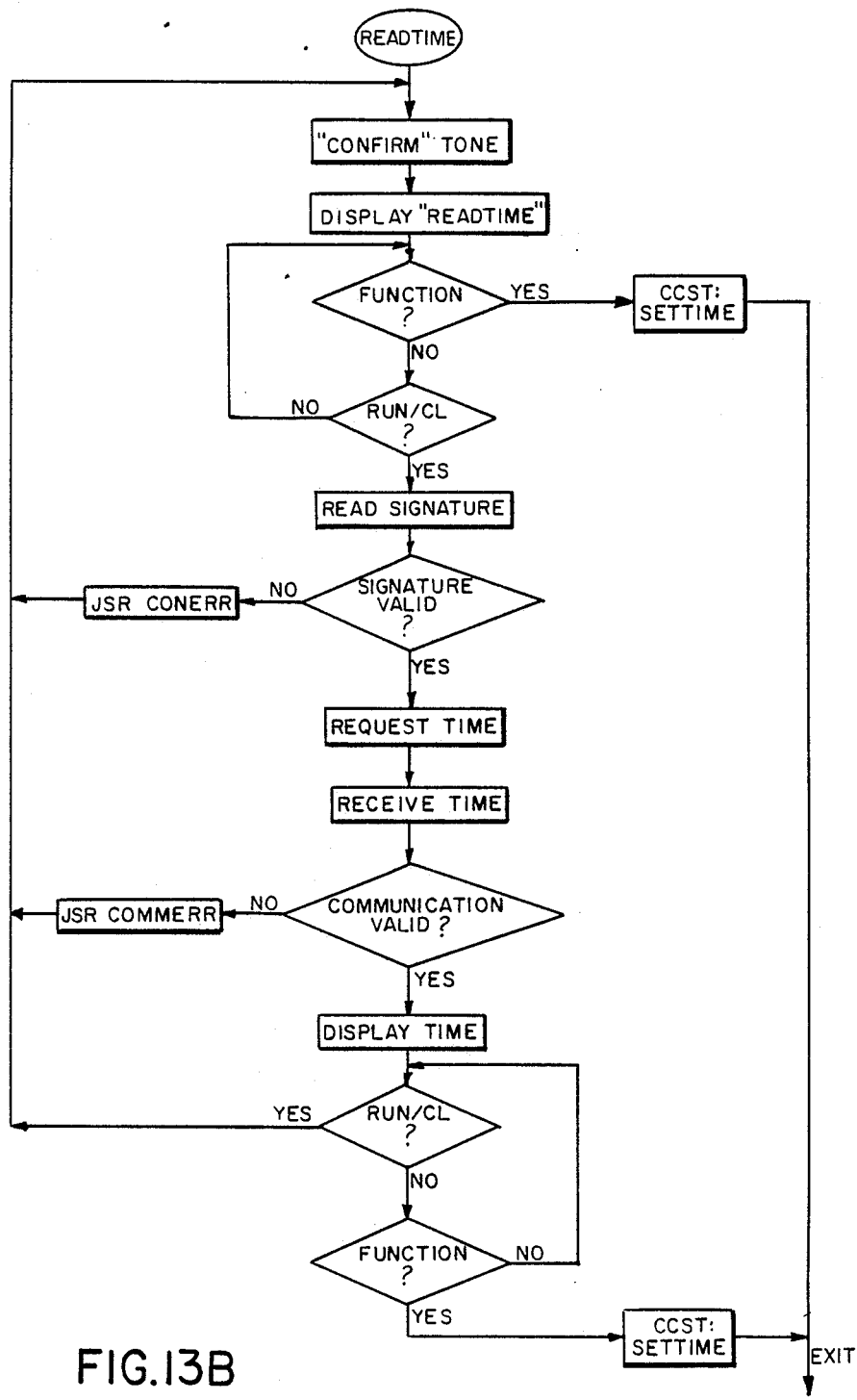

With attention now to FIG. 13B the READTIME state, like all operational states to be described is initiated by the sounding of a distinctive "confirm" tone by way of audio output 290. This tone is initiated by microprocessor 291 which controls audio output 290 by way of ACL line 292. Microprocessor 291 then causes a mnenonic such as the word "READTIME" to appear on display 298 as an indication that second remote service device 56 is prepared to read the current value of the service reminder timer from microprocessor 160. If a service person desires to perform some other function, such as setting the service reminder timer to a desired number of days, function button 299 is pressed whereupon microprocessor 291 enters the SETTIME state to be described below with reference to FIG. 13C. Otherwise, RUN/CL push button 300 is actuated causing microprocessor 291 to read line SRS' 310. When second remote service device 56 is properly connected to an operational interlock 1, a coded signature signal generated by microprocessor 160 and recognizable by microprocessor 291 will appear on line SRS' 310. If the signature is not recognized the program jumps to an error subroutine, CONERR, which will be described later in connection with FIG. 13F. For the present it is sufficient to note that CONERR provides an indication that device 56 is not properly connected to an operational sobriety interlock 1. Once the signature is recognized, a request for the current value of the service reminder timer is requested by microprocessor 291 by way of line IGN' 309. In response to the request, microprocessor 160 transmits a communication which includes a series of bits representing the TIME value as well as a command word. Upon receipt of this communication, microprocessor 291 performs a validity check by comparing the command word with a stored list of commands to be sure it corresponds to a valid command. A parity check or other desired checks may also be performed. If the communication is valid the current value service reminder timer, TIME is displayed on display 298. TIME is an integer value representing the number of days remaining until TIME equals zero. In the event the command word is not recognized or a parity error occurs, a second error subroutine, COMMERR, is entered. COMMERR, which will also be described further with reference to FIG. 13F, serves to indicate a communication error has occurred. Assuming that COMMERR is not entered, repeated pressing of the RUN/CL push button 300 will cause the above steps to be repeated whereas pressing of FUNCTION push button 299 will cause second remote service device 56 to enter the SETTIME state wherein the value of the service reminder timer, TIME of microprocessor 160 can be set to any integer value from zero to 255 days.

Figure 13C:
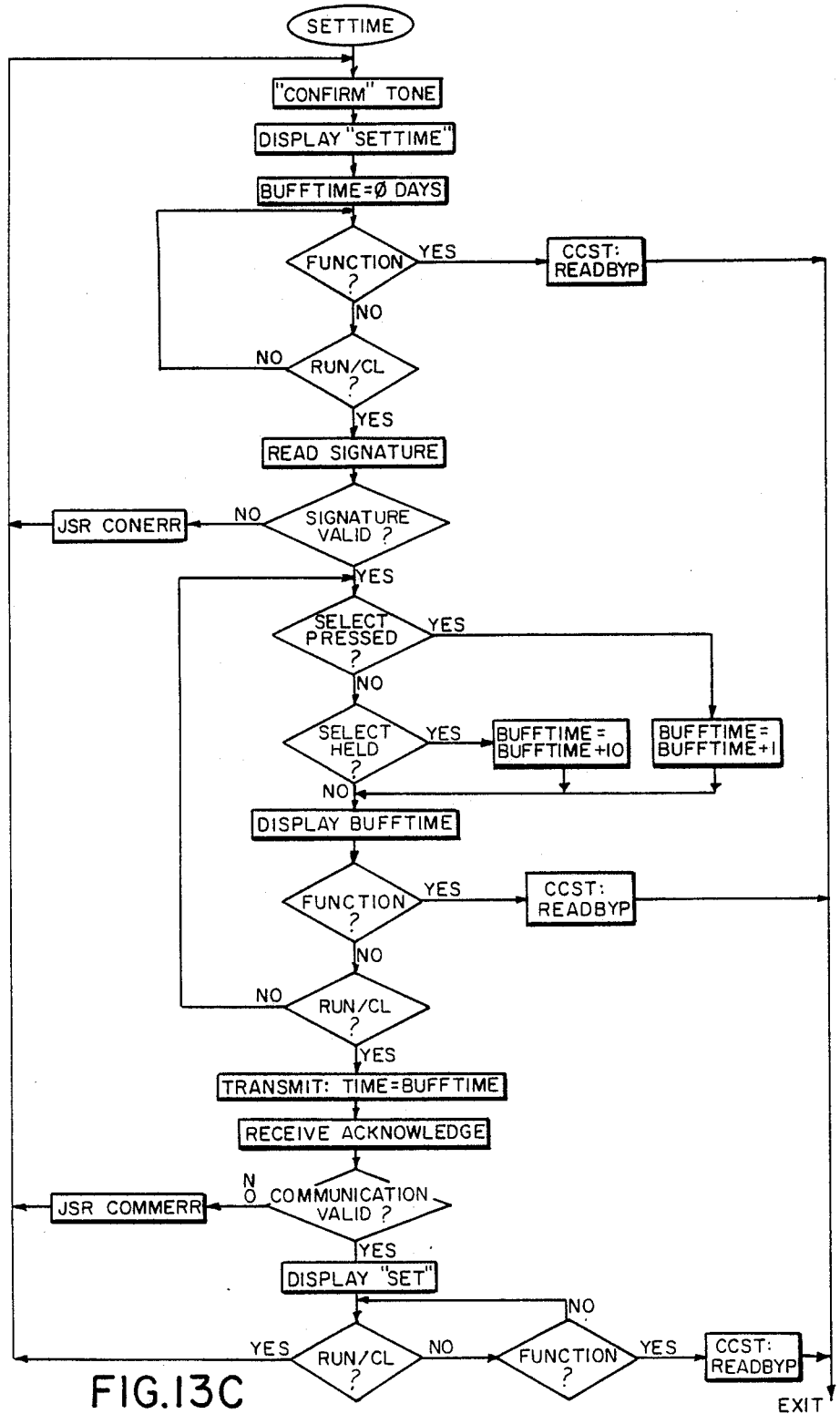

Referring now to FIG. 13C the SETTIME state is described in further detail. Audio output 290 is caused to sound the distinctive "confirm" tone and display 298 displays a mnenonic such as "SETTIME". Microprocessor 291 then loads a buffer, BUFFTIME with an initial value such as 0 days. In the event FUNCTION push button 299 is pressed, microprocessor 291 enters a state designated READBYP which enables service personnel to read from the memory of interlock 1 a table of data which indicates each day during which a given number of bypass events occurred. The READBYP state permits service personnel to read the total number, TOTBYP, of bypass events detected since the service reminder timer was last reset. READBYP also permits reading of all recorded DAY/NUMBER couplets which, as previously noted indicate each day (with reference to service reminder timer, TIME), during which at least one bypass event was detected as well as the number of separate bypass events detected on each given day. The READBYP state will be described in further detail shortly hereinafter with reference to FIG. 13D.

Continuing with the description of the SETTIME state illustrated in FIG. 13C, microprocessor 291 awaits pressing of FUNCTION push button 299 or RUN/CL push button 300. Provided that RUN/CL button 300 rather than FUNCTION button 299 is pressed, microprocessor 299 reads line SRS' 310 for the characteristic signature of interlock 1 and checks the validity of the signature in the manner previously described. If the signature does not appear or appears invalid, the CONNERR subroutine (FIG. 13F) is entered. The service person can then adjust the day value stored in the above mentioned buffer, BUFFTIME in increments of either 1 or 10 days by momentarily pressing or holding, respectively SELECT push button 301. As the BUFFTIME is incremented its updated value is continuously displayed by way of display 298. The service person increments the buffer until display 298 displays the number of days to which the service reminder timer TIME of interlock 1 is desired to be set. If the function push button 299 is pressed at this time, operation in the READBYP state will commence and the value of the service reminder timer will remain unchanged. That is, the TIME value previously read in the READTIME state rather than BUFFTIME will indicate the current value of the service reminder timer. To change the value of the service reminder timer, TIME to the BUFFTIME value appearing on display 298, RUN/CL push button 300 is pressed whereupon the contents of the BUFFTIME buffer are transmitted to the service reminder timer of microprocessor 160 by way of line IGN' 309 whereupon microprocessor 160 sets the service reminder timer equal to the number of days appearing on display 298. Microprocessor 160 acknowledges receipt of the updated TIME value by transmitting an acknowledgement which is received by microprocessor 291 by way of line SCL' 311. Microprocessor 291 then checks the validity of the acknowledgement communication. If the communication is not valid the COMMERR subroutine is entered. Otherwise, display 298 displays the word "SET" to indicate that the service reminder timer, TIME has actually been set to a new value. Pressing of the RUN/CL push button 300 will cause the above steps to be repeated whereas pressing of FUNCTION push button 299 will cause second remote service device 56 to enter the READBYP state.

Figure 13D:
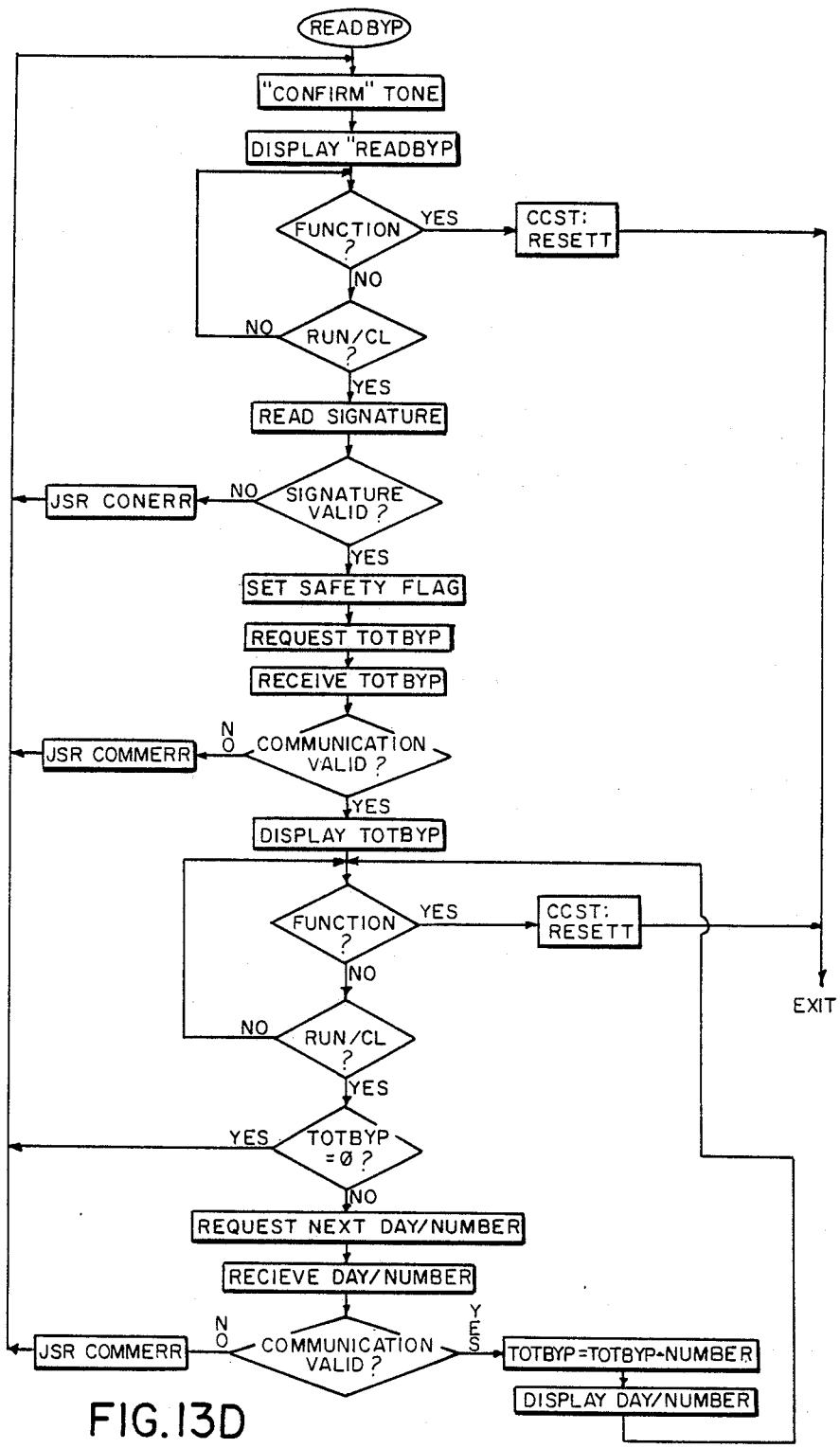
Figure 13E:
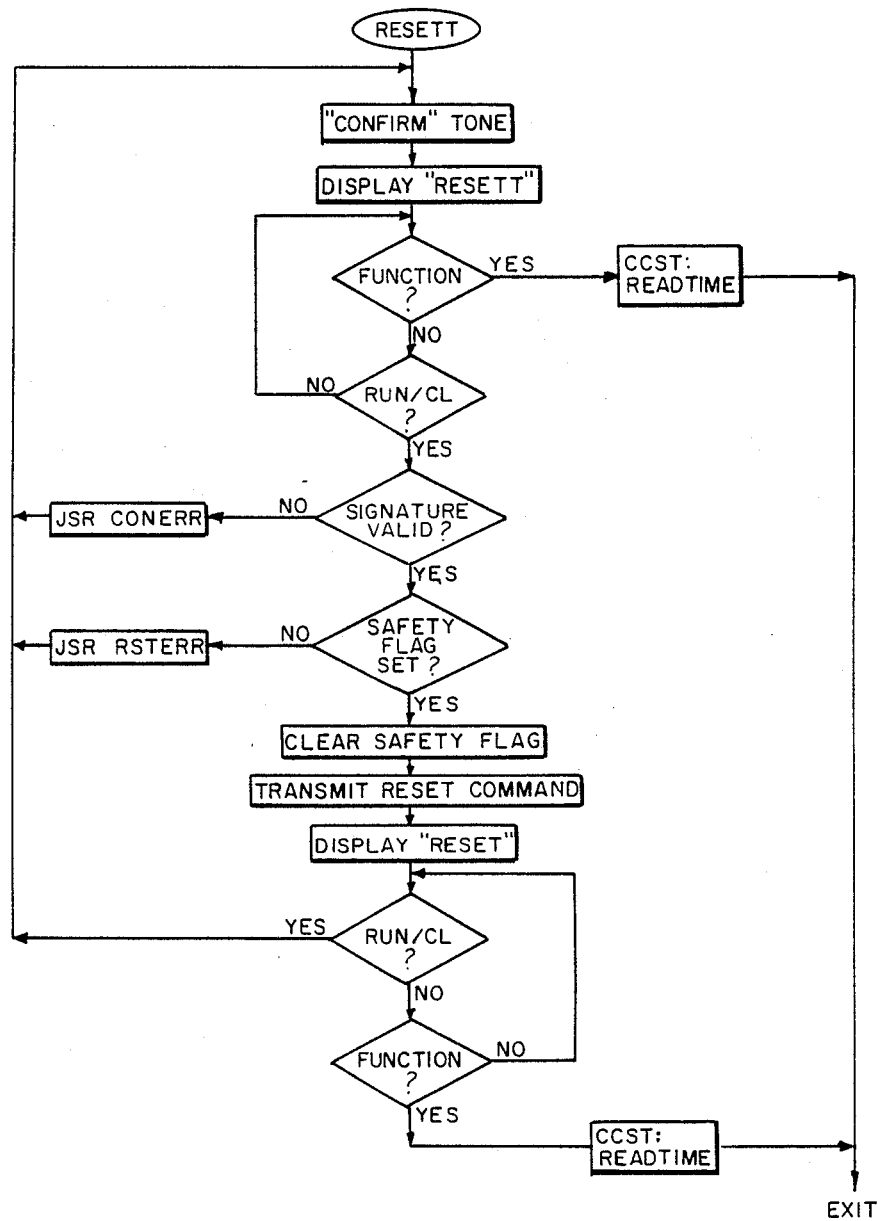

With reference now to FIG. 13D, entry of the READBYP state commences with sounding of the "confirm" tone by audio output 290 and display of a mnenonic such as "READBYP" on display 298 to indicate to the service personnel that second remote service device 56 is prepared to fetch the record of bypass events and to display that record by way of display 298. If FUNCTION push button 299 is pressed at this time, second remote service device 56 will enter a RESETT state to be described with reference to FIG. 13E. Alternatively, pressing of RUN/CL 300 causes microprocessor 291 to read line SCL' 311 checking for the presence of the aforementioned interlock signature signal thereon. If the signature does not appear or appears invalid, the error subroutine is entered. Assuming a valid signature is recognized, microprocessor 291 sets a "safety" flag in its memory. As will be more fully appreciated in connection with the description of the RESETT state (FIG. 13E) the available commercially in the United States as model TGS-813P from Figaro USA, Inc. of Wilmette, Ill. The structure, operation and mounting of sensor assembly 201 are discussed in further detail in commonly assigned U.S. patent application Ser. No. 07/152,470 incorporated by reference earlier. For present purposes it is sufficient to note that sensor 200 lies in gaseous communication with breath delivered into the inlet port 39 of sampling head 3 by way of mouthpiece 40.

Alcohol sensor 200 has one leg connected to ground 67 and a second leg connected to pin 37-6 by way of a line FBK 104 which includes a calibration potentiometer 205. The node between potentiometer 205 and sensor 200 corresponds to the output of sensor 200 and is carried to pin 37-5 over SEN line 103. Heater 202 has its leads connected to pins 37-7 and 37-8 by way of lines designated HTR1 105 and HTR2 106 as shown.

Sampling head 3 also includes means for sensing breath flow. Pressure switch 208 includes a set of normally open contacts one side of which is connected to ground 67 the other side of which is connected to microprocessor 160 by way of line PSW 102 and connected to pin 37-3 of receptacle 37 (see also FIG. 5). Although other devices including solid state pressure switches or various forms of flow sensors identifying bypass events which have been stored by microprocessor 160 in EEPROM 195.

As noted earlier, each couplet consists of a pair of integer values the first of which specifies the day when one or more bypass events occurred. This day is identified by an integer value representing the value of the service reminder timer, TIME as of the time the bypass event occurred. The TIME value can be easily correlated to a calendar day simply by referring to service records which indicate the date upon which the service reminder timer was last reset as well as the number of days to which it was reset. For example, if it is determined that the service reminder timer was set to a value of 37 on September 1 and a couplet of data indicates that two bypass events occurred on day TIME equals 33, the calendar date of those occurrences can readily be identified as September 5. The second integer value making up each couplet identifies the number of separately identified bypass events that occurred on the corresponding day. Thus, the total number of bypass events occurring over all recorded days should equal the value of TOTBYP previously displayed.

Each DAY/NUMBER couplet is received by microprocessor 291 together with a command the validity of which is checked in the manner previously described. Provided the command is valid, the value TOTBYP is decremented by the NUMBER portion of the couplet most recently received and that couplet is displayed on display 298 and manually entered into a permanent service log. When the service person is ready to read the next couplet, the RUN/CL push button 300 is pressed and the updated value of TOTBYP is again read. If TOTBYP is still greater than zero the next couplet of stored information is read and displayed in the manner just described. When all stored couplets have been read, TOTBYP will decrement to zero whereupon subsequent actuations of RUN/CL push button 300 will normally cause the program to loop back as indicated. Pushing FUNCTION button 299 causes microprocessor 291 to enter the RESETT state which will now be described with reference to FIG. 13E.

The RESETT state commences operation with the sounding of the "confirm" tone and the display of a mnenonic such as "RESETT" to indicate that second remote service device 56 is prepared to clear all recorded couplets of bypass events from the memory of interlock 1. This procedure is normally undertaken at the time interlock 1 is initially installed as well as each time periodic service checks are performed. Pressing of function button 299 will cause microprocessor 291 to commence operation in the READTIME state previously described with reference to FIG. 13A. Pressing of the RUN/CL button 300 causes microprocessor 291 to scan line SRS' 310 for the presence of the interlock signature signal generated by microprocessor 160. If that signature does not appear correctly, the CONNERR subroutine will be entered. Assuming on the other hand that the validity of the signature signal is confirmed, the status of the "safety" flag is checked. If the "safety" flag has not been set, this indicates that the stored couplets have not been read out previously and therefore should not be deleted. In that case, a subroutine RSTERR to be described with reference to FIG. 13F is entered. On the other hand if the "safety" flag was set, the "safety" flag is cleared and a reset command is transmitted to microprocessor 160. Upon receipt of the reset command, microprocessor 160 causes EEPROM 195 to be reset in a manner which will be more thoroughly explained in connection with the operational and software description of sobriety interlock 1. For the present, it is sufficient to note that this reset is effective to clear EEPROM 195 of all previously stored couplets. After the reset command has been generated by microprocessor 291, display 298 displays a mnenonic such as "RESET" indicating that the reset function has been completed. Subsequent pressing of RUN/CL button 300 is effective to repeat the above steps while pressing a function button 299 shifts operation to the READTIME state previously discussed.

With reference now to FIG. 13F the three error subroutines referred to above will now be described. Subroutine CONERR indicates that second remote service device 56 is not properly connected to an operational sobriety interlock 1. Upon entering this subroutine, display 298 displays "CONNECT" or a similar message to indicate the nature of the error to service personnel. Subsequently the "safety" flag is cleared. Attention is called to the error by the lighting of error LED 302 as well as by the sounding of a distinctive "error" tone over audio output 290. To turn LED 302 off, the service person presses RUN/CL push button 300 whereupon the program returns.

Subroutine COMMERR indicates that a communication error of some type has taken place between sobriety interlock 1 and second remote service device 56. The nature of the error is indicated to service personnel by displaying COMMERR or a similar message upon display 298. The remainder of the subroutine operates identically to the CONERR routine just described except that the "safety" flag is not cleared.

Subroutine RSTERR is entered from the RESETT state described above if the "safety" flag has not been set before the RUN/CL push button on 300 is pressed. As noted above, this indicates that the service person is attempting to clear recorded couplets without first having displayed those couplets. Accordingly, display 298 shows "WARNING" or a similar message. Otherwise, this subroutine operates the same as subroutine COMMERR described above.

Sobriety Interlock Software And Operational Description

Having described the configuration and basic electrical operation of the hardware of sobriety interlock 1 as well as the hardware and software of first and second remote service devices 55 and 56, the software and further details of the operation of sobriety interlock 1 will now be considered.

Figure 14:
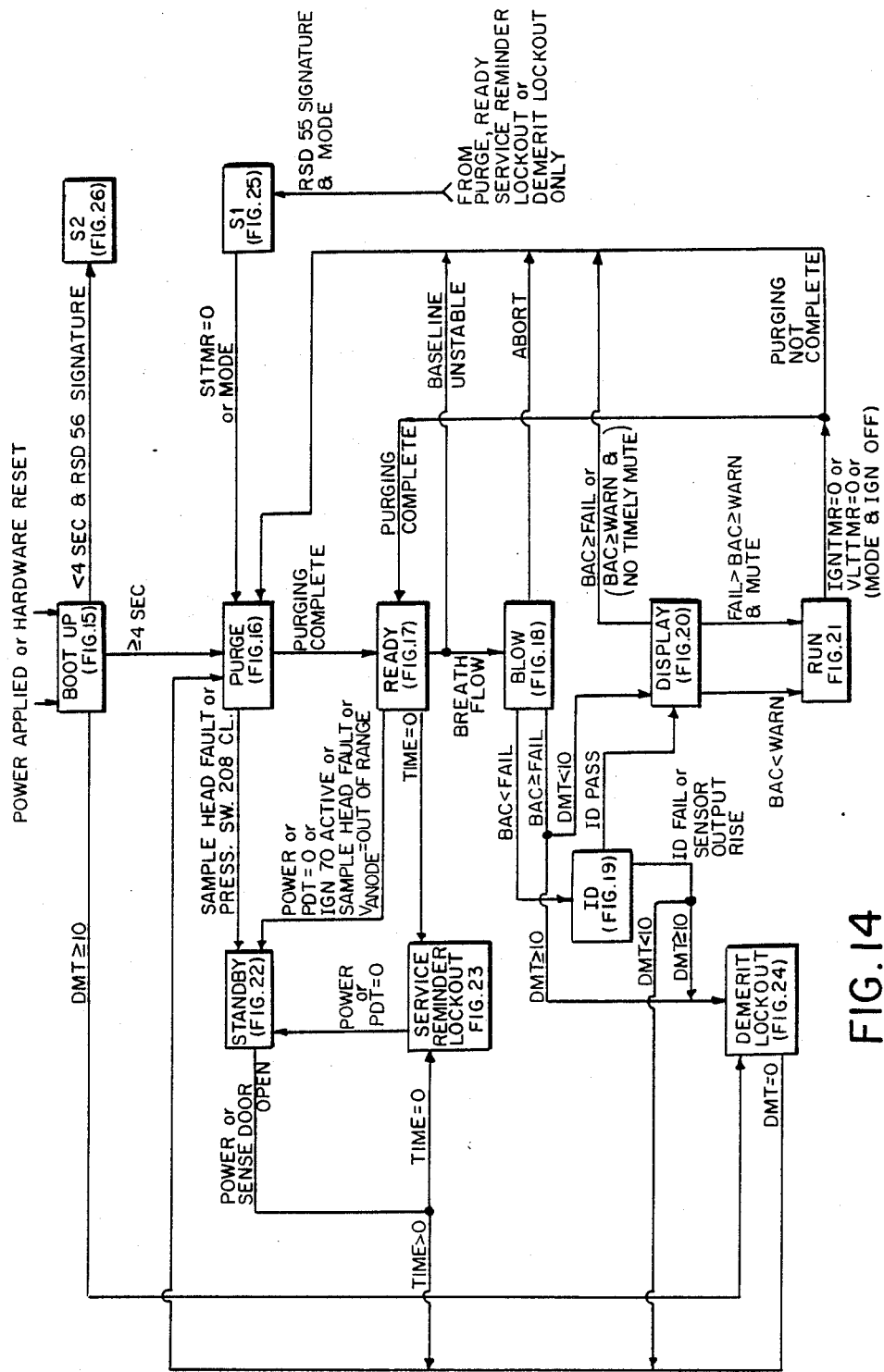
FIG. 14 is a software state diagram illustrating the operation of the microprocessor controller of FIG. 2.

FIG. 14 is a software state diagram wherein the overall operation of interlock 1 is illustrated in terms of a series of transitions between a number of software-defined states. A BOOT UP state is entered upon initial connection of electrical power to sobriety interlock 1 or at any subsequent time a hardware reset occurs. As noted previously, a hardware reset occurs whenever an appropriate logic signal is applied to microprocessor 160 by way of RST line 73 as may be affected for example by voltage regulator 145 in the manner previously explained with reference to FIG. 4. The BOOT UP state, whose details will be explained further with reference to FIG. 15, initializes microprocessor 160 for operation. Within the first 4 seconds of operation, if microprocessor 160 senses a second remote service device 56 connected to remote interface 47 a restricted access state, S2, is entered. Connection of a remote service device is sensed by microprocessor 160 though the appearance of a characteristic by encrypted RSD 56 signature signal which is periodically output by second remote service device 56 by way of line IGN' 309. The S2 state, which will be described in further detail with reference to FIG. 26, permits reading and setting of the service reminder timer as well as reading and clearing of all recorded bypass events by use of second remote service device 56 in the manner previously explained with reference to FIG. 13. For security purposes as well as safety, the S2 state can only be entered within the first 4 seconds of operation of interlock 1. Access to the S2 state is further restricted by requiring connection of service remote service device 56 which are possessed only by authorized service personnel. After 4 seconds have elapsed without interlock 1 sensing connection of a second remote service device 56, operation normally proceeds to the PURGE state which will be described further in connection with FIG. 16.

A major function of the PURGE state is to prepare alcohol sensor 200 for breath testing by "purging" it with heat applied by heater 202 in the manner previously explained with reference to FIGS. 8 and 9. Upon completion of the purging process, operation in the READY state commences.

Figure 18:
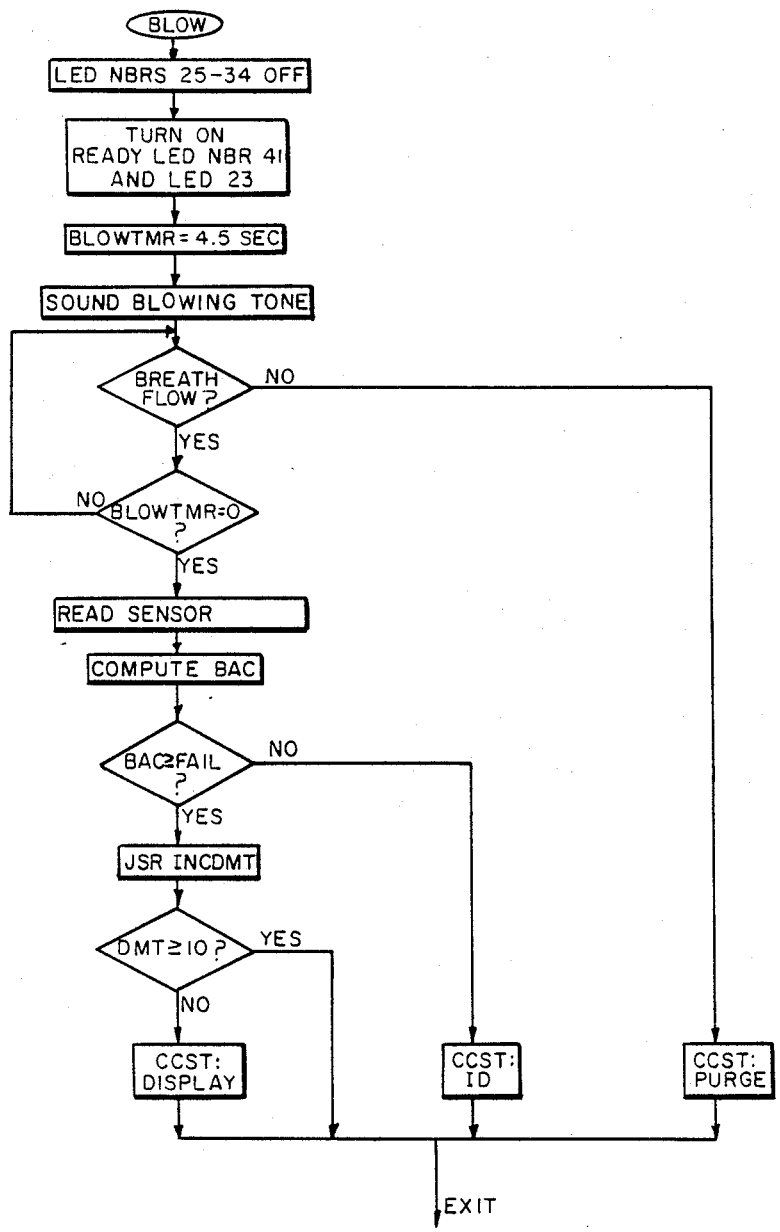
FIG. 18 is a diagram illustrating the BLOW state.

A principal function of the READY state is to sense commencement of delivery of a breath sample as indicated for example in the present embodiment by closure of pressure switch 208. Of course, breath flow could be sensed by alternative means such as means directly responsive to indicate delivery of a given flow rate or volume of breath. After closure of pressure switch 208 is sensed, to determine whether a stable baseline is present. That function is accomplished by means of a subroutine CHKSTABLE which will be explained later with reference to FIG. 33. If the baseline signal is not stable, the PURGE state is reentered. Otherwise, operation in a state referred to as BLOW, to be described further with reference to FIG. 18, commences. Among other functions, the BLOW state serves to ensure delivery of a deep lung breath sample by requiring that breath be delivered at a flow rate at least sufficient to keep pressure switch 208 open for a predetermined minimum time period such as 4.5 seconds. If that condition is not met, the breath test is aborted and operation in the PURGE state is resumed. Of course, a deep lung sample can be ensured in other ways such as measuring the volume by integrating one or more flow-related signals over time or summing a series of timed flow measurements. Provided that a deep lung breath sample has been obtained, the output of alcohol sensor 200 is read and blood alcohol concentration (BAC) is computed.

If the BAC level is greater than or equal to a predetermined FAIL limit, a demerit timer, DMT, is incremented by some value such as 5 minutes and its current value read. The demerit timer, DMT, defines the means by which the number of times a person can attempt to pass the alcohol measuring and identification phases of a test within a given period of time is limited. More specifically, timer DMT comprises a software timer that continuously counts down toward zero but which is incremented by a predetermined amount of time whenever a BAC measurement is found to be greater than or equal to the predetermined FAIL level as well as whenever an operator/test subject fails to identify himself or herself by correctly performing the identity-confirming act discussed earlier. If the setting of demerit timer DMT exceeds a predetermined threshold value after being incremented, interlock 1 commences operation in a DEMERIT LOCKOUT state as will be further explained with reference to FIG. 24.

In one preferred form, once the predetermined threshold of timer DMT is met or exceeded (by any amount) upon updating DMT, DMT is re-updated to define a maximum time limit, the entirety of which must expire before a new test can be passed. Alternatively, the DMT could simply be decremented from its current value such that after the threshold was exceeded upon updating, DMT would run down from its updated value. The predetermined threshold may be set to any desired time value such as 10 minutes for example. A principal function of the DEMERIT LOCKOUT state is to prevent interlock 1 from permitting any further tests until the demerit timer DMT times out. For example, where the threshold value is set at 10 minutes and 5 minutes are added each time DMT is incremented, once a person fails a test three times in rapid succession, demerit timer DMT would be updated to a total of 15 minutes so that taking further tests would be disabled for a corresponding amount of time. Of course, if desired, the amount of time added to the demerit timer as well as the time limit at which the DEMERIT LOCKOUT state will be entered and the maximum time limit (if one is used) can all be varied to achieve longer or shorter lockout periods as may be desired. Once the demerit timer counts down to zero, operation in the PURGE state is resumed in order to prepare interlock 1 for a new test. If the BAC FAIL level is met or exceeded but the demerit timer DMT is less than or equal to 10 minutes a DISPLAY state is entered. As its name indicates, the principal function of the DISPLAY state is to inform the operator of the result of the test. This is accomplished by the bar graph display 22 associated with operator interface 15 as well as with audible indications sounded by beeper 8.

After the alcohol measurement phase of the test, the operator/test subject may optionally be required to identify himself as a precondition to starting the vehicle. Preferably this is accomplished by requiring the operator to perform an identity-confirming act. An ID state embodying one form of an identity-confirming act is described in further detail later with reference to FIG. 19. The ID state is entered after the alcohol measurement phase of the test has been completed provided the measured BAC level falls below the FAIL limit.

An important aspect of the ID state contemplated by the invention is that the output of breath alcohol sensor 200 is monitored during the time when sensor 200 is exposed to breath delivered as part of the identity-confirming act. Should the output of sensor 200 significantly exceed its output at the time sensor 200 was read in the BLOW state, demerit timer DMT is incremented and tested in the manner just described. If the incremented value of the demerit timer does not meet or exceed a predetermined time limit, such as 10 minutes, the PURGE state is entered to prepare interlock 1 for a repeat test. If however demerit timer DMT meets or exceeds the predetermined time limit, the DEMERIT LOCKOUT state is entered. The purpose of comparing the output of alcohol sensor 200 during the identification phase with the prior reading from which the BAC level was calculated is to help ensure that the identity-confirming act is performed by the same individual that delivered the breath sample whose alcohol content was measured to determine BAC. It can be appreciated for example that if a sober person delivers a breath sample resulting in a BAC reading below the FAIL limit and, by some deceptive means, the identity-confirming act is attempted by an individual whose breath alcohol level is elevated relative to the prior reading, the subterfuge will be detected and starting the vehicle prevented unless a subsequent test is passed. Such a subsequent test can be permitted to proceed either directly or after a substantial delay imposed by way of the DEMERIT LOCKOUT state. If the identity-confirming act is not correctly performed, the demerit timer, DMT is incremented and the DEMERIT LOCKOUT state is entered if the incremented value of DMT meets or exceeds its predetermined threshold. Assuming that the identity-confirming act is correctly performed and the output of alcohol sensor 200 during the ID phase of the test does not rise significantly above the level from which BAC was determined, a transition from the ID state to the DISPLAY state takes place.

In the DISPLAY state, the BAC reading is compared with the FAIL limit as well as with a lower WARN limit. If the FAIL limit is not met or exceeded, a RUN state can then be entered. As will be explained further in connection with FIG. 21, the RUN state allows the vehicle to be started initially as well as restarted without a subsequent test under certain conditions in the event the vehicle stalls or is momentarily turned off. If the BAC reading is less than the FAIL limit but greater than or equal to the WARN limit, a cautionary WARN indication is provided wherein one or more yellow LEDs 27, 28, and/or 29 on bar graph display 22 is lighted and a distinctive "warn" tone sounded by beeper 8. However, when a WARN indication is given, the RUN state is entered only if the operator presses MUTE button 20 within a predetermined period of time, such as 60 seconds, to acknowledge his or her awareness that significant alcohol has been detected and that discretion should be used in deciding whether or not it is appropriate to drive. If the WARN condition is not acknowledged by timely actuation of MUTE button 20, the PURGE state rather than the RUN state is entered. As will be explained further, in the event an operator elects to drive after receiving and acknowledging a WARN indication, it is preferable that interlock 1 require a retest within a predetermined period of time; for example 20 minutes. This optional retest requirement will be discussed in further detail with reference to FIG. 21.

If the vehicle is turned off or stalls, interlock 1 allows the vehicle to be started without a new test within the lesser of two time periods defined by an ignition timer IGNTMR and a voltage timer VLTTMR. Whenever the vehicle ignition is turned off, as sensed by microprocessor 160 by way of ignition line IGN 70, timer IGNTMR begins counting down to define a predetermined period, such as one minute, during which the vehicle can be started without requiring a new test. Similarly, software timer VLTTMR begins counting down whenever $V_{ANODE}$ 61 falls below a predetermined voltage threshold value, RUNVLT, previously stored in memory 195 at the time sobriety interlock 1 was installed. Whenever either IGNTMR or VLTTMR times out, a new test must be passed to start the vehicle again. Prior to a new test alcohol sensor 200 must be purged. If alcohol sensor 200 has already been purged, operation in the READY state resumes. Otherwise, the PURGE state is entered.

With continuing reference to FIG. 14 the STANDBY state will now be introduced. The STANDBY state, which serves several functions, is entered from the PURGE state whenever pressure switch 208 is closed or a fault associated with sampling head 3 is detected. It will be recalled that the latter condition is sensed by microprocessor 160 by way of the heater control/sensing circuit 238 portion of heater circuit 49 as well as by checking alcohol sensor 200 for the absence of an output signal. The STANDBY state is also entered from the READY state in the event of a fault in sampling head 3 as well as in the event of a number of other conditions. These include: pressing POWER push button 19, the timing out of a power down timer, PDT indicating a prolonged period of nonuse as well as sensing power supply $V_{ANODE}$ 61 to be outside a predetermined voltage range. In addition, if interlock 1 is in the READY state and a person attempts to start the vehicle by closing ignition contacts 119, IGN line 70 will go active whereupon microprocessor 160 will cause the STANDBY state to be entered. In the STANDBY state, power consumption is reduced to conserve vehicle battery 108. This is accomplished by keeping power supply $V_{SW}$ 63 and thus, the circuitry it feeds, turned off most of the time. Periodically however, microprocessor 160 turns $V_{SW}$ 63 on just long enough to effect purging of alcohol sensor 200. It has been found that this avoids degradation in the performance of sensor 200 that might otherwise occur. Once the STANDBY state has been entered, subsequent pressing of POWER push button 19 or automatic sensing of the opening of the vehicle door will result reentry of the PURGE state provided the service reminder timer, TIME has not timed out.

Once the service reminder timer TIME counts down to zero, a SERVICE REMINDER LOCKOUT is preferably entered. Once this state is entered, the vehicle cannot be started until authorized service is obtained and the service reminder timer, TIME, is reset to a nonzero value. As can be seen by inspection of FIG. 14, so long as TIME equals zero, it is not possible to reach the RUN state. While pressing POWER push button 19 in the SERVICE REMINDER LOCKOUT state causes the STANDBY state to be reentered, operation reverts to the SERVICE REMINDER LOCKOUT state so long as TIME equals zero. Likewise, operation reverts to the SERVICE REMINDER LOCKOUT state from the READY state rather than proceeding to the BLOW state whenever the service reminder timer TIME has timed out. This helps to ensure that proper servicing of interlock 1 will be obtained as scheduled. If it is not the vehicle cannot be driven. As previously noted, service reminder timer, TIME, can be reset and operability of the vehicle restored using first remote service device 55.

Where use of interlock 1 is voluntary rather than compelled in some manner, the SERVICE REMINDER LOCKOUT state can be made operable to effectively bypass sobriety interlock 1 when the service reminder timer, TIME times out. Thus, instead of disabling the vehicle in the manner just described, interlock 1 is itself disabled so as to be incapable of restricting starting of the vehicle until such time as interlock 1 is serviced and the service reminder timer, TIME is reset. Persons are thereby compelled to have interlock 1 serviced if they wish to continue to have it restrict starting of the vehicle. During servicing, in addition to resetting the service reminder timer, TIME, interlock 1 can be checked for proper operation, and if necessary, calibrated or repaired. This helps to prevent the obvious safety risk of improperly enabling the vehicle to start as well as to avoid the nuisance of having the vehicle disabled when it should not be.

Connection of a first remote service device 55 to the receptacle 13 on the front panel 6 of interlock 1 together with actuation of MODE push button 21 causes interlock 1 to enter a restricted access state, S1, which will be described in further detail with reference to FIG. 25. As previously noted in connection with the description of first remote service device 55, entry of state S1 permits a number of functions to be performed. Among those is the setting of the service reminder timer, TIME. It should be noted that the S1 state can be entered only from the PURGE, READY, SERVICE REMINDER LOCKOUT or DEMERIT LOCKOUT states. As in the case of state S2, access to state S1 is restricted by limiting possession of first remote service device 55 to authorized service personnel. As a precaution, access to state S1 is also limited by a time constraint imposed by a timer S1TMR. The S1 state can be voluntarily exited and the PURGE state entered by pressing MODE button 21.

Having set forth the operational relationships between the various states, the operation of sobriety interlock 1 will now be described in further depth by considering further details of each of the above mentioned states individually.

Figure 15:
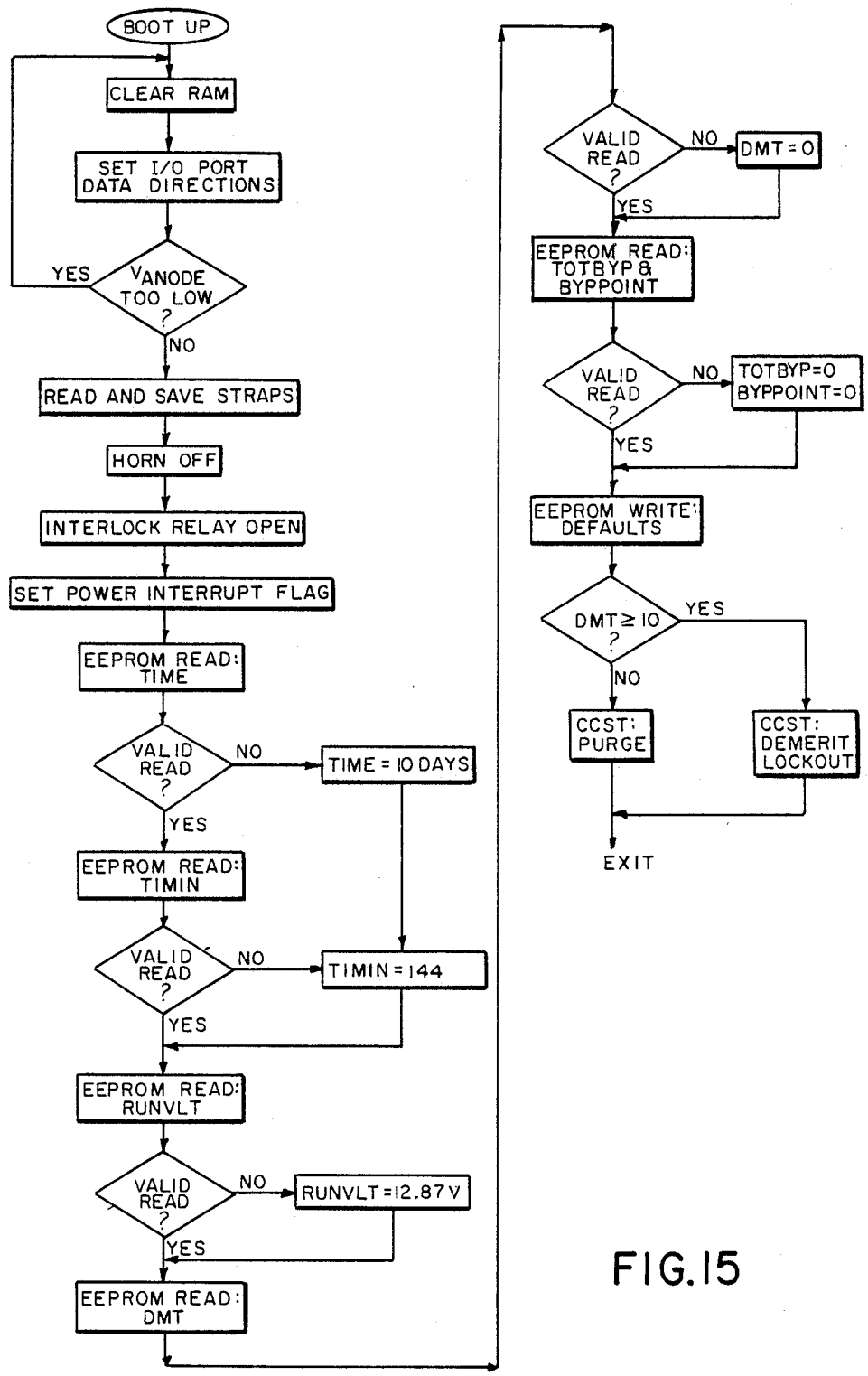
FIG. 15 is a diagram illustrating the BOOT UP state.

Referring now to FIG. 15, the BOOT UP state commences operation by clearing random access memory (RAM) within microprocessor 160 and by setting all I/O PORTS associated with microprocessor 160 as either inputs or outputs as required. In the event the sensed voltage at $V_{ANODE}$ 61 lies below a predetermined threshold, the above steps are repeated until $V_{ANODE}$ 61 reaches an acceptable voltage level. Microprocessor 160 then pulls line STS 176 low and scans lines BG0 80 through BG9 89 to check for the presence of jumpers across any of the pairs of jumper posts a–j associated with header 173. As previously noted in connection with FIG. 5, the presence of absence of a jumper strap across certain pairs of jumper posts a–j causes microprocessor 160 to select software appropriate to implement one or more optional features.

It will be assumed that header 173 is strapped as required to select the identity verification option previously described whereby an operator in addition to passing a breath alcohol test must also successfully pass an ID phase of the test in order to start the vehicle. As explained previously, the ID phase requires the operator to correctly perform an identity-confirming act, one version of which will be described in further detail in connection with the description of the ID state illustrated in FIG. 19. Header 173 is also strapped to select desired WARN and FAIL BAC thresholds and can be used to select such additional options as one may elect to provide.

Continuing with the description of the BOOT UP state illustrated in FIG. 15, once header 173 has been read, the vehicle horn is turned off in the manner previously described in connection with FIG. 3. Interlock relay 131 is then opened under the control of microprocessor 160 by way of ILK line 68 in the manner previously described in connection with FIG. 3. After setting a "power interrupt" flag, microprocessor 160 proceeds to read a number of parameters from EEPROM 195 and store them in RAM for subsequent use. It should be noted that where a control or indication action, such as opening or closing a relay or sounding or silencing a tone is called for at a particular step, that depending on previous operation, the affected component may already lie in the condition called for. In such event, no further action or change in condition is called for. For instance, if interlock relay is already open when an instruction to open the relay is executed, the relay simply remains open.

The first parameter read from EEPROM 195 is the value of the service reminder timer; TIME. Like all other parameters stored in EEPROM 195, TIME comprises an 8 bit data word. However, EEPROM 195 handles words up to 16 bits in length. The remaining 8 bits of each word are loaded with the compliment of the data bits. With both the data bits and their compliment being read by microprocessor 160, microprocessor 160 checks the validity of each read operation by comparing the data bits of the parameter with the other 8 bits. If those bits do not correspond to the compliment of the data bits, the read operation is judged invalid and its data is not loaded. Instead, a predefined default value for each parameter is stored in the appropriate RAM location. In the case of service reminder timer TIME, the default value is 10 days. The next parameter read from EEPROM 195 is the value of a 10 minute timer designated TIMIN. TIMIN is a timer used to increment service reminder timer TIME in order to improve its resolution. In the event TIMIN is not read validly, a default value of 144, which corresponds to 24 hours is loaded. Next, the voltage reference used as one criterion for determining whether the vehicle is actually running, RUNVLT is read from EEPROM 195 having been previously stored there upon initial installation or servicing of interlock 1 through the use of first remote service device 55 as will be more fully explained later. A default value such as 12.87 volts is loaded in the event RUNVLT is not validly read. Demerit timer DMT which was explained earlier with reference to FIG. 14 is then read from EEPROM 195. A default value of zero is used in the event of an invalid read operation. Finally, microprocessor 160 reads from EEPROM 195 two parameters relating to the record of bypass events. These are: TOTBYP, which represents the total number of bypass events recorded, and BYPPOINT. BYPPOINT is a pointer to the next available memory location in EEPROM 195 where a couplet of DAY/NUMBER information identifying one or more bypass events can be stored. TOTBYP and BYPPOINT are each loaded with default values of zero in the event either is not read validly.

In the event one or more of the above READ operations prove to be invalid, microprocessor 160 loads the proper default value into the appropriate location within EEPROM 195 in order to update it. Finally, demerit timer DMT is checked. If its value is greater than or equal to 10 minutes, microprocessor 160 changes the current state, (i.e. the BOOT UP state) to the DEMERIT LOCKOUT state. Otherwise, the PURGE state is entered.

Figure 16:
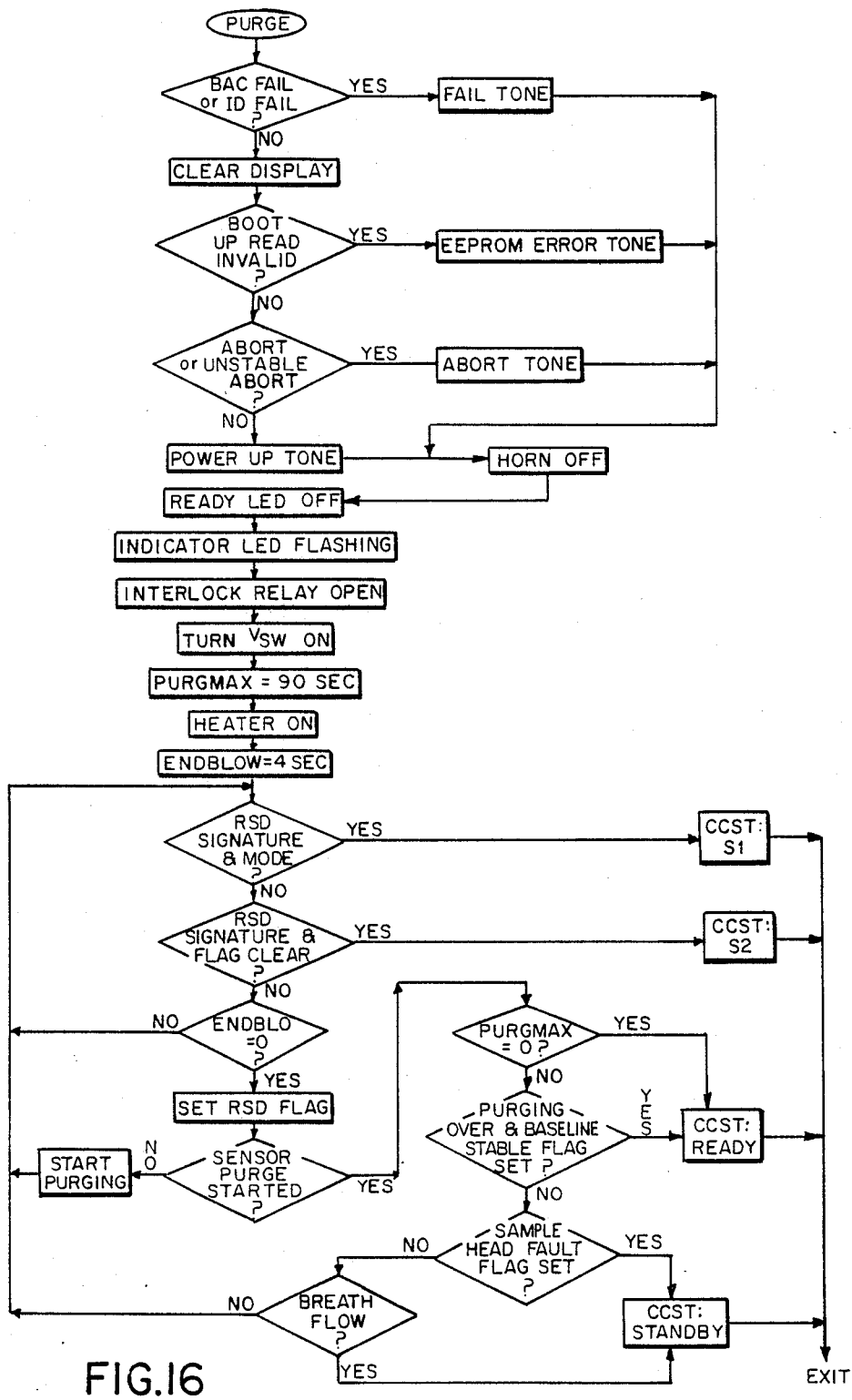
FIG. 16 is a diagram illustrating the PURGE state.

Referring now to FIG. 16, the PURGE state is illustrated. Beeper 8 sounds a distinctive "fail" tone if the PURGE state was entered as the result of failing either the BAC phase or ID phase of a previous test. In that event, bar graph display 22 displays the result of the BAC test. Otherwise, display 22 is cleared. If any invalid read operations occurred during the BOOT UP state, beeper 8 sounds a distinctive "eeprom error" tone to indicate that occurrence. In the event the PURGE state was entered as the result of an unstable baseline abort or as the result of a test abort, beeper 8 sounds a distinctive "abort" tone. A distinctive "powerup" tone is then sounded by beeper 8, the vehicle horn is turned off and the READY LED 41 associated with sampling head 3 is turned off while indicator LED 23 is set flashing to indicate that sensor 200 is being purged. If it is not already opened, interlock relay 131 is opened and power supply $V_{SW}$ 63 is turned on by way of PDC line 52 as previously explained with reference to FIG. 4. So that interlock 1 does not spend an inordinate amount of time attempting to purge alcohol sensor 200 in the event that its baseline signal does not stabilize, a limiting timer, PURGMAX is set to a value such as 90 seconds. Heater 202 is then energized to commence the purging operation previously described with reference to FIGS. 8 and 9.

Next, a timer "ENDBLOW" is set to a predetermined value such as 4 seconds. This timer serves two purposes. First, it defines the brief time window during which restricted access state S2 can be entered. ENDBLOW also provides a time period to allow the operator/test subject time to stop blowing breath. This permits pressure switch 208 to open before the purging operation is significantly underway. As inspection of FIG. 16 will show, the program scans for the presence of either the RSD 55 signature and the pressing of MODE button 21 or, the presence of signature RSD 56 and the presence of a clear "RSD 56" flag. If the former conditions are met, operation in the S1 state commences while if the latter conditions are met, the S2 state is entered. Once the ENDBLOW timer times out, the "RSD 56" flag is set, thus precluding entry of the S2 state. If purging of sensor 200 has not commenced, purging is started and the program loops as shown. Subsequently, if the PURGMAX timer times out, the READY state is entered regardless of the status of the baseline signal emanating from sensor 200. Otherwise, purging continues until the present purging cycle is over and a "baseline stable" flag is set. At that point, operation in the READY state commences. Setting of the "baseline stable" flag will be discussed further in connection with the CHKSTABLE subroutine of FIG. 33. If the baseline is not stable the status of the "sample head fault" flag is checked. If that flag is set, one of a number of possible faults associated with sampling head 3 is indicated and operation in the STANDBY state commences directly. Otherwise, the STANDBY state is entered from the PURGE state only if pressure switch 208 closes. As long as pressure switch 208 does not close, operation loops back to check for the connection of remote service device 55. In normal operation, completion of an effective purge of sensor 200 results in entry of the READY state which will now be described with reference to FIG. 17.

When the READY state is entered, the indicator LED 23 on the front panel 6 of control module 2 stops flashing and is lighted steadily to indicate to the operator that the purging operation is complete. Similarly, READY LED 41 begins flashing to indicate that interlock 1 is ready for a test. The program then jumps to subroutine DISPLAYFAULT which will now be described with reference to FIG. 28.

Subroutine DISPLAYFAULT commences by checking TOTBYP. If TOTBYP exceeds zero, indicating that at least one bypass event has occurred, LED 32 is lighted to so indicate. Persons other than authorized service personnel cannot clear TOTBYP or permanently extinguish LED 32 once it has been lighted. Accordingly service personnel will be aware immediately upon a cursory visual inspection of interlock 1 that at least one bypass event has occurred. Disconnecting interlock 1 from its power source will not be effective to erase TOTBYP since its value is stored in non-volatile memory 48. Thus, if interlock 1 is disconnected from vehicle battery 108, even if for an extended length of time, TOTBYP will be retained and LED 32 will light when power is reapplied to interlock 1. In fact, the unauthorized disconnection of power from interlock 1 is itself an event which will be detected, recorded and displayed for the benefit of service personnel. This is accomplished in part by means of a "power interrupt" flag, the setting and clearing of which will be described in further detail later.

Figure 28:
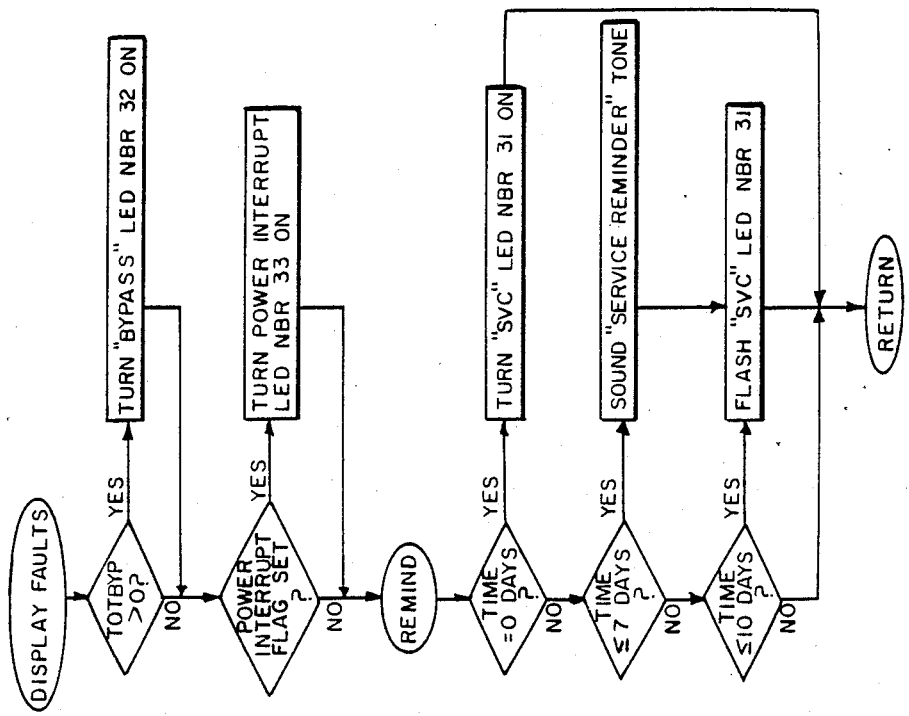
FIG. 28 is a diagram illustrating the DISPLAYFAULT subroutine and the REMIND subroutine.

For the present purposes, it is sufficient to note that the status of the "power interrupt" flag is checked in the DISPLAYFAULT subroutine as FIG. 28 indicates. If the "power interrupt" flag is set the power interrupt LED 33 is lighted. Except for brief periods during which display 22 is serving other functions, LED 33 remains lighted until the "power interrupt" flag is cleared. As will later be appreciated more fully, the latter function can be performed only by authorized service personnel. Thus, lighting of LED 32 indicates that since the time interlock 1 was installed or last serviced, power had been interrupted and reapplied. Since the vehicle could have been started one or more times within that period without interlock 1 being used to provide proper clearance, it is important to have means for advising service personnel that a power interruption had occurred.

It should also be appreciated that the service reminder timer, TIME is retained by nonvolatile memory 45 but does not continue to be decremented in the event the power to sobriety interlock 1 is interrupted. Accordingly, the total duration of any power interruption can be determined to within one day simply by reading the value of the service reminder timer, TIME and consulting the permanent service records for that particular interlock unit. Such records should be kept to indicate when the interlock unit was installed or last serviced and the number of days to which the service reminder timer, TIME was then set. Any discrepancy between the number of days that have actually elapsed since that time and the number of days the service reminder timer, TIME would indicate have elapsed upon comparing the current TIME value with service records, indicates the total duration of any power interruptions occurring during the period.

Subroutine DISPLAYFAULT incorporates a subroutine designated REMIND which serves to check the status of the service reminder timer, TIME and to provide appropriate indications. If service reminder timer TIME equals zero days, a service reminder LED such as LED 31 is lighted continuously. This indicates that service was not obtained on or before the scheduled due date. As shown in FIG. 1, LED 31 is labelled with appropriate indicia such as the legend "SVC". If the service reminder timer TIME does not equal zero, it is next checked to determine whether its value is less than or equal to a value defining an optional grace period which preferably is provided. If a grace period is used, its duration may be any desired length of time. Seven days for example has been found quite suitable. During the grace period, beeper 8 sounds a distinctive "service reminder" tone once a minute to remind the operator that service of interlock 1 is past due. If the operator fails to obtain service either on the due date or within the grace period, the service reminder timer, TIME will time out and SVC LED 31 will be lighted as described above. While not necessary, it is preferable to provide one or more advance reminder indications prior to the time when service is actually scheduled. In one preferred embodiment this is accomplished by flashing SVC LED 31 during some period, such as 3 days, prior to the actual scheduled service date. To accomplish this, when service reminder timer TIME reaches a value of less than or equal to ten days, SVC LED 31 flashes intermittently. When the operator sees the flashing of SVC LED 31, he or she knows that interlock 1 is scheduled for service within three days. Like all subroutines, subroutines DISPLAYFAULT and REMIND return to a point in the program just after that from which the subroutine was called. Like TOTBYP, TIME is stored in non-volatile memory 45. Therefore, once service reminder timer, TIME expires, its value cannot be reset by interrupting the power supplied to interlock 1. Therefore, once LED 31 is lighted or begins flashing, the same operation will resume after a power interruption when power is eventually restored.

Figure 17:
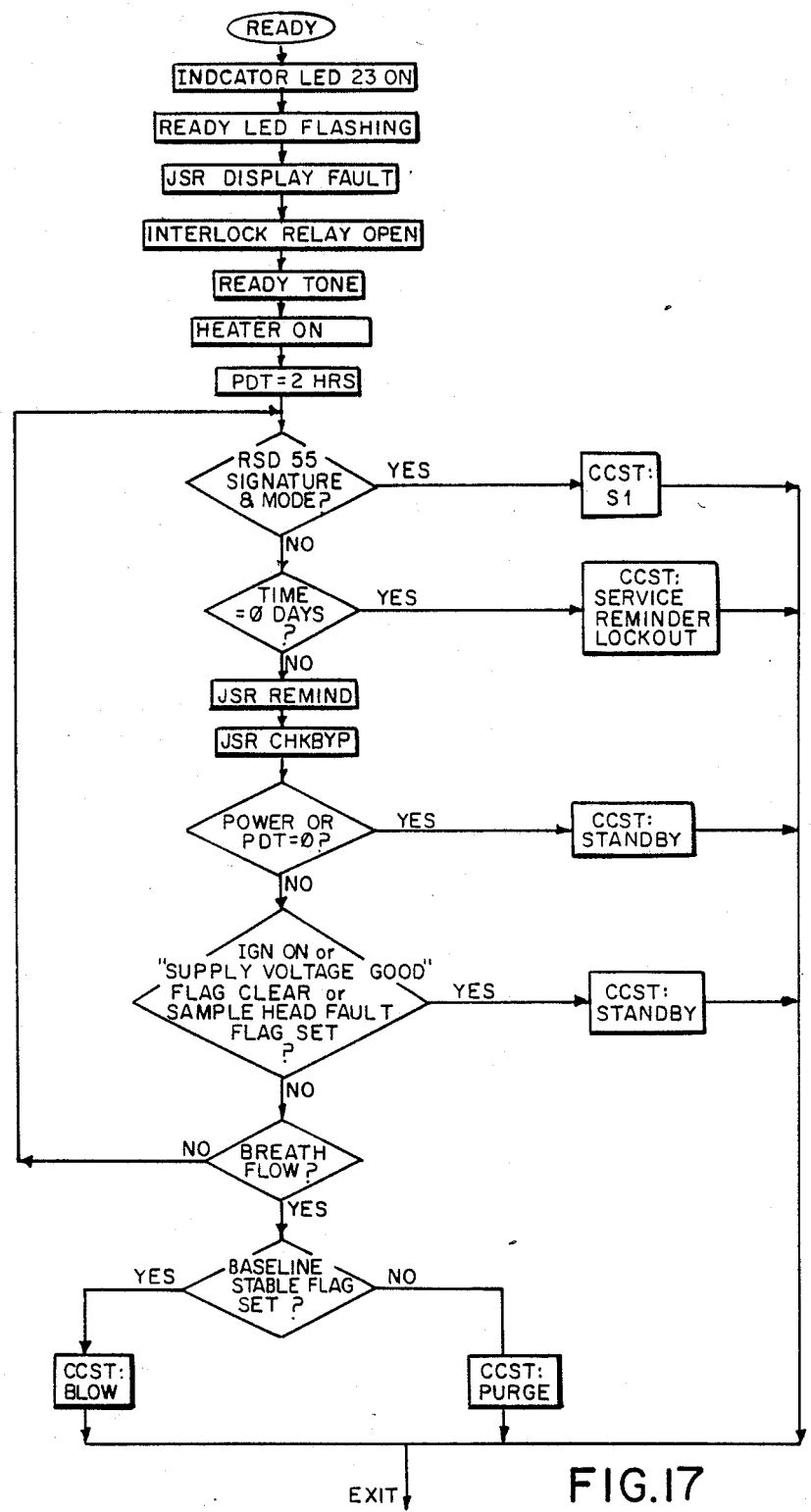
FIG. 17 is a diagram illustrating the READY state.

Continuing now with the description of the READY state with reference particularly to FIG. 17, after subroutine DISPLAYFAULT is executed, interlock relay 131 is opened by way of ILK line 68. A distinctive "READY" tone is sounded by beeper 8 to audibly indicate that interlock 1 is prepared for a test. Prior to testing, the power delivered to sensor heater 202 is throttled down to a steady state value and a power down timer, PDT is set to some desired interval such as two hours. The purpose of the timer PDT will become apparent shortly.

Figure 29:
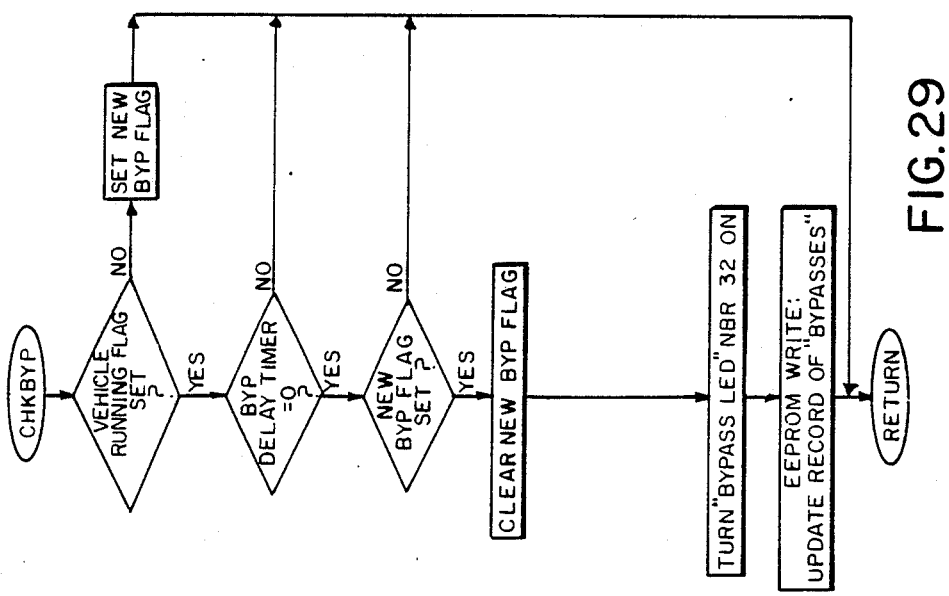
FIG. 29 is a diagram illustrating the CHKBYP subroutine

Microprocessor 160 checks to determine whether a first remote service device 55 is connected to receptacle 13 by checking for the presence of RSD 55 signature in the manner previously described. If the signature signal is present and MODE button 21 is pressed, operation transfers from the READY state to the S1 state described earlier. Otherwise the service reminder timer TIME is again checked and the service reminder LOCKOUT state is entered if TIME equals zero days. Subroutine REMIND is then called and executed in the manner described above to provide appropriate audible and/or visual indications. Upon returning from execution of the REMIND subroutine, a subroutine CHKBYP is called. CHKBYP updates the record of attempts to start the vehicle when sobriety interlock 1 is bypassed Subroutine CHKBYP which will now be described with reference to FIG. 29 is called in each operational state wherein the vehicle to which interlock 1 is connected should not be running. Subroutine CHKBYP first determines whether the vehicle is running by checking the status of a "vehicle running" flag which will be described further in connection with the CHKSUPPLY routine of FIG. 31. If the "vehicle running" lag is not set, indicating that the vehicle is not running, a "new bypass" flag is set. Setting of the "new bypass" flag indicates that the next bypass event that is detected constitutes a separate and distinct new bypass event rather than merely being a continuation of a previous one. This is true because the "new bypass" flag is only set after the vehicle has stopped running at least some point after the last recorded bypass event. This technique prevents a single bypass event from being recorded more than once. If the vehicle is not running and the "new bypass" flag is set the subroutine returns Otherwise, if the vehicle is running and BYP delay timer is checked. The BYP delay timer prevents a bypass event from being recorded for a predetermined period of time such as 5 minutes. The purpose of the BYP delay timer will now be explained.

A bypass event is normally recorded in the event the vehicle to which sobriety interlock 1 is connected appears to be running unless both the breath alcohol measurement and ID phases of a test have been passed within a predetermined time prior to the starting of the vehicle. It may sometimes occur however, that after driving, $V_{ANODE}$ 61 remains above the run voltage threshold RUNVLT, for some length of time after the ignition is turned off. If the driver happens to turn the vehicle ignition switch on again without performing a test before $V_{ANODE}$ 61 drops below the run voltage threshold RUNVLT, the vehicle will erroneously appear to be running without a timely test having been passed. Bypass timer BYP avoids erroneously recording a bypass event under these conditions by delaying recording of a bypass event for a period of time sufficient for $V_{ANODE}$ 61 to drop below run voltage threshold RUNVLT, after the vehicle ignition is turned off. A period of about 5 minutes has been found to be sufficient. After the BYP timer times out, bypass events are recorded in the normal manner whenever a test has not been passed and $V_{ANODE}$ 61 is found to exceed RUNVLT and the vehicle ignition is on unless the "new bypass" flag is not set.

If the "new bypass" flag was set, it is then cleared and "BYPASS" LED 32 is turned on. The record of bypass events stored in memory is then updated by recording the current value of the service reminder timer TIME in the appropriate DAY register and incrementing both NUMBER and TOTBYP. If the value of the service reminder timer TIME is different from the last recorded DAY entry, a new DAY/NUMBER couplet is recorded so that all bypass events occurring during the new DAY will be recorded in the corresponding NUMBER register In the event that all available memory space for couplets has been filled, the DAY value of the last recorded couplet is set to zero and further bypass events are noted by incrementing the NUMBER value of that couplet.

Continuing with the description of the READY state, just following execution of the CHKBYP subroutine, the STANDBY state can be entered either voluntarily or automatically. Voluntary entry of the STANDBY state can be effected by pressing POWER push button 19 while the STANDBY state is automatically entered if the power down timer PDT times out thereby indicating that interlock 1 has not been used for a prolonged period of time. In either case, entry of the STANDBY state is effective to conserve vehicle battery 108 by turning power supply $V_{SW}$ off. A number of other occurrences are also effective to cause entry of the STANDBY state from the READY state. In particular, if IGN line 70 is active indicating an attempt to start the car prior to a test, the STANDBY state is entered. Also, if the "sampling head fault" flag is set or a "supply voltage good" is clear STANDBY operation will commence. As will be made more clear in connection with the CHKSUPPLY subroutine of FIG. 31, setting of the "supply voltage good" flag indicates that $V_{ANODE}$ 61 lies inside an acceptable operating range.

Provided the STANDBY state is not entered, microprocessor 160 determines whether a breath sample is being delivered. This is indicated in the present embodiment by closure of pressure switch 208 as sensed by way of PSW line 102. If breath flow is not sensed, the program loops as indicated. Once breath flow commences however, the status of the "baseline stable" flag is checked. If the baseline signal from alcohol sensor 200 is not stable, an accurate BAC reading cannot be ensured. Accordingly, the PURGE state is reentered so that sensor 200 can be repurged to attempt to stabilize its baseline. If the baseline is stable when breath flow commences, operation proceeds to the BLOW state which will now be described with reference to FIG. 18.

In the BLOW state the flow of breath which began at the end of the READY state continues. LEDs 25 through 34 of bar graph display 22 are extinguished and indicator LED 23 is turned on. READY LED 41 stops flashing and is lighted steadily indicating that sufficient breath flow is being delivered by the operator/test subject into sampling head 3 by way of mouthpiece 40. To ensure the alcohol measurement is made with reference to a deep lung breath sample, a timer BLOWTMR is set to a predetermined interval such as 4.5 seconds during which pressure switch 208 must remain closed. The interval defined by BLOWTMR is selected in accordance with the minimum flow of breath at which pressure switch 208 remains closed to define a volume of breath sufficient to ensure procurement of a deep lung sample. To audibly indicate a breath sample is being delivered, beeper 8 sounds a distinctive "blowing" tone. If breath flow does not continue at a rate sufficient to maintain pressure switch 208 closed during the entire period defined by BLOWTMR, the PURGE state will be reentered. Once the blow timer times out, alcohol sensor 200 is read. Based on the sensor reading, a blood alcohol concentration "BAC" value is computed and saved.

To begin the process of deciding whether the BAC measurement is sufficiently low to pass the BAC measurement phase of the test, the BAC value is compared with a predetermined FAIL limit. Provided the FAIL limit is not met or exceeded, the BAC measurement phase of the test is PASSED and a state referred to as ID is entered. As will be described in detail shortly with reference to FIG. 19, the ID state defines an optional identification phase of the test during which an operator must identify himself or herself as a designated individual as a precondition to allowing the vehicle to start. The ID phase will be described in further detail with reference to the ID state of FIG. 19.

Assuming the computed BAC value meets or exceeds the predetermined FAIL limit, the BAC measurement phase of the test is considered failed and a demerit timer incrementing subroutine, INCDMT is entered. Upon returning from INCDEMERIT, the updated value of the demerit timer DMT is compared with a predetermined limit such as 10 minutes. If DMT is not greater than or equal to that limit the DISPLAY state is entered. Otherwise, operation continues in the DEMERIT LOCKOUT state which was entered by way of the INCDMT subroutine which will now be described with reference to FIG. 30.

Figure 30:
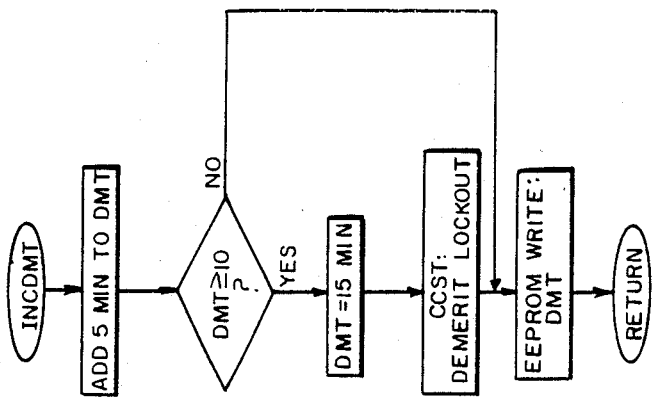
FIG. 30 is a diagram illustrating the INCDMT subroutine.

As illustrated in FIG. 30, the INCDMT subroutine commences by adding 5 minutes to demerit timer DMT. The updated value of DMT is then compared with a predetermined first limit such as 10 minutes. Provided the first limit is not met or exceeded, the record of DMT in non-volatile memory is kept current by writing the updated value of DMT to EEPROM 195 whereupon the subroutine returns. If the updated value of DMT is greater than or equal to the 10 minute limit, the value of DMT is preferably set to equal some arbitrary maximum length of time such as 15 minutes. Thus, once the DEMERIT LOCKOUT state is entered, it persists for the full maximum length of time.

Figure 24:
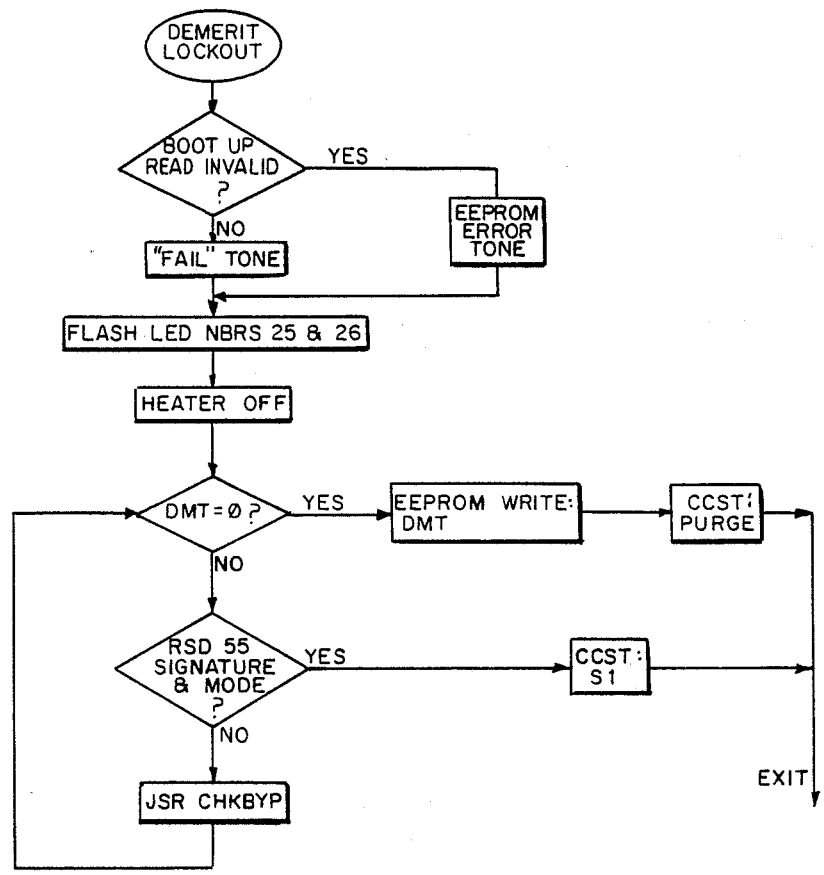
FIG. 24 is a diagram illustrating the DEMERIT LOCKOUT state.

Referring now to FIG. 24, the DEMERIT LOCKOUT state will now be described in further detail Entry of the DEMERIT LOCKOUT state is triggered when an operator/test subject has failed either the BAC measurement phase and/or the ID phase of the test too often within the time limits defined by the demerit timer DMT. Upon entry of the DEMERIT LOCKOUT state, the distinctive "eeprom error" tone is sounded in the event that an invalid read occurred during BOOT UP. If no such errors occurred, a distinctive "fail" tone is sounded by beeper 8 and LEDs 25 and 26 flash alternately to indicate that the DEMERIT LOCKOUT state has been entered. Heater 202 is turned off and the status of the demerit timer DMT is continuously read. So long as the demerit timer DMT has not timed out, the DEMERIT LOCKOUT state can be exited only by way of the S1 state. As previously described, the S1 state can be entered only by pressing MODE push button 21 while a first remote service device 55 is connected to control module 2. So long as the S1 state is not entered, the CHKBYP subroutine is repeatedly executed until the demerit timer DMT times out. At that time, the updated value of the demerit timer DMT (i.e. zero) is stored in EEPROM 195 and the PURGE state is automatically entered. Note that the DEMERIT LOCKOUT state differs significantly from the SERVICE REMINDER LOCKOUT state in that the latter state continues for an indefinite period until service is obtained. Conversely, the DEMERIT LOCKOUT state persists for a maximum amount of time defined by demerit timer DMT. As is also the case with the SERVICE REMINDER LOCKOUT state, the RUN state cannot be entered and therefore, the vehicle cannot be started, so long as sobriety interlock 1 is in the DEMERIT LOCKOUT state.

Figure 19A:
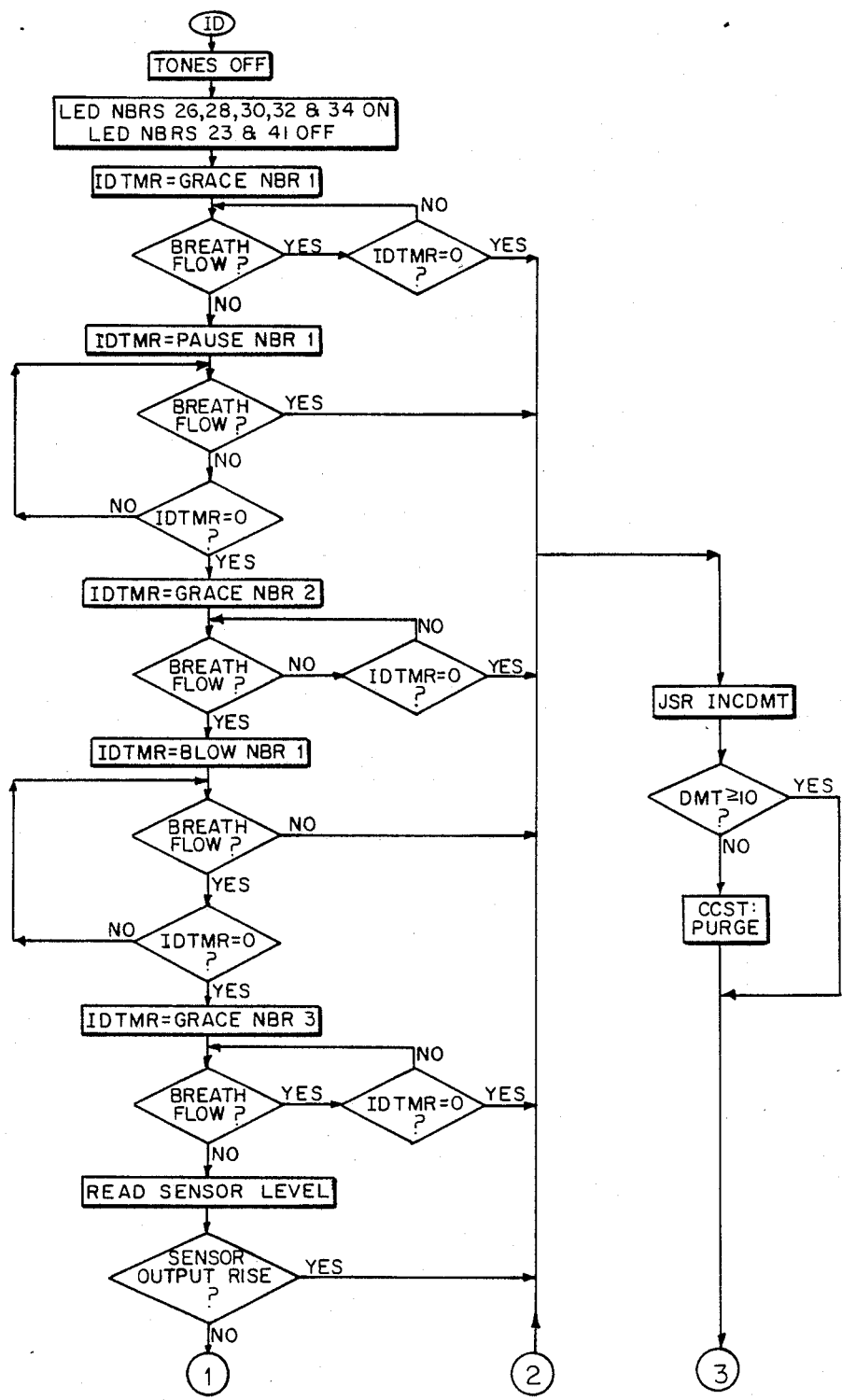
FIG. 19A and FIG. 19B are diagrams which together illustrate the ID state.
Figure 19B:
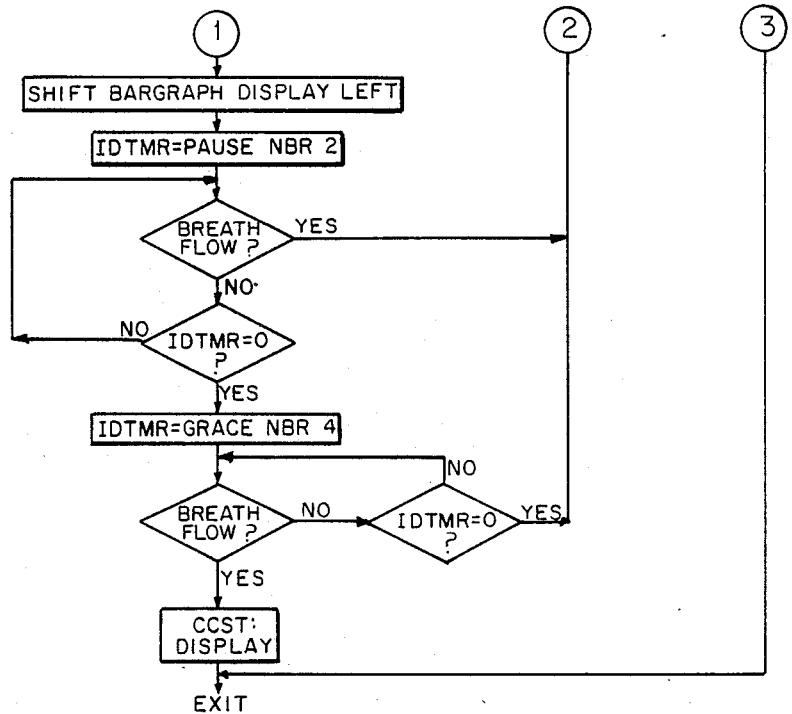

Assuming the BAC measurement phase of the test is passed in the BLOW state, the ID state which will now be described with reference to FIG. 19 is entered. At the beginning of the ID phase of the test, beeper 8 is silenced Indicator LED 23 and READY LED 41 are turned off and display 22 is set such that every other one of its LEDs is lighted. These visual displays cue the operator/test subject to commence performing an identity-confirming act, mastery of which identifies the operator/test subject as a designated individual. As noted previously, correct performance of the identity-confirming act requires a degree of skill sufficiently high that most persons cannot perform the act correctly without having attempted performance of the act at least some minimum number of times which is greater than the number of times demerit timer DMT allows the act to be attempted prior to entering the DEMERIT LOCKOUT state The identity-confirming act is preferably performed by blowing a series of spaced puffs of breath into mouthpiece 40. Each puff of breath is sensed by pressure switch 208 and must meet predetermined time and minimum flow rate constraints. Each puff of breath is separated from preceding and succeeding breaths by a pause which also must meet predetermined time and minimum flow rate requirements. To allow some degree of inaccuracy in the timing of the respective breaths and pauses, each such period is preferably preceded with a brief grace period which defines a timing tolerance. An exemplary identity-confirming act is set forth in FIG. 19 and will now be described in further detail.

After display 22 is lighted in the manner indicated above, a timer, IDTMR is loaded with a time corresponding to the duration of a first grace period. The flow of breath from the BAC measurement phase of the test completed in the BLOW state must cease or at least fall below a level sufficient to close pressure switch 208 prior to expiration of grace period number one. If it does not, the ID phase is failed and subroutine INCDMT is entered. Assuming the flow of breath falls off acceptably before the first grace period expires, IDTMR is loaded to a value defining the required length of the first pause. If a puff of breath at a flow rate sufficient to close pressure switch 208 commences before IDTMR times out at the conclusion of the first pause, subroutine INCDMT is called. Otherwise, IDTMR is loaded with a value specifying the length of a second brief grace period during which a first puff of breath or "flow" sufficient to close pressure switch 208 must commence. If the blow does not begin before the second grace period ends, the ID phase is failed and the INCDMT subroutine is called. Provided the first blow does begin soon enough, IDTMR is loaded with a value specifying the required duration of the first puff of breath or "blow". If breath flow falls off enough to permit pressure switch 208 to open before IDTMR times out at the end of the first blow, the ID phase is failed and subroutine INCDMT is entered. Assuming the first blow does not end prematurely, timer IDTMR is loaded with a value specifying a third grace period during which the first blow of breath must cease. If it does not, the ID portion of the test is failed and subroutine INCDMT is called.

At this point, or at any other convenient time during the ID phase, the invention contemplates reading the output of alcohol sensor 200. After the output signal from alcohol sensor 200 is read, the current sensor reading is compared with the reading from which BAC was calculated. If the two sensor output readings differ significantly, one can be reasonably certain that the breath being delivered in the ID phase emanates from a different source than the breath upon which the BAC measurement was based. This would indicate that an accomplice or bogus gas source was likely used to deliver the breath sample upon which the BAC measurement was based. Accordingly, if a significant rise in the sensor output is sensed during the ID phase, the test is failed which, in the current example results in entry of the INCDMT subroutine. Of course, other appropriate indications or responsive measures could be undertaken. For example, a distinctive audible and/or visual indication could be provided by way of beeper 8 and/or display 22 respectively. Also, in lieu of the actions initiated by the INCDMT subroutine, sobriety interlock 1 and/or the vehicle in which it is installed could be disabled immediately for some selected period of time or indefinitely until service was obtained and the fault cleared by means of a remote service device such as first remote service device 55. The limit of difference between the two readings of sensor 200 which one selects to trigger one or more of the foregoing results should be selected in accordance with system requirements such as accuracy limitations, drift, and other factors which can cause the output of sensor 200 in the ID phase to vary from its output in the BAC measurement phase. In Applicants preferred embodiment, sensor output variation rise is limited to about 115 millivolts. Provided the rise in the output of sensor 200 remains below such an acceptable limit, the test is not caused to be failed and the ID phase proceeds.

After checking the rise in the output of alcohol sensor 200, which may occur for example just after the third grace period ends, bar graph display 22 is shifted left (i.e. LEDs 25, 27, 29, 31 and 33 only are lighted). This indication serves as feedback to the operator/test subject that the initial portion of the identity-confirming act has been performed correctly. Next, timer IDTMR is loaded with a value specifying a second pause. If breath flow is sensed before the completion of the second pause as indicated by the timing out of IDTMR, the ID phase of the test is failed and subroutine INCDMT is entered. Provided pause number two ends before further breath flow is sensed, IDTMR is loaded with a value specifying a fourth grace period. A second and final puff of breath must at least commence before grace period number four expires. Provided it does, the ID phase of the test is passed and operation proceeds to the DISPLAY state. If, on the other hand no breath flow is sensed before the end of grace period number four, the test is failed and subroutine INCDMT is called. As in all previous cases wherein this subroutine is called from the ID state, the status of demerit timer DMT is checked upon returning. If demerit timer DMT meets or exceeds its 10 minute threshold, operation proceeds in the DEMERIT LOCKOUT state which is entered by way of subroutine INCDMT. If, on the other hand, DMT is less than ten, operation in the PURGE state commences and a retest can be performed without waiting for demerit timer DMT to time out.

Figure 20:
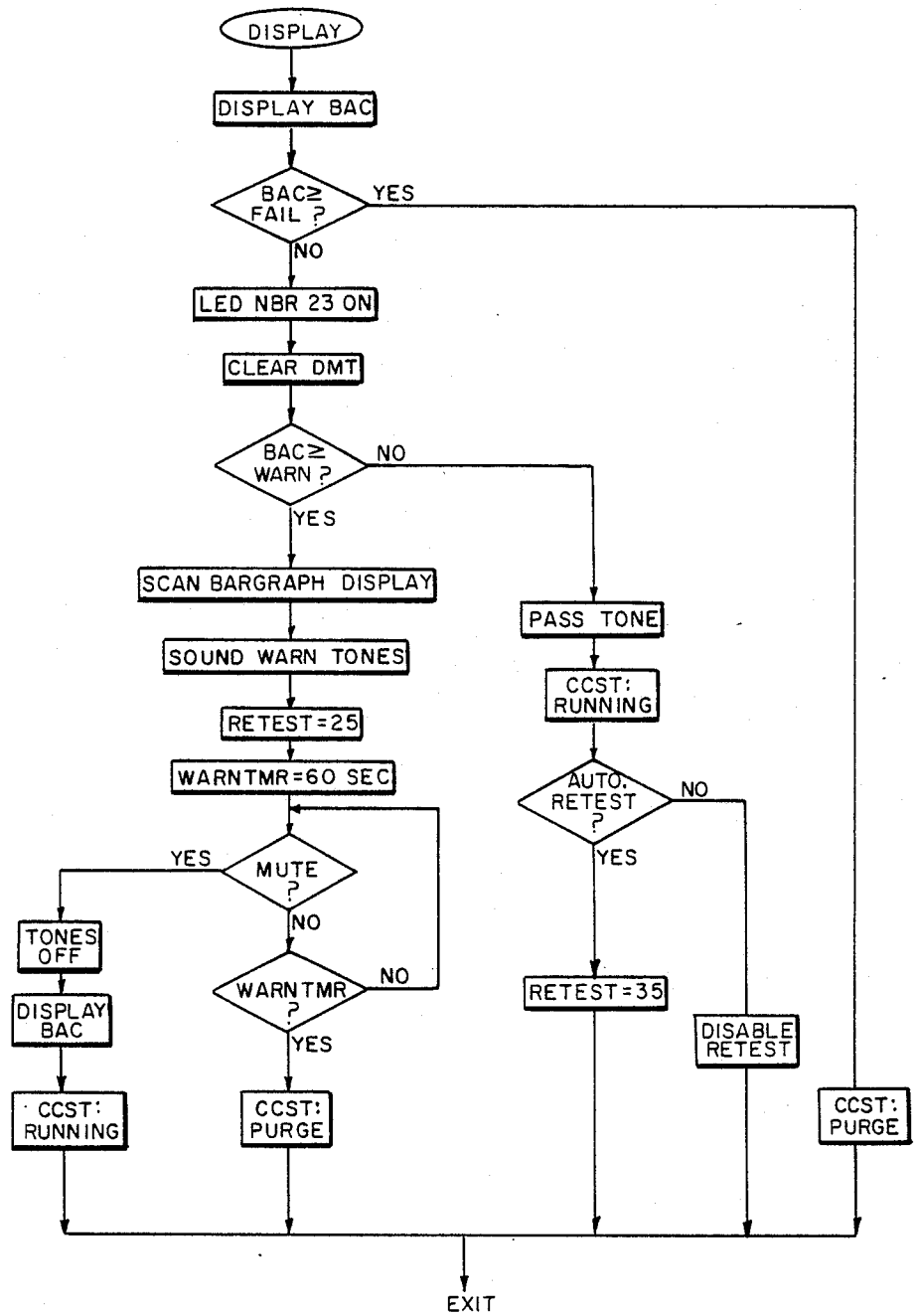
FIG. 20 is a diagram illustrating the DISPLAY state.

Referring now to FIG. 20, the DISPLAY state will now be described in further detail. The DISPLAY state commences by displaying the BAC value computed previously in the BLOW state. This is accomplished by way of display 22 in conjunction with the indicia disposed beneath the spaces lying between its LEDs 25–34. LEDs 25–34 operate as a bar graph display upon which the maximum BAC level found not to be exceeded is indicated by lighting all LED elements to the left of the indicia corresponding to that level. The indicia conveniently express blood alcohol content (BAC) in terms of percent, milligram percent, or other arbitrary units. For the sake of illustration, the bar graph display 22 shown in FIG. 1 is provided with indicia corresponding to percent BAC in increments of 0.01%. Bar graph display 22 is configured consistently with the PASS and FAIL limits which may be selected from several available options according to the strapping of header 173 in the manner described earlier. For example, as can be seen with additional reference to FIG. 1, a PASS limit can be selected such that a BAC level of less than 0.02% BAC results in lighting one or both green LEDs 25 or 26 as appropriate. In a similar manner, a FAIL limit of 0.05% can be selected such that any reading of 0.05% BAC or greater results in lighting of all LEDs up to and including one or more red LEDs 30–34. BAC readings lying between the PASS and FAIL limits are indicated by lighting both green LEDs 25 and 26 as well as one or more yellow LEDs 27, 28, and/or 29.

The computed BAC value is then compared with the predetermined FAIL limit. If the FAIL limit is met or exceeded, the PURGE state is reentered. Provided the FAIL level is not exceeded, passing of the BAC portion of the test is further indicated by the lighting of indicator LED 23. Assuming the FAIL limit was not met or exceeded, demerit timer DMT is cleared by writing a zero minute value to the appropriate memory location of EEPROM 195. Thus, after one successfully passes both the BAC measurement and ID passes of the test, prior failures of either phase do not limit the number of times one may attempt subsequent tests. Clearing of demerit timer DMT in effect "wipes the slate clean" Of course, subsequent failures will cause DMT to be incremented in the manner described earlier and the DEMERIT LOCKOUT state will be entered if a sufficient number of later tests are failed within the DMT limits described earlier.

Figure 22:
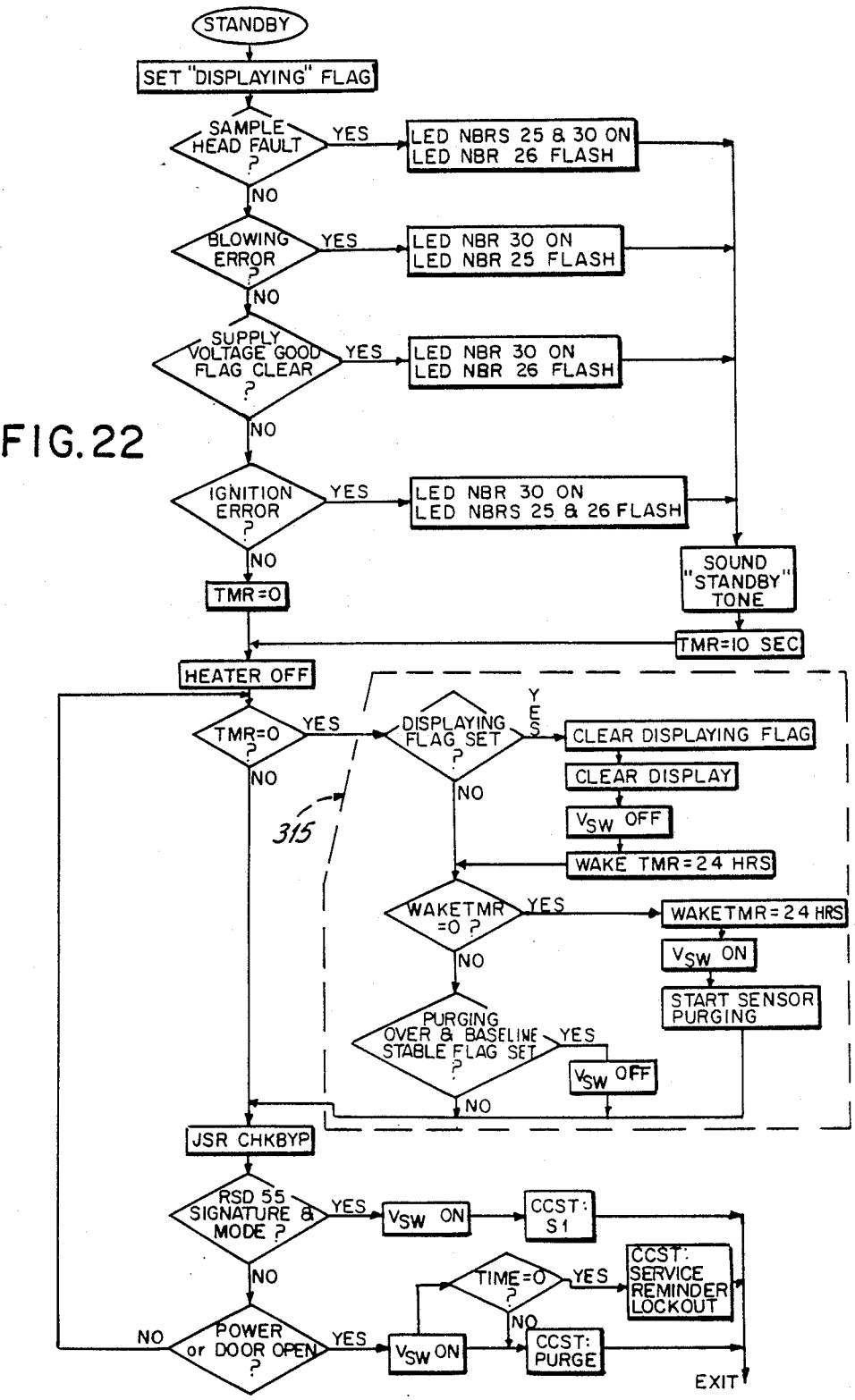
FIG. 22 is a diagram illustrating the STANDBY state.

The computed BAC level is next compared with the predetermined WARN limit. If the WARN limit is neither met nor exceeded, a distinctive "pass" tone is sounded by beeper 8 and the RUN state to be described next in connection with FIG. 22 is entered. If header 173 is strapped as required to select automatic retest, a repeat breath test will be required within a predetermined RETEST interval such as 35 minutes even though the BAC level was determined to lie below the WARN level. This feature is used where it is desired to deter drinking after a breath test has been passed and the vehicle started. If an automatic retest is not to be required, header 173 is strapped accordingly resulting in disablement of the RETEST timer except as it is used in the situation to be described below.

In the event the computed BAC level meets or exceeds the preselected WARN level, bar graph display 22 is repeatedly scanned and a distinctive "warn" tone sequence is sounded by beeper 8. As bar graph display 22 is scanned, each LED, beginning with LED 25 and continuing through the yellow LED 27, 28 or 29 indicating the measured BAC level, is lighted individually in an ascending sequence. This striking visual and audible display continues indefinitely until MUTE button 20 is pressed. By pressing MUTE button 26, the operator/test subject acknowledges that he or she has been advised that a significant blood alcohol level has been detected. Since blood alcohol content can continue to rise for some time after imbibing, operators are instructed, preferably at the time sobriety interlock 1 is installed, that sound discretion and caution should be used in deciding whether or not to drive in the event a test results in the WARN indication just described. If the operator/test subject fails to acknowledge the WARN indication within a definite period specified by a timer, WARNTMR, which may be set for example to 60 seconds, the PURGE state is reentered thereby precluding starting of the vehicle unless a subsequent test is passed. Provided the WARN indication is acknowledged by pressing MUTE button 20 before WARNTMR times out, the "warn" tone is terminated and the BAC measurement is displayed in normal (i.e. continuously lighted) bar graph format upon display 22. Thereafter, the RUN state is entered.

Figure 21A:
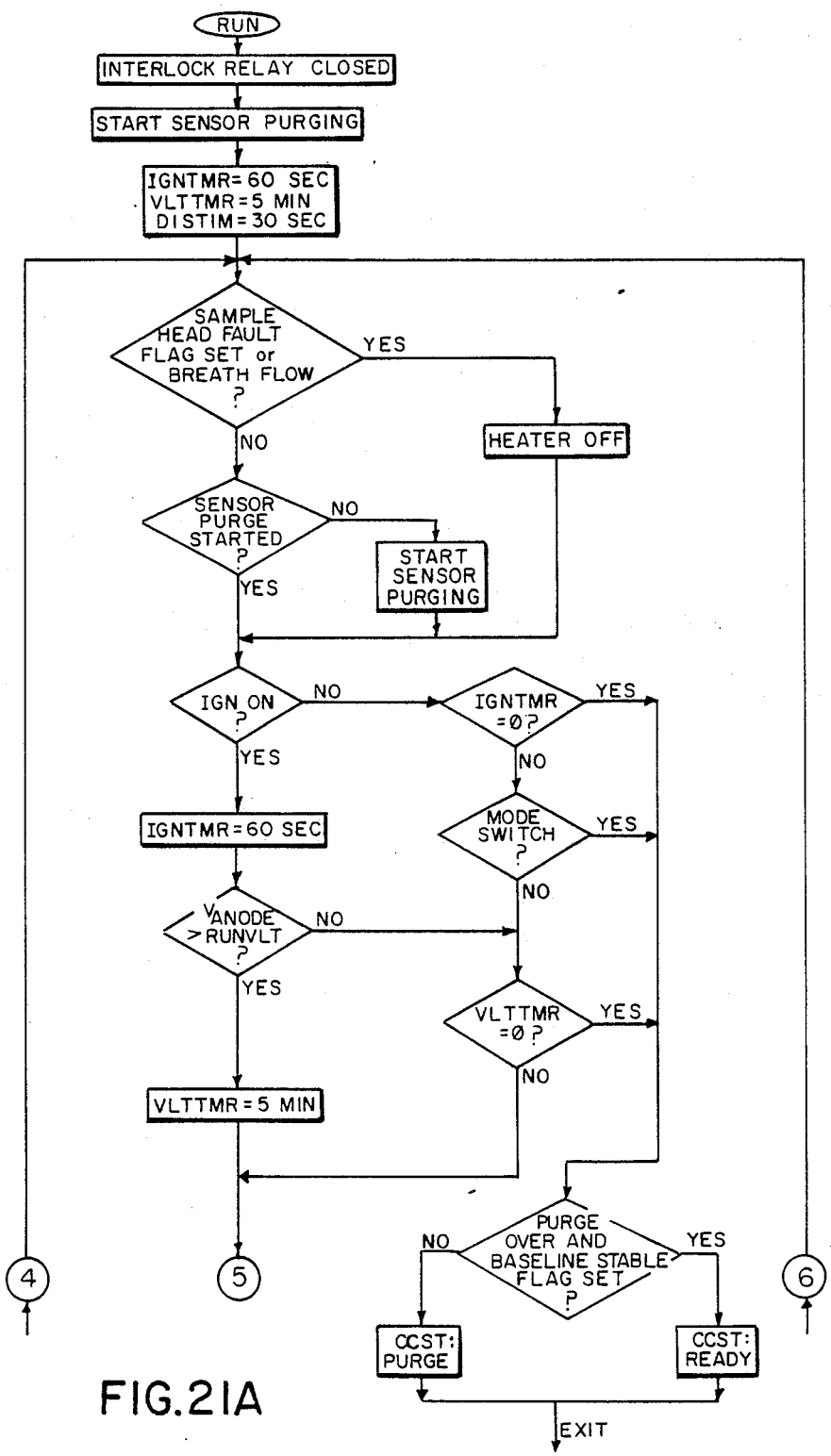
FIG. 21A and FIG. 21B are diagrams which together illustrate the RUN state.
Figure 21B:
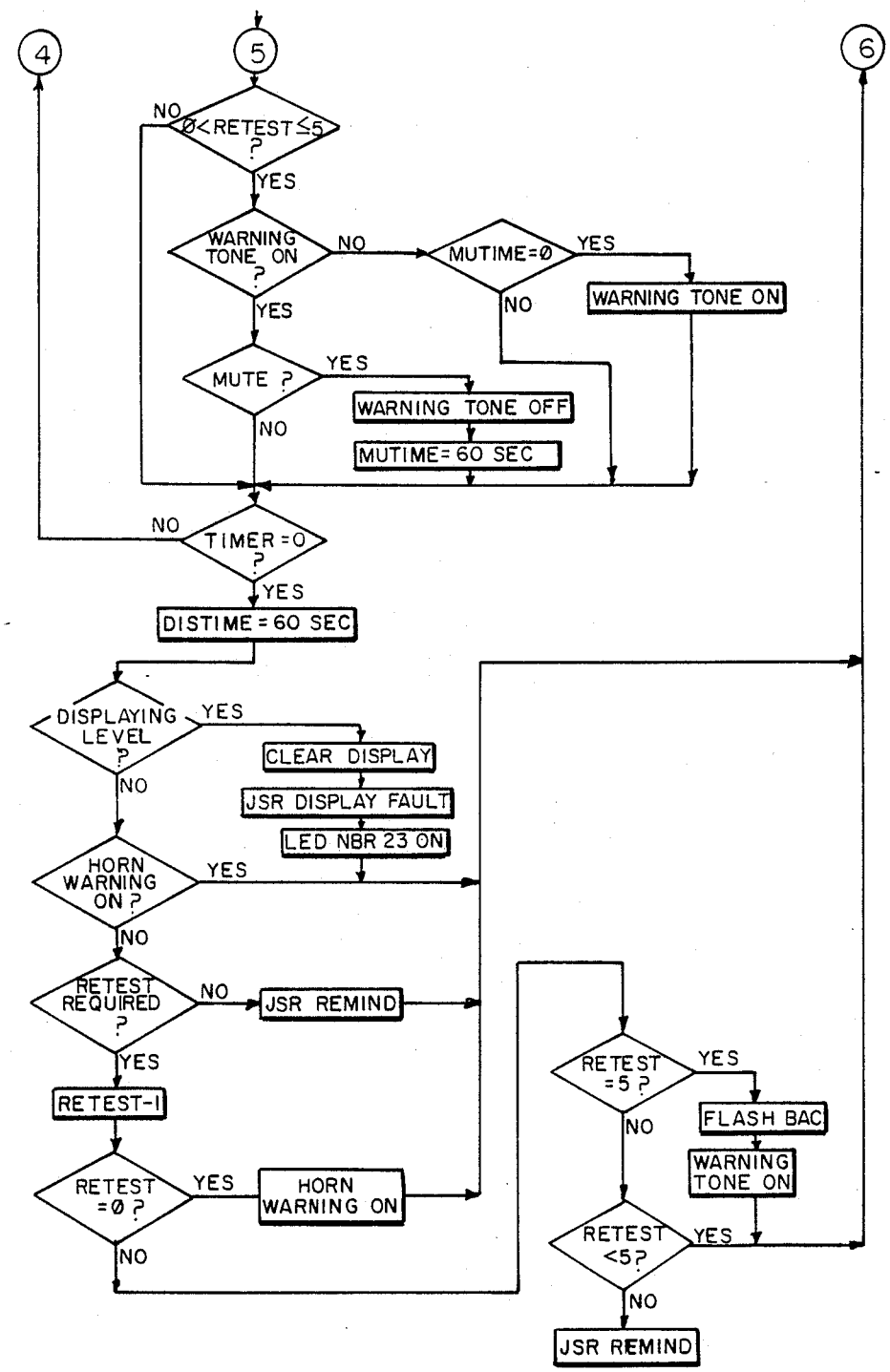

Referring now to FIG. 21, upon entry of the RUN state, interlock relay 131 is closed under the control of microprocessor 160 by way of ILK line 68 in the manner previously described with reference to FIG. 3. This permits the vehicle to be started in the normal manner as long as relay 131 is closed. To avoid or reduce the length of time required to PURGE sensor 200 should a new test be required soon, purging of alcohol sensor 200 through the energization of heater 202 in the manner described earlier is again commenced. A series of timers is then initialized. The first of these, IGNTMR is set to a desired interval such as 60 seconds during which restarting of the vehicle without a new test will be permitted after maintained ignition switch contacts 119 have been opened. In a similar fashion, the voltage timer VLTTMR is set to a desired interval such as 5 minutes. As noted previously in connection with FIG. 14, in the event the vehicle stalls it can be restarted without requiring the operator to pass a new test provided that neither IGNTMR nor VLTTMR have timed out. A third timer, DISTIM is set to a desired value such as 30 seconds during which it is desired to continue the display of the BAC level on display 22.

After the above timers are set, the status of the "sampling head fault" flag and pressure switch 208 are interrogated. If pressure switch 208 indicates breath flow or if the "sampling head fault" flag is set, heater 202 is switched off. Otherwise, a check is made to see whether purging of sensor 200 has commenced. If it has not, a new attempt to effect purging is initiated. Thereafter, IGN line 70 is interrogated to determine whether the vehicle ignition is on. If the ignition is on, ignition timer IGNTMR is reset to its initial value. If the ignition is off, a check is made to determine whether IGNTMR has timed out. If it has, restarting of the vehicle without a new test is not permitted and the READY state is entered if the purging of sensor 200 is complete and its baseline is stable as indicated by the set status of the "baseline stable" flag. If the baseline is not stable i.e., the "baseline stable" flag is cleared, a new purge of sensor 200 is instituted by way of the PURGE state. If the vehicle stalls or is turned off either the READY state or the PURGE state is entered after IGNTMR or VLTTMR times out. The need to wait for the ignition timer IGNTMR to time out can be avoided by pressing MODE switch 21. After ignition timer IGNTMR is reset to its initial value following the interrogation of IGN line 70, $V_{ANODE}$ 61 is sensed and compared with the threshold RUNVLT previously stored in EEPROM 195 upon installation of sobriety interlock 1 in the manner previously explained in connection with the description of first remote service device 55. So long as IGN line 70 appears active and $V_{ANODE}$ exceeds the run voltage threshold RUNVLT, the vehicle is assumed to be running and voltage timer VLTTMR is reset to its initial value. On the other hand, should $V_{ANODE}$ appear to fall below RUNVLT, the vehicle is assumed to be not running and the status of timer VLTTMR is checked. Again, if VLTTMR has timed out either the PURGE state or the READY state is entered depending on whether a successful PURGE has previously been completed.

Recall that the RETEST timer is always active if the BAC phase of the test resulted in a WARN indication. It is also active if the BAC measurement phase of the test was passed and the automatic RETEST option has been selected by appropriately strapping header 173. In the former case, the RETEST timer is initially set to a value such as 25 minutes whereas in the latter case RETEST is set to 35 minutes. If the RETEST timer is active its status is checked in the running state. When between zero and 5 minutes remain on the RETEST timer, the distinctive "warning" tone is sounded by beeper 8 to remind the driver that a retest is due to be taken. Upon hearing the "warning" tone, the driver should pull off the road at the earliest safe opportunity, turn the vehicle ignition off and perform a new test to restart the vehicle. The "warning" tone can be silenced for a period such as 60 seconds determined by a timer, MUTIME. Once MUTIME equals zero, the "warning"

tone will again sound unless the MUTE button 20 is again pressed to silence it. It should be noted however that silencing of the "warning" tone does not stop or reset the RETEST timer. After completing the above functions, timer DISTIME is checked and the program loops back as indicated until DISTIME times out. This has the effect of maintaining the result of the BAC test on the bar graph display 22 for the first time period, such as 30 seconds, to which timer DISTIME was first set. Once DISTIME times out for the first time, the program drops out of the first loop and DISTIME is reset to a second value such as 60 seconds. The second DISTIME setting determines the intervals at which the RETEST timer will be decremented. If bar graph display 22 continues to display the BAC level, display 22 is cleared and LED 23 is turned on after executing the DISPLAYFAULT subroutine described earlier. After lighting LED 23 the program continuously loops as indicated. Thus, running of the vehicle is not interrupted once running commences. Even if a retest is not taken when required only audible and/or visual indications are provided. For safety, running of the vehicle is never stopped by the control action of sobriety interlock 1. Interlock relay 131 is reopened only upon reentry of the PURGE or READY states after running of the vehicle has been sensed to have ceased and IGNTMR and/or VLTTMR have timed out.

Assuming that display 22 had previously been cleared, the program checks to determine whether the vehicle horn is being sounded by microprocessor 160. If so, the program loops as shown. Otherwise, a check is made to determine whether a retest is required. If a retest is not required, subroutine REMIND is executed and the program loops back as indicated If a retest is required, the retest timer RETEST is decremented and checked. If the RETEST timer has timed out the vehicle horn is sounded by microprocessor 160 by controlling HRN line 69 in the manner previously described with reference to FIG. 3. The horn sounds if the operator/test subject fails to pull over and turn off the ignition before the RETEST timer times out. The horn cannot be muted except by turning off the ignition and either subsequently pressing MODE push button 21 or waiting for ignition timer IGNTMR to time out.

A number of indications are provided to prompt the operator to retest or endure the blasting of the vehicle horn which will likely capture the notice of fellow motorists and possibly, the police Except during the last 5 minutes of a retest period, display 22 indicates any appropriate indications as provided by way of the REMIND subroutine. However, during the last 5 minutes defined by the RETEST timer, the BAC reading flashes on display 22 in conjunction with sounding of the "warning" tone by beeper 8. It is reiterated that in the event a retest is not taken before the RETEST timer times out, interlock 1 does not cause the vehicle to stop or otherwise impair its normal operation except for sounding the vehicle horn.

Referring now to FIG. 22 the STANDBY state is described in further detail. The "displaying" flag is set immediately upon entry of the STANDBY state. If the STANDBY state is entered because of a fault or error condition, the nature of the display is indicated by way of a characteristic display appearing on display 22. Concurrently with the visual display, a distinctive "standby" tone is audibly sounded by beeper 8. The display persists for a period, such as 10 seconds, determined by the setting of a utility timer TMR. If a fault associated with sampling head 3 occurs, LEDs 25 and 30 are lighted and LED 26 flashes. Such a fault may indicate that sampling head 3 is not properly connected to control module 2 or that either alcohol sensor 200 or sensor heater 202 are not operational. In the event a person blows breath into mouthpiece 40 during purging of alcohol sensor 200 a "blowing error" is indicated by the lighting of LED 30 and the flashing of LED 25. If power supply $V_{ANODE}$ 61 is not within an acceptable range, a "supply voltage good" flag will be clear rather than set. In that case, LED 30 is lighted while LED 26 flashes. The setting and clearing of the "supply voltage good" flag will be further explained in connection with the CHKSUPPLY routine of FIG. 31. Finally, if IGN line 70 was active while interlock 1 was in the READY state, an ignition error is indicated by lighting LED 30 and flashing LEDs 25 and 26. After timer TMR has timed out, heater 202 is turned off and a subloop 315 to be described momentarily is executed. Assuming that the STANDBY state is entered not due to one of the above fault conditions, but rather due to the pressing of POWER push button 19 or the timing out of the power down timer PDT then, there is no visible or audible cue. In this event, subloop 315 is entered immediately after turning heater 202 off. Otherwise subroutine CHKBYP is called directly and executed in the manner previously described. Sobriety interlock 1 enters the S1 state described earlier and turns power supply $V_{SW}$ 63 on if microprocessor 160 senses the connection of a first remote service device 55 and the pressing of MODE button 21. It will be recalled that connection of first remote service device 55 is indicated by the presence of a characteristic RSD 55 signature signal on line PSW 102. Assuming the S1 state is not entered, interlock 1 checks to determine whether it should be powered up as indicated by either the pressing of POWER switch 19 or opening of the vehicle door. Opening of the vehicle door is sensed according to a predetermined drop in the voltage of power supply $V_{ANODE}$ 61 in a manner which will be more fully explained in connection with the description of the CHKSUPPLY subroutine illustrated in FIG. 31. Should either of those events be sensed, power supply $V_{SW}$ 63 is turned on and operation in the PURGE state commences if the service reminder timer, TIME has not timed out. If TIME has timed out, the SERVICE REMINDER LOCKOUT state is entered. Assuming that neither the pressing of POWER push button 19 nor the opening of the vehicle door are sensed, the program loops back as indicated to check the status of timer TMR. When timer TMR times out, subloop 315, which will now be described, is entered.

The first time through subloop 315, the "displaying" flag is immediately cleared as is bar graph display 22. To minimize the drain on vehicle battery 108, power supply $V_{SW}$ 63 is then switched off. As can be appreciated for example by inspection of FIG. 2, switching off power supply $V_{SW}$ 63 is effective to cut off the flow of power to sampling head 3 as well as to audio output 50, thereby eliminating the power drain associated with those components. Since power supplies $V_{ANODE}$ 61 and $V_{MAIN}$ 62 remain on, the circuitry operated by those supplies is not affected.

Figure 23:
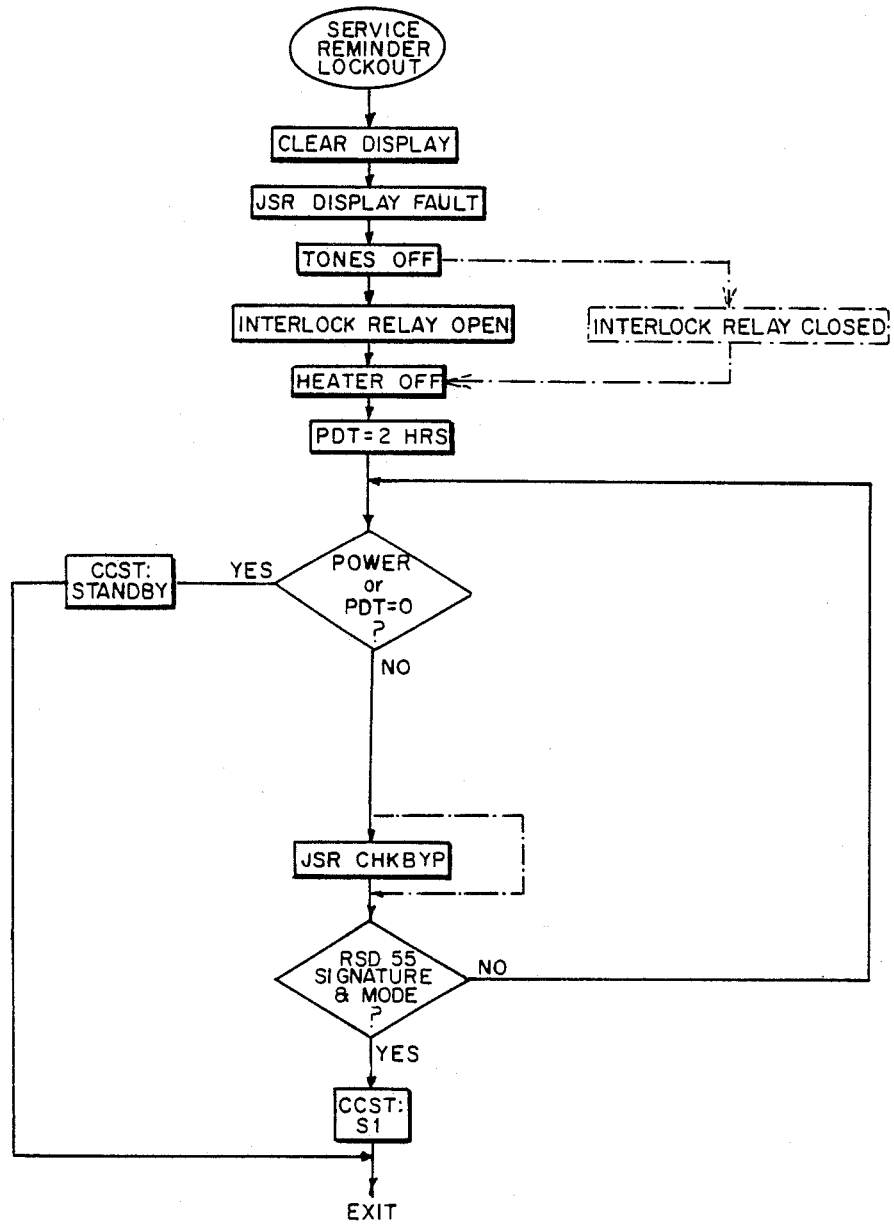
FIG. 23 is a diagram illustrating the SERVICE REMINDER LOCKOUT state.

It has been discovered that the accuracy of alcohol measurements can be adversely affected if alcohol sensor 200 is used after remaining idle for extended periods of time. In order to overcome this problem, the invention contemplates purging sensor 200 at intervals of time which are frequent enough to avoid significant impairment of the accuracy of sensor 200 yet, as far apart as possible to maximize conservation of vehicle battery 108. In the present embodiment, this is facilitated by a software timer, WAKETMR which can be suitably set to define a 24 hour cycle. After power supply $V_{SW}$ 63 is switched off, WAKETMR is initially set to a desired value such as 24 hours. Thereafter, its status is checked. If WAKETMR has not timed out, supply $V_{SW}$ 63 remains switched off. When WAKETMR times out, WAKETMR is reset to its initial value, supply $V_{SW}$ 63 is turned on and purging of sensor 200 by energizing heater 202 in the manner described earlier is commenced. Once purging has continued long enough to stabilize the baseline signal of alcohol sensor 200 (as evidenced by the "baseline stable" flag being set) $V_{SW}$ 63 is switched off again. Thus, every 24 hours interlock 1 "awakens" from its low power drain STANDBY condition just long enough to purge alcohol sensor 200. A 24 hour cycle has been found to be sufficiently long to significantly conserve vehicle battery 108, yet short enough to help avoid degradation of the performance of alcohol sensor 200. The SERVICE REMINDER LOCKOUT state will now be described in further detail with reference to FIG. 23.

In the event an operator fails to obtain authorized service before service reminder timer, TIME times out, the SERVICE REMINDER LOCKOUT state is entered. Upon entering the SERVICE REMINDER LOCKOUT state, display 22 is cleared, beeper 8 is silenced and subroutine DISPLAYFAULT is entered to display any applicable faults. As inspection of FIG. 14 makes clear, once the SERVICE REMINDER LOCKOUT state is entered, the RUN state cannot be entered unless and until service reminder timer, TIME is reset to a nonzero value.

As previously noted in connection with the description of FIG. 14, it may be desirable, depending on the circumstances under which interlock 1 is to be used, to cause interlock 1 to effectively bypass itself while in the SERVICE REMINDER LOCKOUT state. If this alternative is desired, interlock relay 131 is closed (as indicated in broken lines in FIG. 23). To avoid excess power drain on vehicle battery 108, relay 131 is preferably closed only when IGN line 70 is active. As a result or relay 131 being closed (either continuously or only when IGN line 70 is active), interlock 1 cannot be used to restrict starting of the vehicle for an indefinite length of time until the service reminder timer, TIME is reset. Such operation is usually desired only if use of interlock 1 is voluntary on the part of the user. If on the other hand the use of interlock 1 is compelled, relay 131 is preferably opened in the SERVICE REMINDER LOCKOUT state, thereby inhibiting starting of the vehicle indefinitely pending are setting of service reminder timer, TIME.

After interlock relay 131 is either opened or closed, heater 202 is deenergized and a power down timer PDT is set to a desired interval such as 2 hours. Once the power down timer PDT times out or if POWER push button 19 is pressed, the STANDBY state is entered. Otherwise, the SERVICE REMINDER LOCKOUT state continues by calling subroutine CHKBYP. As described previously with reference to FIG. 29, the CHKBYP subroutine is effective to turn on LED 32 if a bypass event has occurred. Note however, that the CHKBYP subroutine is not called where, according to the alternative discussed above, interlock relay 131 is to be closed rather than opened in the SERVICE RE-MINDER LOCKOUT state. Upon returning from subroutine CHKBYP, if it is called, the software continuously checks for the presence of the RSD 55 signature signal (to determine whether a first remote service device 55 is connected) and MODE button 21 simultaneously pushed. If so, the S1 state is entered which permits the service reminder timer TIME to be reset to a nonzero value. The only other way that the service reminder timer can be reset is to enter the S2 state by way of the BOOT UP state as previously described with reference to FIG. 14.

Figure 25:
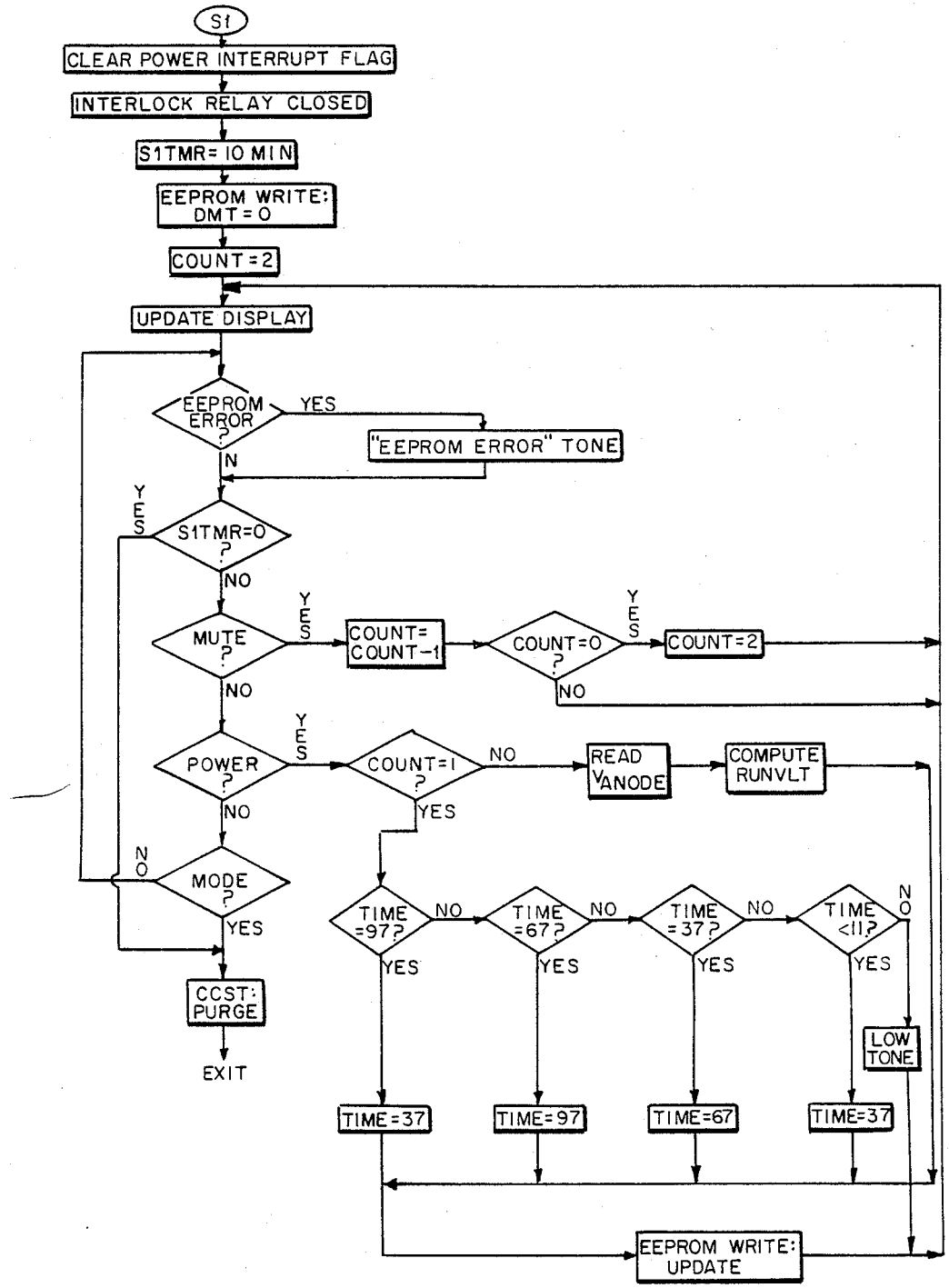
FIG. 25 is a diagram illustrating the S1 state.

With reference now to FIG. 25 the S1 state will now be described in further detail. As noted previously in connection with the description of FIG. 14, the S1 state is a restricted access state in which a number of significant service functions can be performed. In particular, power supply $V_{ANODE}$ 61 can be read and a corresponding run voltage threshold value RUNVLT stored in memory. It will be recalled that during operation of interlock 1, RUNVLT is used as a threshold value to be compared with the voltage appearing at power supply $V_{ANODE}$ 61 as one criterion entered to determine whether the vehicle is actually running. The S1 state also permits the service reminder timer, TIME to be set to one of several selectable intervals.

Upon entry of the S1 state, the "power interrupt" flag is automatically cleared. Unless this function is performed after sobriety interlock 1 is disconnected from a power source (such as vehicle battery 108) and subsequently reconnected, it will be recalled that power interrupt LED 33 will be lighted upon execution of the DISPLAYFAULT subroutine. In the event LED 33 is lighted when the vehicle to which sobriety interlock is connected is brought in for servicing of sobriety interlock 1, service personnel will be advised that sobriety interlock 1 has been disconnected from power at some time since it was installed or last serviced. This will indicate the possibility that the vehicle was started without proper use of sobriety interlock 1. In order to be able to read the voltage $V_{ANODE}$ 61 while the vehicle is running, it is necessary that interlock relay 131 be closed so that the vehicle can run. Accordingly, interlock relay 131 is closed automatically upon entry of the S1 state. Since operation in the S1 state involves the closing of interlock relay 131, the time during which sobriety interlock 1 can operate in the S1 state is preferably limited to a relatively short length of time adequate to allow service personnel to perform necessary service functions. This is accomplished by means of a timer S1TMR which is set to a desired interval such as 10 minutes. Once S1TMR times out, the S1 state is automatically exited. Entry of the S1 state is also automatically effective to clear demerit timer DMT. This is accomplished by writing a zero value to the appropriate memory location in EEPROM 195.

Once the S1 state is entered, sobriety interlock 1 can be made to perform several special functions through proper operation of the MUTE, POWER and MODE push buttons 20, 19, 21 as will now be described with continuing reference to FIG. 25. The operations capable of being performed by sobriety interlock 1 at any given time in the S1 state are tracked by means of a dummy counter, COUNT. When COUNT equals 1, the service reminder timer, TIME can be read or set subject to certain limitations to be explained. When COUNT equals 2, the RUNVLT threshold value can be read or set. When COUNT equals 1, indicating that the operational mode for setting and/or reading the service reminder timer, TIME has been selected, display 22 so indicates by illuminating the first green LED 25. If on the other hand, COUNT equals 2, indicating that RUNVLT is to be read or set, display 22 so indicates by illuminating the second green LED 26. Initially, COUNT is set to some arbitrary value such as 2. When COUNT equals 2, the value of RUNVLT is displayed in reverse binary form by way of LEDs 27–34. By reverse binary form, it is meant that the least significant bit is indicated by LED 27 while the most significant bit is indicated by LED 34. A logical 1 value of each respective bit is indicated by lighting the corresponding LED. After display 22 is updated, any invalid read or write operations are audibly indicated by sounding the "eeprom error" tone by way of beeper 8. The status of timer S1TMR is then checked. If the timer has timed out, the S1 state is automatically exited and the PURGE state entered. Provided the S1TMR has not timed out, microprocessor 160 scans for pressing of MUTE, POWER, or MODE push buttons 20, 19 and 21, respectively. Whenever the MODE button 21 is pressed, the S1 state is exited and the PURGE state entered. Whenever MUTE push button 20 is pressed, COUNT is decremented in ring fashion and display 22 is updated to operate as described above in accordance with the operational mode corresponding to the currently selected COUNT value. Pressing of POWER push button 19 performs different functions depending on the current value of COUNT. When COUNT equals 1, the current value of service reminder timer is indicated by display 22 in the following manner. If TIME equals 37 days, LED 30 is lighted. If TIME equals 67 days, LEDs 30 and 31 are lighted. If TIME equals 97 days, LEDs 30, 31 and 32 are lighted. If the current value of the service reminder timer, TIME is some value other than 37, 67 or 97 days, none of LEDs 30–32 will be lighted. When the service reminder timer setting mode is selected (i.e. COUNT equals 1) pressing of POWER push button 19 will reset TIME to 37 days if its initial value was 97 days or, to 97 days if its initial value was 67 days or, to 67 days if its initial value was 37 days. If the initial value of the service reminder timer, TIME is less than 11 days, pressing of power push button 19 causes TIME to be reset to a value of 37 days as indicated. Subsequent pressings of POWER push button 19 will cause TIME to cycle through 67, 97 and 37 day settings in ring fashion in the manner described above. If the value of TIME is not one of 97, 67, or less than 11 days, its value cannot be changed in the S1 state. This provides additional security in the event the S1 state is somehow accessed by other than authorized service personnel. Beeper 8 sounds a low tone upon pressing POWER button 19 to indicate an error if TIME cannot be reset. As the value of TIME is updated, its value is written to EEPROM 195. Thereafter the program loops back to update display 22 in the manner described above.

Assuming that POWER push button 19 is pressed when COUNT does not equal 1 (i.e. COUNT equals 2 $V_{ANODE}$ 61 is read at the moment POWER push button 19 is pressed and a corresponding run voltage value, RUNVLT is computed. This is accomplished automatically by microprocessor 160 which does so by subtracting a safety factor such as 50 millivolts from the value of $V_{ANODE}$ 61. The value of RUNVLT so computed is then written to EEPROM 195 to update it and display 22 is updated in the manner previously described. When sobriety interlock 1 is installed in a vehicle, RUNVLT should be set while the vehicle is running with as many of the vehicles lights, horn, accessories and the like drawing power as is found to result in the lowest possible voltage reading at $V_{ANODE}$ 61. This technique along with the safety factor subtracted to compute RUNVLT helps to ensure that sobriety interlock 1 will not interpret the vehicle as off when it is actually running.

Figure 26:
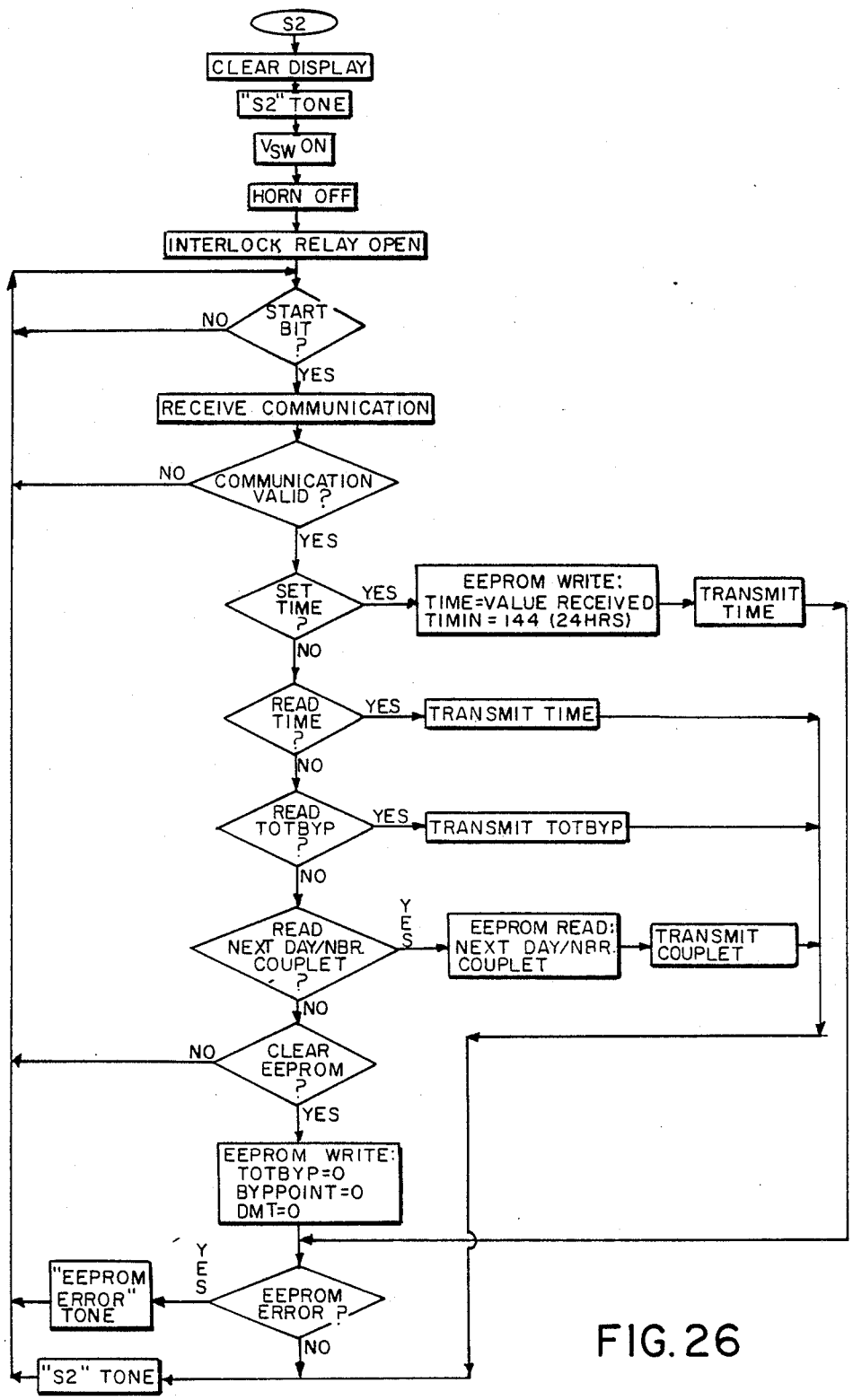
FIG. 26 is a diagram illustrating the S2 state.

Referring now to FIG. 26, restricted access state S2 will now be described in further detail. Upon entry of the S2 state, all LEDs including those of display 22 are cleared and a distinctive "s2" tone is sounded by beeper 8. Power supply $V_{SW}$ is turned on, the vehicle horn turned off, and interlock relay 131 opened. Microprocessor 160 then awaits communication from second remote service device 56. Each such communication begins with an identifying start bit and includes one of several command words. Among these command words are instructions to set the service reminder timer TIME, read the service reminder timer TIME, read the total number of bypass events detected and stored in memory TOTBYP, read the next DAY/NUMBER couplet, and clear certain locations within EEPROM 195. In addition to the command word the communication from second remote service device 56 also includes a data word accompanying the command word where appropriate. For example, when a command to set the service reminder timer, TIME is given, the value in days to which the timer is desired to be set is also transmitted. Upon receipt of one of the above types of communications, a check is performed to determine whether the communication is valid. This may consist of a parity check as well as comparing the command word to a list of valid command words. If the command word received does not correspond to one of the known command words, or parity is improper, the communication is deemed invalid and is ignored. In that event, microprocessor 160 simply awaits the next communication. Assuming the received communication is valid, microprocessor 160 interprets the command and executes it.

When a command to set the service reminder timer, TIME is received, the DAY value accompanying the command is written to EEPROM 195. Also, timer TIMIN, which decrements at 1 count at 10 minute intervals, is loaded with a value of 144. This corresponds to a full day since there are 144 10 minute intervals in a 24 hour period. When TIMIN times out it is automatically reset to 144 and the service reminder timer, TIME is decremented by 1 day. Thus, if service reminder timer, TIME is loaded with a value of 37 days, and TIMIN is loaded with a value of 144 at the same time, TIME will decrement to 36 days, a full 24 hours after being loaded. After EEPROM 195 is updated, the value of TIME is read therefrom and transmitted to second remote service device to confirm proper receipt of the transmission. If the value written to EEPROM 195 does not correspond to the value received from second remote service device 56 by microprocessor 160, an "eeprom error" tone is sounded by beeper 8, and a new transmission is awaited. Assuming the two values do correspond however, the distinctive "s2" tone is sounded and a further transmission awaited.

If the transmission received is an instruction to read either the value of the service reminder timer, TIME or the total number of recorded bypass events, TOTBYP the appropriate value is read and transmitted to second remote service device 56 for confirmation. The "s2" tone is sounded at the end of the transmission. Interlock 1 can also be instructed to transmit the next DAY/-

NUMBER couplet of recorded bypass events. When such an instruction is received and appears valid, a single couplet is read from EEPROM 195. Upon being read, the couplet is transmitted to second remote service device 56. Again, following the transmission, the "s2" tone is sounded and a further transmission is awaited. Couplets are read out on a first-in first-out (FIFO) basis so that the oldest couplets are the first to be read.

Interlock 1 is also capable of interpreting and executing a command to clear certain registers within EEPROM 195. When such a command is received, TOTBYP, BYPPOINT, and DMT are each written to EEPROM as zero values. It will be recalled that BYPPOINT is a pointer to the next available memory location for storing DAY/NUMBER couplets. By setting BYPPOINT to zero, the next couplet read will be written over any values previously stored in EEPROM 195. Accordingly, setting BYPPOINT to zero has the same effect as clearing all previously recorded couplets. It should be noted that the command to clear EEPROM 195 does not effect the service reminder timer, TIME or the run voltage threshold RUNVLT. Should an error occur with respect to any of the foregoing write operations, the "eeprom error" tone is sounded. If no error is detected, the "s2" tone is sounded. Thereafter, interlock 1 will continue to await further instructions from second remote service device 56. The S2 state can be exited only by disconnecting second remote service device 56 and effecting a hardware reset of microprocessor 160. This can be accomplished for example, by momentarily disconnecting control module 2 from vehicle battery 108.

Figure 27:
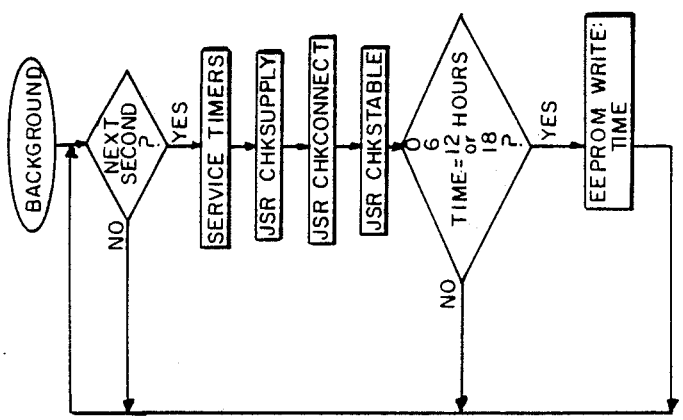
FIG. 27 is a diagram illustrating the BACKGROUND routine.

It should be understood that the software executed by microprocessor 160 defines a multi-tasking architecture. Accordingly, in addition to the state transitions depicted in FIG. 14 certain tasks which are not uniquely related to any individual state are constantly being performed. This is illustrated by way of a "BACKGROUND" routine which will now be described with reference to FIG. 27. As indicated there, the BACKGROUND functions are executed continuously at 1 second intervals. One important function constantly being performed is the updating of a real time clock to which the running of all the previously mentioned timers is ultimately referenced. A series of subroutines, CHKSUPPLY, CHKCONNECT and CHKSTABLE are also sequentially executed to update the status of each flag that is checked in the various states described above. These subroutines will be described in detail below with reference to FIGS. 31, 32 and 33, respectively. Finally, the current value of the service reminder timer TIME is written to EEPROM 195 every 6 hours. In the event of a power interruption, this ensures that the TIME value which will be loaded upon BOOT UP will be current to within 6 hours.

Figure 31:
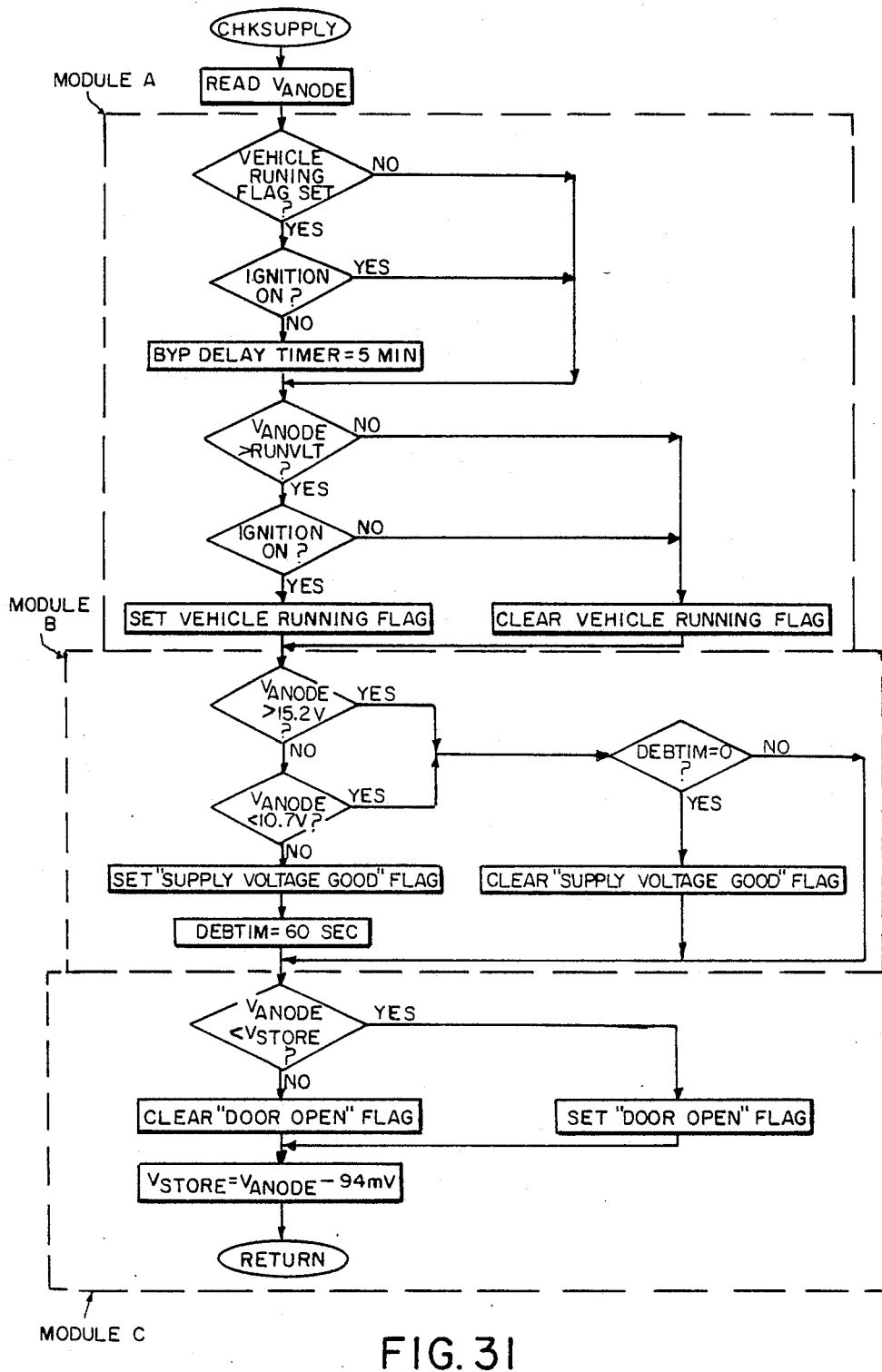
FIG. 31 is a diagram illustrating the CHKSUPPLY subroutine.

Subroutine CHKSUPPLY will now be described with reference to FIG. 31. Upon entry of CHKSUPPLY, microprocessor 160 reads the voltage of supply $V_{ANODE}$ 61 by reading the data appearing on line AD5 after selecting channel X1 of MUX 250. After the $V_{ANODE}$ voltage has been read and stored, a series of three modules designated A, B and C, are executed.

The function of module A is to determine whether the vehicle is currently running. If the vehicle is running, a "vehicle running" flag is set. If the vehicle is not running, the "vehicle running" flag is cleared. Upon entry of module A the current status of the "vehicle running" flag is checked as is the status of the vehicle ignition. If the vehicle running flag is set and the ignition is off, the bypass delay timer BYP is set. The "vehicle running" flag is set if both (a) the vehicle ignition is on (IGN line 70 active) and (b) the voltage appearing at $V_{ANODE}$ 61 exceeds RUNVLT. Otherwise, this flag is cleared.

Module B operates to determine whether the voltage at power supply $V_{ANODE}$ 61 lies within acceptable operating voltage limits. If the $V_{ANODE}$ voltage does not exceed a predetermined maximum limit, such as 15.2 volts, or fall below a predetermined minimum limit, such as 10.7 volts, a "supply voltage good" flag is set indicating that $V_{ANODE}$ is within proper limits. Thereafter, a debounce timer DEBTIM is set to a desired value such as 60 seconds. The debounce timer operates to prevent transient changes in the voltage at power supply $V_{ANODE}$ from affecting the operation of sobriety interlock 1. If, upon subsequent checks, the $V_{ANODE}$ voltage exceeds the predetermined maximum limit or falls below the predetermined minimum limit, the "supply voltage good" flag is cleared provided the debounce timer DEBTIM has timed out.

Module C of the CHKSUPPLY subroutine serves to automatically sense opening of the door of the vehicle in which interlock 1 is installed. As noted previously, automatic sensing of door opening is effective to power up interlock 1 just as though POWER push button 19 had been pressed. Quite simply, module C operates by comparing the voltage currently appearing at power supply $V_{ANODE}$ 61 against a stored voltage threshold $V_{STORE}$. If the $V_{ANODE}$ voltage is less than $V_{STORE}$ a "door open" flag is set indicating that the vehicle door has been opened. If, on the other hand the $V_{ANODE}$ voltage is not less than $V_{STORE}$, the "door open" flag is cleared. After setting or clearing the "door open" flag, $V_{STORE}$ is updated by setting its value equal to the current value of $V_{ANODE}$ less an offset voltage. The offset voltage should be selected to correspond to a voltage slightly higher than the voltage drop normally experienced at $V_{ANODE}$ upon the opening of the door of the vehicle. This voltage drop is caused by the automatic energization of vehicle accessories such as the interior dome light when the door is open. Applicants have found an offset voltage of about 94 millivolts to be suitable in most cases. Occasionally however, a vehicle will not be equipped such that $V_{ANODE}$ will not drop significantly upon opening the vehicle door. In such cases, sobriety interlock 1 must be manually powered up using POWER push button 19.

Figure 32:
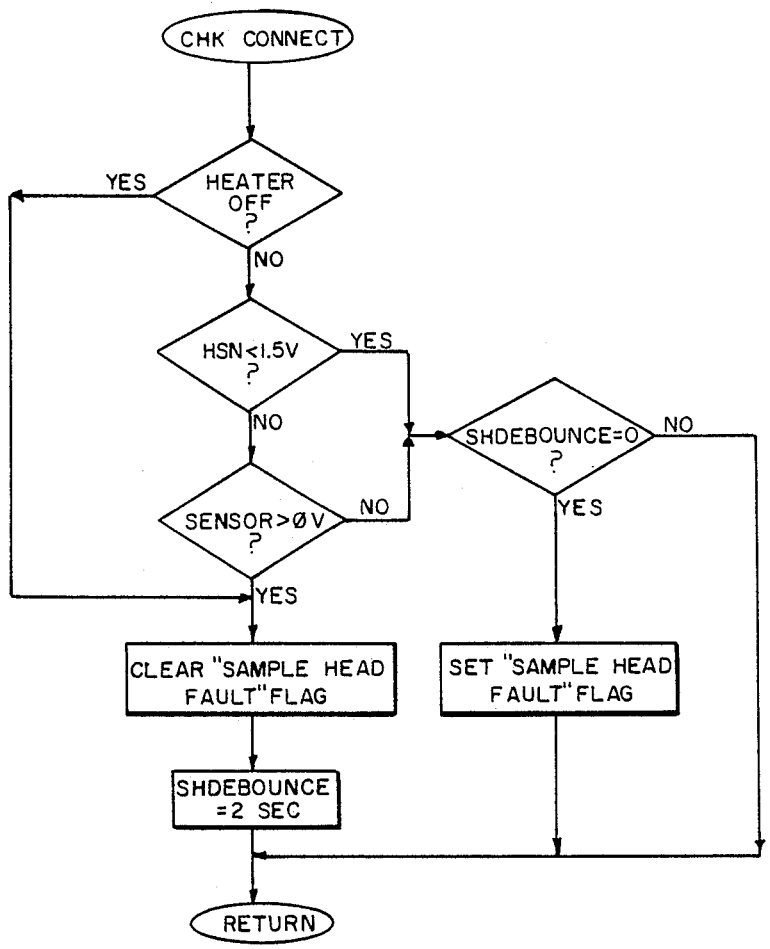
FIG. 32 is a diagram illustrating the CHKCONNECT subroutine.

Referring now to FIG. 32, the CHKCONNECT subroutine will now be described in further detail. Initially, HTC line 100 is checked to determine whether the heater 202 associated with alcohol sensor 200 should currently be off. If so, the "sampling head fault" flag is cleared and a sampling head debounce timer, SHDEBOUNCE is set to a suitable desired period, such as 2 seconds. SHDEBOUNCE serves to prevent transient faults from effecting the status of the "sampling head fault" flag. If HTC line 100 indicates that heater 202 should not be off, the voltage on HSN line 248 is read by selecting channel X3 of MUX 250 and reading line AD5 99 emanating from A/D 253. The output of alcohol sensor 200 is also read by way of channel X0 of MUX 250 and line AD5 99 of A/D 253. If HSN line 248 falls below a predetermined threshold, such as 1.5 volts, the "sampling head fault" flag is set provided timer SHDEBOUNCE has timed out. If the timer has not timed out, the "sampling head fault" flag remains in its previous state. When HSN line 248 falls below 1.5 volts, this indicates that heater 202 is disconnected or open circuited or that transistor 253 is shorted or open circuited. The integrity of alcohol sensor 200 is also checked.

In the event heater 202 is on, the output signal from alcohol sensor 200 should exceed zero volts. If it does, the "sampling head fault" flag is cleared and the SHDEBOUNCE timer is reset. Otherwise, the "sampling head fault" flag is cleared provided timer SHDEBOUNCE has timed out. A substantially zero volt output from alcohol sensor 200 under the above conditions indicates that sensor 200 is open or that sampling head 3 is not properly connected to control module 2. Any of those events are effective to cause setting of the "sampling head fault" flag.

Figure 33:
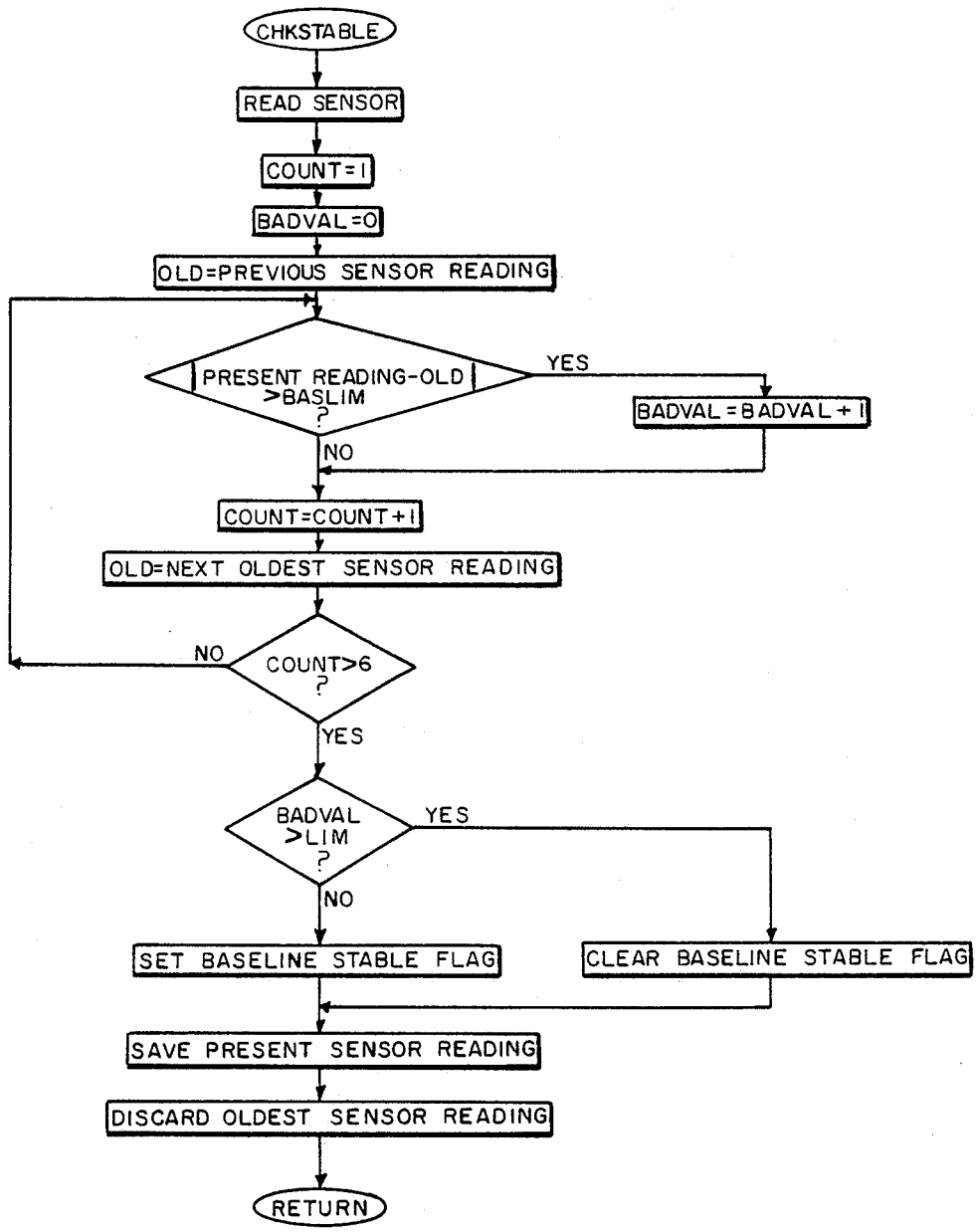
FIG. 33 is a diagram illustrating the CHKSTABLE subroutine.

Accurate BAC measurements require that the baseline output signal of alcohol sensor 200 be suitably stable prior to each test. The CHKSTABLE subroutine, which will now be described with reference to FIG. 33, is employed by sobriety interlock 1 to gauge whether the sensor baseline signal is stable within predefined limits of acceptability. The technique employed is to read the output of alcohol sensor 200 at intervals such as once each second. The most recent reading or present reading is stored in a cue which also contains some number, such as 6, of the next oldest readings. The present reading is subtracted from each one of the "OLD" readings occupying the cue and a counter, BADVAL is incremented whenever the magnitude of the difference between the present reading and one of the OLD readings exceeds a previously selected baseline tolerance limit, BASLIM. While BASLIM can be set at any reasonable value depending on the degree of stability to be required, a BASLIM value of about 17 millivolts (i.e. about 3 counts of A/D 254) has been found suitable. A counter, COUNT is used to increment the cue after each subtraction. After each reading in the cue has been individually compared with BASLIM, the content of the BADVAL counter is checked. If BADVAL exceeds a predetermined limit such as 2, the sensor baseline is not suitably stable and the "baseline stable" flag is cleared. Otherwise, that flag is set. With each subsequent reading of alcohol sensor 200 the contents of the cue are updated by storing the present reading and discarding the oldest reading.

While the above description constitutes a preferred embodiment of the present invention, it is to be understood that the invention is not limited thereby and that in light of the present disclosure of the invention, various other alternative embodiments will be apparent to persons skilled in the art. In particular, where specific numerical values are mentioned, such are by way of illustration and not limitation. It is also clear that specified component parts are amenable to various substitutions as those skilled in the art can recognize. Accordingly, it is to be understood that changes can be made without departing from the scope of the invention as particularly pointed out and distinctly claimed in the claims set forth below.

What is claimed is:

1. A sobriety breath test apparatus, comprising:
   (a) sampling means for receiving exhaled breath from a test subject, said sampling means including an alcohol sensor for generating an electrical signal related to the level of alcohol in the breath;
   (b) identity confirming means connected to said sampling means for confirming the identity of the test subject in accordance with the ability of the test subject to perform an identity-confirming act, said act requiring the delivery of breath into said sampling means;
   (c) means for reading said electrical signal to produce a first reading related the level of alcohol in a breath sample received by said sampling means and a second reading reflecting the response of said sensor to breath delivered to said sampling means during an attempt to perform said identity-confirming act, and
   (d) means for comparing said first and second readings and generating a test fail signal in the event said second reading differs from said first reading by more than a predetermined amount.

2. The apparatus of claim 1 wherein said test fail signal is generated only in the event said second reading exceeds said first reading by more than said predetermined amount.

3. The apparatus of claim 1 wherein said identity-confirming act includes blowing a plurality of bursts of breath with pauses therebetween into said sampling means, at least one of said bursts of breath being of specified duration, and wherein said identity confirming means operates to identify said test subject by analyzing the timing of said bursts and said pauses.

4. The apparatus of claim 1 further comprising:
   means for sensing a parameter correlated to the flow of exhaled breath during delivery of said breath sample to said sampling means to determine whether said flow has been essentially continuously in excess of a minimum flow for at least a minimum period, said minimum flow and said minimum period being sufficient to ensure that said sample is a deep lung sample of breath.

5. The apparatus of claim 1 further comprising:
   control means operable to inhibit enablement of a machine connected to said control means in response to the generation of said test fail signal 6. The apparatus of claim 5 wherein said machine is a vehicle.

7. The apparatus of claim 1 further comprising:
   control means connected to said comparing means and connectable to a machine, said control means operating to maintain the machine in a disabled state unless at least one predetermined condition is satisfied.

8. The apparatus of claim 7 wherein a first said predetermined condition is that said electrical signal indicates less than a predetermined level of alcohol.

9. The apparatus of claim 7 wherein a second said predetermined condition is that said test fail signal is not generated.

10. A method of avoiding circumvention of a breath sobriety tester of the type having an alcohol sensor operable to generate an electrical signal related to the amount of alcohol present in breath to which the sensor is exposed, said method comprising the steps of:
    (a) delivering a first sample of exhaled breath to the alcohol sensor;
    (b) taking a first reading of the electrical signal generated by the alcohol sensor in response to said breath sample;
    (c) monitoring an attempt to perform an identity-confirming act in order to confirm the identity of a test subject in accordance with the ability of the test subject to perform said act, said act requiring delivery of a second breath sample to the sensor;
(d) taking a second reading of the electrical signal generated by the alcohol sensor in response to said second breath sample, and
(e) generating a test fail signal in the event said second reading differs from said first reading by more than a predetermined amount.

11. The method of claim 10 further comprising the step of generating a test fail signal in the event at least one of said first and second breath samples is not a deep lung breath sample.

12. The method of claim 10 wherein said test fail signal is generated only in the event said second reading exceeds said first reading by more than said predetermined amount.

13. The method of claim 10 wherein said identity-confirming act is attempted after delivery of said breath sample.

14. The method of claim 10 wherein said identity-confirming act includes blowing a plurality of bursts of breath with pauses therebetween into said sampling means, at least one of said bursts of breath being of specified duration, and wherein said identity confirming means operates to identify said test subject by analyzing the timing of said bursts and said pauses.

15. The method of claim 10 further comprising the step of sensing a parameter correlated to the flow of exhaled breath during delivery of said breath sample to said sampling means to determine whether said flow has been essentially continuously in excess of a minimum flow for at least a minimum period, said minimum flow and said minimum period being sufficient to ensure that said sample is a deep lung sample of breath.

16. The method of claim 10 further comprising the step of inhibiting enablement of a machine connected to said control means in response to the generation of said test fail signal.

17. The method of claim 16 wherein said machine is a vehicle.

* * * * *